(12) United States Patent
Nakano et al.

(10) Patent No.: US 8,173,573 B2
(45) Date of Patent: May 8, 2012

(54) VISIBLE LIGHT RESPONSE-TYPE PHOTOCATALYST POWDER, VISIBLE LIGHT RESPONSE-TYPE PHOTOCATALYST MATERIAL USING THE VISIBLE LIGHT RESPONSE-TYPE PHOTOCATALYST POWDER, PHOTOCATALYST COATING MATERIAL, AND PHOTOCATALYST PRODUCT

(75) Inventors: Kayo Nakano, Yokohama (JP); Akira Sato, Yokohama (JP); Yasuhiro Shirakawa, Yokohama (JP); Keiichi Fuse, Yokohama (JP); Masami Okamura, Yokohama (JP); Shinya Kasamatsu, Yokohama (JP); Yumi Ito, Yokohama (JP)

(73) Assignees: Kabushiki Kaisha Toshiba, Tokyo (JP); Toshiba Materials Co., Ltd., Yokohama-shi (JP)

( * ) Notice: Subject to any disclaimer, the term of this patent is extended or adjusted under 35 U.S.C. 154(b) by 0 days.

(21) Appl. No.: 12/844,453

(22) Filed: Jul. 27, 2010

(65) Prior Publication Data
US 2010/0292075 A1    Nov. 18, 2010

Related U.S. Application Data

(63) Continuation of application No. PCT/JP2009/000321, filed on Jan. 28, 2009.

(30) Foreign Application Priority Data

| Jan. 28, 2008 | (JP) | 2008-016649 |
| Jan. 28, 2008 | (JP) | 2008-016650 |
| Jan. 28, 2008 | (JP) | 2008-016651 |
| Mar. 4, 2008 | (JP) | 2008-054142 |

(51) Int. Cl.
*B01J 23/00* (2006.01)

(52) U.S. Cl. ........ 502/305; 502/308; 502/309; 502/313; 502/317; 502/318

(58) Field of Classification Search .................. 502/305, 502/308, 309, 313, 317, 318
See application file for complete search history.

(56) References Cited

U.S. PATENT DOCUMENTS

2007/0177372 A1    8/2007    Matsuda et al.
(Continued)

FOREIGN PATENT DOCUMENTS

JP    11-104500 A    4/1999
(Continued)

OTHER PUBLICATIONS

JIS Z 9110, Japanese Industrial Standard, "Recommended Levels of Illumination", Japanese Standards Association (1979), 26 pages.

(Continued)

*Primary Examiner* — Patricia L Hailey
(74) *Attorney, Agent, or Firm* — Foley & Lardner LLP

(57) ABSTRACT

In one embodiment, a visible light responsive photocatalyst powder has organic gas decomposition performance that responds nonlinearly to an amount of irradiated light under visible light in an illuminance range of not less than 200 lx nor more than 2500 lx. The visible light responsive photocatalyst powder has a gas decomposition rate of 20% or more, for example, when visible light having only a wavelength of not less than 380 nm and an illuminance of 2500 lx is irradiated, the gas decomposition rate (%) being set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow into a flow-type apparatus in which 0.2 g of a sample is placed.

61 Claims, 1 Drawing Sheet

U.S. PATENT DOCUMENTS

| | | | |
|---|---|---|---|
| 2008/0006954 A1 | 1/2008 | Yubuta et al. | |
| 2008/0119352 A1* | 5/2008 | Kitaguchi | 502/74 |
| 2008/0241542 A1* | 10/2008 | Ohtani et al. | 428/403 |
| 2010/0113254 A1* | 5/2010 | Sato et al. | 502/150 |
| 2010/0204040 A1* | 8/2010 | Nakano et al. | 502/305 |

FOREIGN PATENT DOCUMENTS

| | | |
|---|---|---|
| JP | 2000-218161 A | 8/2000 |
| JP | 2001-152130 A | 6/2001 |
| JP | 2002-293544 A | 10/2002 |
| JP | 2006-102737 A | 4/2006 |
| JP | 2008-006429 A | 1/2008 |

OTHER PUBLICATIONS

JIS R 1701-1, Japanese Industrial Standard, "Fine ceramics (advanced ceramics, advanced technical ceramics)—Test method for air purification performance of photocatalytic materials—Part 1: Removal of nitric oxide", Japanese Standards Association, (2004) with English Translation, 39 pages.

JIS Z 9112, Japanese Industrial Standard, "Classification of fluorescent lamps by chromaticity and colour rendering property", Japanese Standards Association, (2004), with English Translation, 34 pages.

JIS Z 8110, Japanese Industrial Standard, "Colour specification—Names of light-source colour", Japanese Standards Association, (1995), 17 pages.

JIS Z 8729, Japanese Industrial Standard, "Colour specification—CIELAB and CIELUV colour spaces", Japanese Standards Association, (2004), 32 pages.

Translation of International Preliminary Report on Patentability of PCT/JP2009/000321, dated Sep. 10, 2010, 11 pages.

* cited by examiner

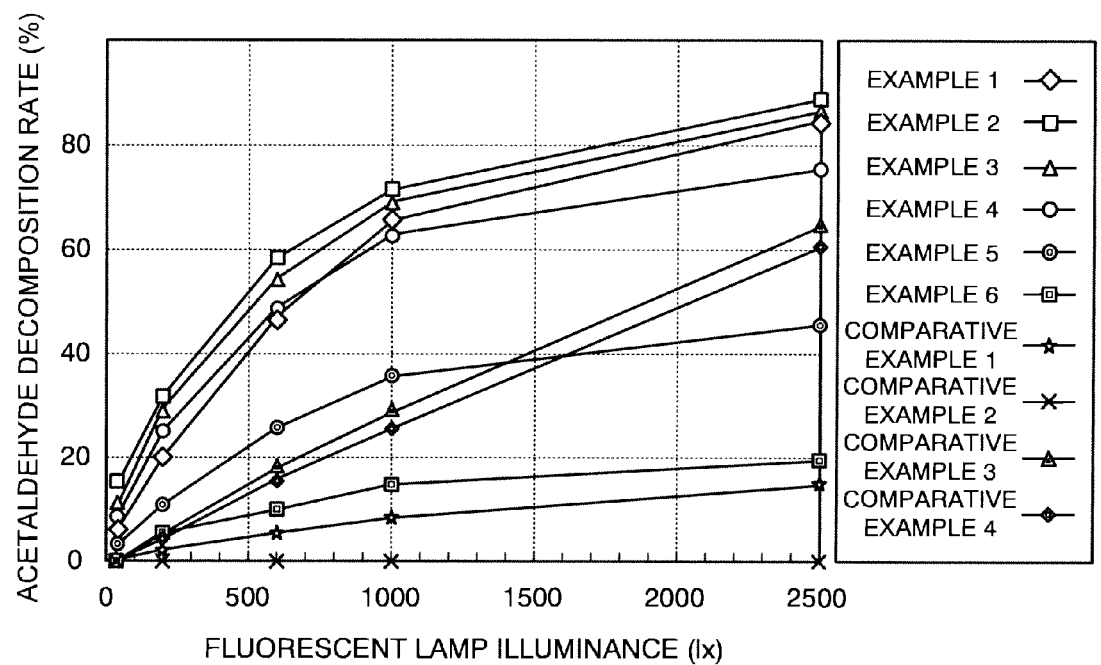

VISIBLE LIGHT RESPONSE-TYPE PHOTOCATALYST POWDER, VISIBLE LIGHT RESPONSE-TYPE PHOTOCATALYST MATERIAL USING THE VISIBLE LIGHT RESPONSE-TYPE PHOTOCATALYST POWDER, PHOTOCATALYST COATING MATERIAL, AND PHOTOCATALYST PRODUCT

CROSS-REFERENCE TO RELATED APPLICATION

This application is continuation of prior International Application No. PCT/JP2009/000321, filed on Jan. 28, 2009 which is based upon and claims the benefit of priority from Japanese Patent Application No. 2008-016649, filed on Jan. 28, 2008, No. 2008-016650, filed on Jan. 28, 2008, No. 2008-016651, filed on Jan. 28, 2008 and No. 2008-054142, filed on Mar. 4, 2008; the entire contents of all of which are incorporated herein by reference.

FIELD

Embodiments described herein relate generally to a visible light responsive photocatalyst powder, and visible light responsive photocatalyst material, photocatalyst coating material and photocatalyst product each using the same.

BACKGROUND

As a photocatalyst material used in the application for stain-proofing and deodorization, titanium oxide is known. The photocatalyst material is used in various fields of exterior and interior building materials, home appliances such as lighting devices, refrigerators, air-conditioners, and toilets. However, titanium oxide cannot exhibit sufficient photocatalytic performance in indoor environments having only a small amount of ultraviolet rays because it is excited by an ultraviolet region. Therefore, research and development have been in progress for a visible light responsive photocatalyst exhibiting photocatalytic performance even by visible light.

Regarding also the titanium oxide used as an ultraviolet light response-type photocatalyst, a method of doping nitrogen or sulfur in the titanium oxide, or making the titanium oxide support a metal or the like has been studied to improve performance as a visible light responsive photocatalyst. These photocatalysts cannot exhibit sufficient performance in an actual residential space in which application of photocatalyst is expected, except in the vicinity of or right below an illumination light source, since their photocatalytic activities are, under an amount of light with an illuminance of normal interior illumination (about several lx to 3000 lx), in proportion to the amount of light.

Photocatalysis is considered as an action in which light is absorbed to excite a pair of electrons and positive holes with respect to one photon, the excited electrons and positive holes activate a hydroxyl group and oxygen on a surface through oxidation-reduction, and reactive oxygen species generated by the activation perform oxidative decomposition on organic gas and the like. Therefore, the photocatalysis of the photocatalyst is lowered in an area having a small amount of light (low illuminance area). Further, an amount of gas decomposition realized by a photocatalyst is generally in proportion to the amount of light (number of photons). When an amount of irradiated light is large with respect to an organic matter on a surface, saturation occurs and an amount of photocatalysis is not in proportion to the amount of light, but, in a known photocatalyst, an amount of photocatalysts in an area having a small amount of light (low illuminance area) has a linear relation to the amount of light.

Generally, an illuminance for evaluating performance of the visible light responsive photocatalyst is equal to or more than 6000 lx. Although there is titanium oxide which is activated by visible light under such a high illuminance, since the photocatalytic activity is decreased rapidly in accordance with the decrease in the illuminance, the titanium oxide cannot exhibit sufficient performance as the visible light responsive photocatalyst under a practical environment. An application of catalyst film having a wide area is effective for indoor deodorization and removal of toxic gas such as formaldehyde, but, since an illuminance on a ceiling, a wall and a floor with wide area is low, practicality is low unless a material which exerts an effect under a low illuminance is employed.

As the visible light responsive photocatalyst, tungsten oxide is known. Patent document 1 describes a photocatalyst material made of tungsten oxide sputter-deposited on a base material, and tungsten oxide having a triclinic crystal structure is mainly used. Since the sputter deposition exposes the base material to high temperature, heat resistance temperature of some base material does not allow the application of the sputter deposition. Since a process control or the like of the sputter deposition is complicated, and it not only costs high depending on the shape and size of the base material but also has a difficulty in the deposition on a wide range such as on building materials. Moreover, though excellent in hydrophilic property, a visible light responsive photocatalyst layer made of sputter-deposited tungsten oxide has a problem that its performance of decomposing toxic gas such as acetaldehyde is not high enough. Since no data on the hydrophilic property under the irradiation of visible light is shown, it is estimated that sufficient photocatalytic performance is not obtained under visible light.

The use of a tungsten oxide powder as a photocatalyst has been also studied. If in a powder state, tungsten oxide can be mixed with a binder such as resin to be applied on a base material, which eliminates the need to expose the base material to high temperature and makes it possible to form a coating film even on a wide range such as on building materials. As a method of manufacturing the tungsten oxide powder, there has been known a method of obtaining a tungsten trioxide powder by heating ammonium paratungstate (APT) in the air (refer to Patent Document 2). The method of heating APT in the air provides a triclinic tungsten trioxide powder whose particle size is 0.01 μm (BET specific surface area=82 m²/g).

The tungsten trioxide ($WO_3$) powder generated by the heating of APT in the air needs to have fine particles in order to have improved photocatalytic performance. However, applying a disintegration process can make the particle size small to some degree but has a difficulty in realizing the particle size of 100 nm or less, for instance. Moreover, turning it to fine powder by the use of the disintegration process causes a change in the crystal structure of the tungsten trioxide ($WO_3$) fine powder due to a stress by the disintegration process. Since the stress of the disintegration process causes a defect of the occurrence of the re-combination of electrons and positive holes, it is thought that photocatalytic performance is deteriorated. Meanwhile, the manufacturing method described in Patent Document 2 has a problem of low manufacturing efficiency of the tungsten trioxide powder since it requires 20 hour or more kneading in order to stabilize the BET specific surface area.

As a method of efficiently obtaining a fine powder, Patent Document 3, for instance, describes a thermal plasma process. A fine powder whose particle size is 1 to 200 nm is obtained by the application of the thermal plasma process. The thermal plasma process can efficiently provide a fine powder, but even if the tungsten oxide fine powder produced by the use of the method described in Patent Document 3 is used as a photocatalyst as it is, it is not always possible to obtain a sufficient photocatalytic property. It is thought that this is because the tungsten oxide fine powder produced by the thermal plasma method does not sometimes have an optimum optical property or crystal structure.

Tungsten oxide comes in various kinds such as $WO_3$ (tungsten trioxide), $WO_2$ (tungsten dioxide), WO, $W_2O_3$, $W_4O_5$, and $W_4O_{11}$. Among them, tungsten trioxide ($WO_3$) is mainly used as a photocatalyst material because of its excellent photocatalytic performance and its stability in a room-temperature atmosphere. However, tungsten trioxide ($WO_3$) has a disadvantage that its photocatalytic performance is not stable because of its complicated crystal structure and its changeability by a small stress. Moreover, even if having a stable crystal structure, tungsten trioxide ($WO_3$) cannot exhibit sufficient photocatalytic performance if its surface area is small.

Incidentally, the indoor is an environment in which an amount of ultraviolet ray is small. Further, an illuminance in the indoor is, at most, 3000 lx or less, and is several 100 lx or less except on a desk and in a workplace. For instance, a standard of the illuminance in the indoor is provided by "Recommended levels of illumination" of JIS-Z-9110 (1979) depending on each place and contents of work. According to the "Recommended levels of illumination", a local illumination in a store, a department store and the like, and a place such as a factory in which a very delicate work is performed are defined to have a somewhat high illuminance of 1500 to 3000 lx.

However, an illuminance in a normal office, a common manufacturing process in a factory, and a place in a home where a delicate work is performed is equal to or less than 1500 lx, and further, an illuminance in a living room in a home where people enjoy gathering and a place of dining table in a dining room is low to be 500 to 150 lx. Regarding a ceiling, a wall, a floor, a furniture, a home electric appliance and the like to which the application of visible light responsive photocatalyst is expected, an illuminance of places where they are disposed is around 50 lx, which is significantly low. In particular, an illumination in a hallway and awash room is low, so that an illuminance in the vicinity of walls of such places is less than 50 lx. There is no conventional photocatalyst that exhibits practical photocatalytic performance under visible light with such a low illuminance.

[Reference 1] JP-A 2001-152130 (KOKAI)
[Reference 2] JP-A 2002-293544 (KOKAI)
[Reference 3] JP-A 2006-102737 (KOKAI)

BRIEF DESCRIPTION OF THE DRAWINGS

FIG. 1 is a view showing a relation between irradiation illuminances and gas decomposition rates when visible light (from white fluorescent lamp) is irradiated to visible light responsive photocatalyst powders according to examples.

DETAILED DESCRIPTION

In one embodiment, a visible light responsive photocatalyst powder has organic gas decomposition performance that responds nonlinearly to an amount of irradiated light under visible light in an illuminance range of not less than 200 lx nor more than 2500 lx.

In one embodiment, the visible light responsive photocatalyst powder has a gas decomposition rate of 20% or more when visible light having only a wavelength of not less than 380 nm and an illuminance of 2500 lx is irradiated by using a white fluorescent lamp and an ultraviolet cutoff filter. The gas decomposition rate (%) is set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

In one embodiment, the visible light responsive photocatalyst powder has a gas decomposition rate of 20% or more when visible light having only a wavelength of not less than 410 nm and an illuminance of 2500 lx is irradiated by using a white LED lamp. The gas decomposition rate (%) is set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

In another embodiment, a visible light responsive photocatalyst powder includes a tungsten oxide powder or a tungsten oxide composite material powder, in which a ratio (G2/G1) of a gas decomposition rate (G2) when visible light having only a wavelength of not less than 380 nm and an illuminance of 2500 lx is irradiated to the visible light responsive photocatalyst powder with any sample amount with respect to a gas decomposition rate (G1) when visible light having only a wavelength of not less than 380 nm and an illuminance of 6000 lx is irradiated to the visible light responsive photocatalyst powder with the same sample amount at the time of irradiating the visible light having the illuminance of 2500 lx by using a white fluorescent lamp and an ultraviolet cutoff filter is 74% or more. The gas decomposition rate (%) is set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which a sample is placed.

In another embodiment, a visible light responsive photocatalyst powder includes a tungsten oxide powder or a tungsten oxide composite material powder. The visible light responsive photocatalyst powder has a gas decomposition rate of 5% or more when visible light having only a wavelength of not less than 380 nm and an illuminance of 200 lx is irradiated by using a white fluorescent lamp and an ultraviolet cutoff filter. The gas decomposition rate (%) being set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

In one embodiment, a visible light responsive photocatalyst material contains the visible light responsive photocatalyst powder according to the embodiment whose content falls within a range of not less than 1 mass % nor more than 100 mass %. A visible light responsive photocatalyst coating material contains the visible light responsive photocatalyst material according to the embodiment whose content falls within a range of not less than 0.1 mass % nor more than 90 mass %. A visible light responsive photocatalyst product includes the visible light responsive photocatalyst material according to the embodiment, or a coating layer of the visible light responsive photocatalyst coating material according to the embodiment.

A visible light responsive photocatalyst powder according to a first embodiment has organic gas decomposition performance which responds nonlinearly to an amount of irradiated light under visible light in an illuminance range of not less than 200 lx nor more than 2500 lx. Such a visible light responsive photocatalyst powder firstly exhibits a gas decomposition rate of 20% or more, in a gas decomposition test to be described hereinbelow, when irradiated with visible light having only a wavelength of not less than 380 nm and an illuminance of 2500 lx. Further, it is preferable that the visible light responsive photocatalyst powder has a gas decomposition rate of 15% or more when irradiated with visible light having only a wavelength of not less than 380 nm and an illuminance of 1000 lx, and a gas decomposition rate of 10% or more when irradiated with visible light having only a wavelength of not less than 380 ma and an illuminance of 600 lx.

The visible light responsive photocatalyst powder according to the first embodiment secondary exhibits a gas decomposition rate of 20% or more when irradiated with visible light having only a wavelength of not less than 410 nm and an illuminance of 2500 lx. It is preferable that the visible light responsive photocatalyst powder has a gas decomposition rate of 15% or more when irradiated with visible light having only a wavelength of not less than 410 nm and an illuminance of 1000 lx, and a gas decomposition rate of 10% or more when irradiated with visible light having only a wavelength of not less than 410 nm and an illuminance of 600 lx.

The gas decomposition test for determining the aforementioned gas decomposition rates is conducted by using a flow-type apparatus as is used in the evaluation of nitrogen oxide removal performance (decomposition performance) of JIS-R-1701-1 (2004). The gas concentrations are measured by allowing an acetaldehyde gas having an initial concentration of 10 ppm to flow, at 140 mL/min, into the flow-type apparatus in which 0.2 g of a sample is placed. In such gas concentrations, a gas concentration before light irradiation is set as A, and a gas concentration when not less than 15 minutes have elapsed from the light irradiation and, at the same time, the gas concentration is stable, is set as B. Subsequently, from the gas concentration A and the gas concentration B, a value calculated based on [formula: $(A-B)/A \times 100$] is set as the gas decomposition rate (%).

Generally, visible light corresponds to light whose wavelength is in a range of 380 to 830 nm. In order to evaluate further excellent performance under visible light similar to that under an actual usage environment, it is assumed that visible light having only a wavelength of not less than 380 nm is used in a first performance evaluation of this embodiment. Concretely, it is preferable to perform evaluation by irradiating visible light having only a wavelength of not less than 380 nm by using a white fluorescent lamp defined in JIS-Z-9112 as a light source and an ultraviolet cutoff filter cutting off light whose wavelength is less than 380 nm. As the white fluorescent lamp, for instance, FL20SS•W/18 manufactured by Toshiba Lighting & Technology Corporation or an equivalent thereof is used. As the ultraviolet cutoff filter, Clarex N-169 (product name) manufactured by Nitto Jushi Kogyo Co., Ltd., or an equivalent thereof is used.

In the indoor where the visible light responsive photocatalyst is mainly used, excitation light is light from illumination lamps and natural light from windows, but, excitation light in a place in a living space where an illuminance is low is often only light from illumination lamps. The most generally used illumination light source in the indoor is a white fluorescent lamp. The first performance evaluation of the visible light responsive photocatalyst powder of the first embodiment is assumed to be performed by using the white fluorescent lamp. This enables to obtain a value closest to that of practical performance.

A white LED (Light Emitting Diode) lamp is expected as a lighting fixture alternative to the white fluorescent lamp. The visible light responsive photocatalyst powder of the first embodiment exhibits good performance also under an environment where the white LED lamp is used. In a second performance evaluation, visible light having only a wavelength of not less than 410 nm is used to evaluate performance under illumination provided by the white LED lamp. Concretely, it is preferable that a white LED lamp in which an InGaN-type blue LED and a yellow emitting phosphor are combined is used as a light source, and visible light having only a wavelength of not less than 410 nm is irradiated to perform evaluation. As the white LED lamp, for instance, NSPW-510CS manufactured by Nichia chemical Co., Ltd., or a white LED lamp having an emission spectrum equal to that thereof is used.

The white LED lamp is an element that produces white light by utilizing light from LED chips, and can be largely divided into three types depending on the way of producing the white light. One is a white LED lamp in which an InGaN-type blue LED and a yellow emitting phosphor are combined, that produces, by applying blue light to the phosphor to output yellow light, white light by mixing colors of the blue light and the yellow light, and this type of white LED lamp is currently used as a mainstream. Another one is a white LED lamp that produces, by applying light emitted from a near-ultraviolet LED chip to a plurality of phosphors, white light by mixing colors of light emitted from the phosphors. Further, the other one is a white LED lamp that obtains, by making respective LED chips of R (red), G (Green), and B (blue) simultaneously emit light, white light by mixing colors of light emitted from the LED chips.

White light emitted from a white LED lamp used for the second performance evaluation of the visible light responsive photocatalyst powder of the first embodiment preferably has a white color within a range of CIE chromaticity including yellowish white, greenish white, bluish white, purplish white, light pink, and white indicated by an attached diagram for reference 1 (general chromaticity classification of systematic color names) of JIS-Z-8110 (1995).

In the indoor where the visible light responsive photocatalyst is mainly used, excitation light is light from illumination lamps and natural light from windows, but, excitation light in a place in a living space where an illuminance is low is often only light from illumination lamps, and it is often a case where the irradiated light has only a wavelength which is within a visible spectrum. By assuming an environment where a white LED lamp is used as an illumination lamp, the second performance evaluation is supposed to be conducted by using light from the white LED lamp as visible light having only a wavelength of not less than 410 nm. The white LED lamp is expected as a lighting fixture for the next generation alternative to a white fluorescent lamp. By conducting the performance evaluation using the white LED lamp, it is possible to obtain a value close to that of practical performance (gas decomposition performance) under an environment in which such a lighting fixture is used.

The second performance evaluation of the visible light responsive photocatalyst powder of the first embodiment is conducted by using a white LED lamp in which an InGaN-type blue LED chip and a yellow emitting phosphor are combined. However, it goes without saying that at a time of actual usage, sufficient photocatalytic performance can be obtained even by using white light from an LED lamp in which a near-ultraviolet LED chip and a plurality of phosphors are combined, or white light produced by mixing colors of light from respective LED chips of R (red), G (Green), and B (blue).

Based on a gas decomposition rate (20% or more) under the irradiation of visible light having only a wavelength of not less than 380 nm and an illuminance of 2500 lx or visible light having only a wavelength of not less than 410 nm and an illuminance of 2500 lx, and further, based on a gas decomposition rate (15% or more) under the irradiation of visible light with various wavelengths and an illuminance of 1000 lx, and a gas decomposition rate (10% or more) under the irradiation of visible light with various wavelengths and an illuminance of 600 lx, the visible light responsive photocatalyst powder of the first embodiment can exhibit practical gas decomposition performance also under an indoor environment and the like in which an illuminance is low.

Specifically, it becomes possible to obtain practical gas decomposition performance under a low illuminance, based on organic gas decomposition performance that responds nonlinearly to an amount of irradiated light. For example, it is possible to realize a gas decomposition rate of 5% or more under an illuminance of about 200 lx such as an illuminance in a living room where people enjoy gathering, a wash room and the like in a home. Further, it is possible to obtain a gas decomposition rate within a practical range also under a significantly low illuminance of around 50 lx such as an illuminance on a wall and in a place where a furniture, a home electric appliance and the like are disposed in the indoor.

Photocatalysis is an action in which electrons and positive holes excited by light activate a hydroxyl group and oxygen on a surface through oxidation-reduction, and reactive oxygen species generated by the activation perform oxidative decomposition on organic gas and the like. Therefore, an amount of gas decomposition realized by a photocatalyst is generally in proportion to the amount of light (number of photons), and when an illuminance is lowered, the amount of gas decomposition is also decreased in proportion thereto.

Meanwhile, the visible light responsive photocatalyst powder of the first embodiment exhibits not only high photocatalytic performance (gas decomposition rate=50% or more) under a significantly high illuminance such as an illuminance of 6000 lx, but also a gas decomposition rate of 20% or more under the irradiation of visible light with an illuminance of 2500 lx. The visible light responsive photocatalyst powder exhibits performance different from that of a conventional visible light responsive photocatalyst powder, and it suppresses the decrease in the photocatalytic activity in accordance with the decrease in the illuminance. For this reason, it is possible to obtain practical gas decomposition performance under an illuminance of about 200 lx and also under a significantly low illuminance of around 50 lx. Therefore, it becomes possible to obtain gas decomposition performance under an indoor environment such as a living room where people enjoy gathering, a toilet, a wash room and the like in which an illuminance is low, and also under a significantly low illuminance on a wall, a ceiling, and in a place where a furniture, a home electric appliance and the like are disposed and the like in the indoor.

As described above, in order to obtain practical gas decomposition performance under a low illuminance of 200 lx or less or even 50 lx or less, the visible light responsive photocatalyst powder preferably has a gas decomposition rate of 15% or more when irradiated with visible light having an illuminance of 1000 lx, and a gas decomposition rate of 10% or more when irradiated with visible light having an illuminance of 600 lx. By realizing the gas decomposition rates under such illuminances, the decrease in the photocatalytic activity in accordance with the decrease in the illuminance is further suppressed, which enables to obtain practical gas decomposition performance under a low illuminance in a more reproducible manner.

To exhibit a gas decomposition rate of 20% or more when visible light with an illuminance of 2500 lx is irradiated to the visible light responsive photocatalyst powder means to be able to obtain excellent gas decomposition performance not only under an environment of significantly high illuminance such as an illuminance of 6000 lx but also under an environment of somewhat high illuminance such as right below an illumination from a white fluorescent lamp, a white LED lamp or the like. To exhibit a gas decomposition rate of 15% or more when visible light having an illuminance of 1000 lx is irradiated and further, to exhibit a gas decomposition rate of 10% or more when visible light having an illuminance of 600 lx is irradiated means to be able to obtain good gas decomposition performance in an office and under an environment where a delicate work is performed and also under an environment when reading books and the like. According to the visible light responsive photocatalyst powder of the first embodiment, gas decomposition performance can be exhibited under various types of visible light with various illuminances.

A gas decomposition rate when visible light with an illuminance of 2500 lx is irradiated to the visible light responsive photocatalyst powder is preferably 45% or more. A gas decomposition rate when visible light having an illuminance of 1000 lx is irradiated is preferably 35% or more, and a gas decomposition rate when visible light having an illuminance of 600 lx is irradiated is preferably 25% or more. With the use of a visible light responsive photocatalyst powder satisfying such conditions, it is possible to realize a gas decomposition rate of 10% or more under an illuminance of about 200 lx, for instance. Further, it is possible to realize a gas decomposition rate of 5% or more also under a significantly low illuminance of around 50 lx such as an illuminance on a wall, and in a place where a furniture, a home electric appliance and the like are disposed in the indoor.

The visible light responsive photocatalyst powder having the gas decomposition rates as described above is formed of, for instance, a tungsten oxide powder. The visible light responsive photocatalyst powder can be formed not only of a single powder of tungsten oxide but also of a tungsten oxide composite material powder. The tungsten oxide composite material powder is formed by making tungsten oxide as a main component contain at least one metal element selected from Ti, Fe, Cu, Zr, Ag, Pt, Pd, Mn, Al and Ce in a range of 50 mass % or less, for instance. If a content of the metal element is more than 50 mass %, a remarkable effect of tungsten oxide may not be sufficiently exhibited. The content of the metal element is more preferably 10 mass % or less.

The tungsten oxide composite material powder that forms the visible light responsive photocatalyst powder can contain the metal element in various forms. The tungsten oxide composite material powder can contain the metal element in a form of an elemental substance of the metal element, a compound containing the metal element, a composite compound with tungsten oxide or the like. The metal element itself contained in the tungsten oxide composite material powder may form a compound with another element. As a typical form of the metal element, an oxide can be cited. The metal element is mixed with the tungsten oxide powder in a form of an elemental substance, a compound, a composite compound, or the like. The metal element may be supported by tungsten oxide.

As a concrete example of the tungsten oxide composite material powder, there can be cited a powder which contains a copper oxide powder in a range of not less than 1 mass % nor more than 5 mass %. Also a metal oxide powder (titanium oxide powder, iron oxide powder or the like) other than the copper oxide powder is preferably contained in the tungsten oxide composite material powder in a range of not less than 1 mass % nor more than 5 mass %. The tungsten oxide composite material may also contain a tungsten compound other than the oxide, which is, for instance, tungsten carbide. Tungsten carbide is mixed, as its powder, with the tungsten oxide powder in a range of not less than 1 mass % nor more than 5 mass %.

A composite method of tungsten oxide and the metal element (concretely, an elemental substance, a compound, or a composite compound of at least one element selected from Ti, Fe, Cu, Zr, Ag, Pt, Pd, Mn, Al and Ce) is not particularly limited, and various composite methods such as a mixing method for mixing respective powders, an impregnate ion method and a supporting method can be applied. A typical composite method will be described hereinbelow. As a method of compounding copper into tungsten oxide, there can be cited a method of mixing a tungsten oxide powder with a copper oxide powder, a copper nitrate powder, a copper sulfate powder or the like. Further, a method of adding a tungsten oxide powder to an aqueous solution of copper nitrate or copper sulfate or an ethanol solution and mixing them together, drying the mixture at a temperature of 70 to 80° C., and baking the resultant at a temperature of 500 to 550° C., is also effectively utilized.

As a method of compounding copper into tungsten oxide, a method in which a tungsten oxide powder is dispersed in an aqueous copper chloride solution or an aqueous copper sulfate solution and the dispersion liquid is dried (impregnation method), for instance, can also be applied. The impregnation method can also be applied not only to the composite method of copper but also to a composite method of iron using an aqueous iron chloride solution, a composite method of iron using an aqueous silver chloride solution, a composite method of platinum using an aqueous chloroplatinic acid solution, a composite method of palladium using an aqueous palladium chloride solution and the like. Further, it is also possible to compound tungsten oxide and the metal element (oxide) using an oxide sol such as a titanium oxide sol and an alumina sol. Various composite methods other than the aforementioned methods can also be applied.

The tungsten oxide powder or the tungsten oxide composite material powder (hereinafter, these powders are named generically as tungsten oxide type powder) forming the visible light responsive photocatalyst powder can obtain properties as described above by controlling its particle size (specific surface area), crystal structure, crystallinity, powder color and the like. The tungsten oxide type powder preferably has a BET specific surface area in a range of 4.1 to 820 $m^2/g$. The tungsten oxide type powder preferably has an average particle size in a range of 1 to 200 nm. It is assumed that the average particle size is determined based on an average particle size of particles in number n=50 or more (D50) by image analysis of a photograph of SEM, TEM, or the like. The average particle size (D50) may be equal to the average particle size converted from the specific surface area.

The larger the specific surface area and the smaller the particle size, the higher the performance of the photocatalyst powder. Therefore, when the BET specific surface area of the tungsten oxide type powder is less than 4.1 $m^2/g$ or when the average particle size is greater than 200 nm, sufficient photocatalytic performance cannot be obtained. Meanwhile, when the BET specific surface area of the tungsten oxide type powder is over 820 $m^2/g$ or when the average particle size is less than 1 nm, the particle becomes too small, and practicability is lowered because handlability as powder deteriorates. The BET specific surface area of the tungsten oxide type powder is preferably in a range of 8.2 to 410 $m^2/g$, and the average particle size is preferably in a range of 2 to 100 nm.

The BET specific surface area of the tungsten oxide type powder is preferably in a range of 11 to 300 $m^2/g$, and more preferably, in a range of 16 to 150 $m^2/g$. The average particle size is preferably in a range of 2.7 to 75 nm, and more preferably, in a range of 5.5 to 51 nm. When the tungsten oxide type powder is applied to a visible light responsive photocatalyst coating material or the like, too small a particle size results in poor dispersibility of particles and results in a difficulty in turning it into the coating material. To solve such problems, a tungsten oxide type powder whose average particle size is 5.5 nm or more is preferably used.

It is preferable that tungsten oxide that forms the tungsten oxide powder or the tungsten oxide composite material powder has a crystal structure of at least one selected from a monoclinic crystal and a triclinic crystal of tungsten trioxide, or a crystal structure in which a rhombic crystal is mixed with at least one selected from the monoclinic crystal and the triclinic crystal. The tungsten oxide powder and the tungsten oxide composite material powder using tungsten oxide having such a crystal structure can stably exhibit excellent photocatalytic performance. Though it is difficult to determine abundance ratios of the respective crystal phases of tungsten trioxide, it can be estimated that a powder has the above-described crystal structure when it satisfies the conditions (1) to (4) described below when measured by X-ray diffractometry.

(1) In an X-ray diffraction chart, the tungsten oxide type powder has a first peak (a diffraction peak with the highest intensity among all peaks), a second peak (a diffraction peak with the second highest intensity), and a third peak (a diffraction peak with the third highest intensity) in a 22.5 to 25° 2θ range.

(2) In the X-ray diffraction chart, an intensity ratio of a peak A to a peak D (A/D) and an intensity ratio of a peak B to the peak D (B/D) each fall within a range of 0.5 to 2.0, and an intensity ratio of a peak C to the peak D (C/D) falls within a range of 0.04 to 2.5, wherein the peak A is a peak existing in a 22.8 to 23.4° 2θ range, the peak B is a peak existing in a 23.4 to 23.8° 2θ range, the peak C is a peak existing in a 24.0 to 24.25° 2θ range, and the peak D is a peak existing in a 24.25 to 24.5° 2θ range.

(3) In the X-ray diffraction chart, an intensity ratio of a peak E to a peak F (E/F) falls within a range of 0.1 to 2.0, wherein the peak E is a peak existing in a 33.85 to 34.05° 2θ range and the peak F is a peak existing in a 34.05 to 34.25° 2θ range.

(4) In the X-ray diffraction chart, an intensity ratio of a peak G to a peak H (G/H) falls within a range of 0.04 to 2.0, wherein the peak G is a peak existing in a 49.1 to 49.7° 2θ range and the peak H is a peak existing in a 49.7 to 50.3° 2θ range.

The measurement and analysis of the X-ray diffraction will be described. In the measurement of the X-ray diffraction, it is assumed that a Cu target and a Ni filter are used, only smoothing and background subtraction are performed so as to prevent the analysis from being influenced by a difference in processing condition, and peak intensities are measured without any Kα2 removal. Here, as for the way to read the peak intensities in the 2θ ranges in the X-ray diffraction chart, when a mountain is clearly seen, high positions of the mountain in this range are considered as peaks and heights of the peaks are read. When a mountain is not clearly seen but there are shoulders, the shoulder portions are considered as peaks in this range and heights of the shoulder portions are read. In a case of a gradient without any mountain or shoulder, heights at mid-points in this range are read and the read values are considered as the peak intensities in this range.

Further, the tungsten oxide type powder preferably has color whose a* is −5 or less, b* is 5 or more, and L* is 70 or more when the color of the powder is expressed by the L*a*b* color system (L-star/a-star/b-star color system). The L*a*b* color system is a method used to express color of an object and is standardized by Commission Intanationale del'Eclairage (CIE) in 1976, and its definition is in JIS Z-8729 in Japan. L* expresses lightness and a* and b* express hue and saturation. The larger *L is, the higher lightness is expressed. a* and b* express the directions of color, a* expressing a red direction, −a* expressing a green direction, b* expressing a yellow direction, and −b* expressing a blue direction. Further, saturation is expressed by $(c^*)=((a^*)^2+(b^*)^2)^{1/2}$.

The tungsten oxide type powder preferably has color whose a* is −5 or less, *b is 5 or more, and L* is 70 or more, and more preferably has color whose a* is in a range of −25 to −8, b* is in a range of 10 to 45, and L* is 85 or more. Such numerical values of the L*a*b* color system indicate that the tungsten oxide type powder has a hue from yellow to the vicinity of green and has high saturation and lightness. When the tungsten oxide type powder has such an optical property, its photocatalytic performance by visible light excitation can be improved. The color tone of the tungsten oxide powder is thought to change based on composition fluctuation due to oxygen deficiency or the like, light irradiation, and so on, and when the powder has the above-described hue, saturation, and lightness, good photocatalytic performance can be obtained. When the powder has a hue close to blue, it is thought that there is a high degree of oxygen deficiency or the like, and with such a hue, the deterioration in the photocatalytic performance is observed.

By using the tungsten oxide type powder having the particle size (specific surface area), the crystal structure, the powder color and the like as described above and further having an improved crystallinity, it is possible to obtain a visible light responsive photocatalyst powder which exhibits a gas decomposition rate of 20% or more when irradiated with visible light having an illuminance of 2500 lx and further, a gas decomposition rate of 15% or more when irradiated with visible light having an illuminance of 1000 lx, and a gas decomposition rate of 10% or more when irradiated with visible light having an illuminance of 600 lx. Here, the performance of the visible light responsive photocatalyst powder cannot be improved only by the specific surface area and the particle size.

When titanium oxide is employed, it is possible to improve a visible light responsiveness by increasing absorbing performance of visible light by doping nitrogen or sulfur in the titanium oxide. Further, by improving a crystallinity by controlling a heat treatment temperature or by making the titanium oxide support a metal, it becomes possible to increase a photocatalytic activity by preventing the re-combination of electrons and positive holes. However, although there currently exists titanium oxide that exhibits high performance under a significantly high illuminance, since the performance is deteriorated in accordance with the decrease in the illuminance, there is no titanium oxide that exhibits practical gas decomposition performance under a low illuminance of about 150 to 500 lx being a common level.

On the contrary, by applying the tungsten oxide type powder having absorbing performance of visible light to the visible light responsive photocatalyst powder in which the BET specific surface area and the average particle size (D50) and further, the crystal structure, the powder color and so on of the tungsten oxide type powder are controlled as described above and besides, the crystallinity of the tungsten oxide type powder is improved, it becomes possible to realize a gas decomposition rate of 20% or more under an illuminance of 2500 lx. This is because of combined effects such that a gas absorption amount is increased by enlarging the specific surface area of the photocatalyst powder, activated sites can be accordingly increased, and further, a probability of the occurrence of re-combination is decreased because of the improved crystallinity.

Tungsten oxide has a band gap of 2.5 to 2.8 eV, which is smaller than that of titanium oxide, and accordingly, it absorbs visible light. Therefore, it is possible to realize an excellent visible light responsiveness. Further, since a typical crystal structure of tungsten oxide is $ReO_3$ structure, a crystal plane having oxygen on an outermost layer of its surface and having a high reaction activity is likely to be exposed. For this reason, tungsten oxide exhibits a high hydrophilic property by absorbing water. Alternatively, an OH radical is generated by oxidizing the absorbed water, which enables to oxidize a molecule and a compound, so that it becomes possible that the photocatalytic performance which is better than that provided by an anatase or rutile crystal of titanium oxide is exhibited. Besides, the tungsten oxide powder of this embodiment is excellent in dispersibility since its zeta potential in an aqueous solution with pH 1 to 7 is minus, and thus can be applied thinly and evenly on a base material and the like.

Examples of the photocatalytic performance are performance of decomposing organic gas such as acetaldehyde and formaldehyde, a hydrophilic property, antibacterial performance, and disinfection performance. The visible light responsive photocatalyst powder of this embodiment has excellent photocatalytic performance when irradiated with 430 to 500 nm light. Examples of an excitation source emitting light with a 430 to 500 nm wavelength are sunlight, a fluorescent lamp, a blue-emitting diode, a blue laser, and the like. In particular, the blue-emitting diode and the blue laser are preferable since they can emit only light with a 430 to 500 nm wavelength.

The tungsten oxide type powder that forms the visible light responsive photocatalyst powder may contain a metal element as impurities. The content of the metal element as the impurity element is preferably 2 mass % or less. Examples of the impurity metal element are an element normally contained in a tungsten mineral and a contaminant element which is mixed when a tungsten compound or the like used as a raw material is produced, and examples thereof are Fe, Mo, Mn, Cu, Ti, Al, Ca, Ni, Cr, Mg, and the like, for instance. It is not limited to the above examples when these elements are used as constituent elements of a composite material.

Next, a visible light responsive photocatalyst powder according to a second embodiment will be described. The visible light responsive photocatalyst powder according to the second embodiment includes a tungsten oxide powder or a tungsten oxide composite material powder. The visible light responsive photocatalyst powder as described above has a property such that a ratio (G2/G1) of a gas decomposition rate (G2) when visible light having only a wavelength of not less than 380 nm and an illuminance of 2500 lx is irradiated to the visible light responsive photocatalyst powder with any sample amount with respect to a gas decomposition rate (G1) when visible light having only a wavelength of not less than 380 nm and an illuminance of 6000 lx is irradiated to the visible light responsive photocatalyst powder with the same sample amount at the time of irradiating the visible light having the illuminance of 2500 lx in a gas decomposition test to be described hereinbelow is 74% or more.

The gas decomposition test for determining the aforementioned gas decomposition rates is conducted by using a flow-type apparatus as is used in the evaluation of nitrogen oxide removal performance (decomposition performance) of JIS-R-1701-1 (2004). The gas concentrations are measured by allowing an acetaldehyde gas having an initial concentration of 10 ppm to flow, at 140 mL/min, into the flow-type apparatus in which any amount of sample is placed. In such gas concentrations, a gas concentration before light irradiation is set as A, and a gas concentration when not less than 15 minutes have elapsed from the light irradiation and, at the same time, the gas concentration is stable, is set as B. Subsequently, from the gas concentration A and the gas concentration B, a value calculated based on [formula: $(A-B)/A \times 100$] is set as the gas decomposition rate (%). The measurement of gas decomposition rates under respective illuminances is assumed to be conducted by putting the visible light responsive photocatalyst powder with the same sample amount into the flow-type apparatus.

Generally, visible light corresponds to light whose wavelength is in a range of 380 to 830 nm. In order to evaluate further excellent performance under visible light similar to that under an actual usage environment, it is assumed that visible light having only a wavelength of not less than 380 nm is used in the evaluation of the second embodiment. Concretely, it is preferable to perform evaluation by irradiating visible light having only a wavelength of not less than 380 nm by using a white fluorescent lamp defined in JIS-Z-9112 as a light source and an ultraviolet cutoff filter cutting off light whose wavelength is less than 380 nm. As the white fluorescent lamp, for instance, FL20SS•W/18 manufactured by Toshiba Lighting & Technology Corporation or an equivalent thereof is used. As the ultraviolet cutoff filter, Clarex N-169 (product name) manufactured by Nitto Jushi Kogyo Co., Ltd., or an equivalent thereof is used.

In the indoor where the visible light responsive photocatalyst is mainly used, excitation light is light from illumination lamps and natural light from windows, but, excitation light in a place in a living space where an illuminance is low is often only light from illumination lamps. The most generally used illumination light source in the indoor is a white fluorescent lamp, so that the performance measurement of the visible light responsive photocatalyst powder of this embodiment is assumed to be performed by using the white fluorescent lamp. This enables to obtain a value closest to that of practical performance. Similar to the first embodiment, the visible light responsive photocatalyst powder of the second embodiment exhibits a similar gas decomposition rate also when visible light having only a wavelength of not less than 410 nm is irradiated using a white LED lamp.

Based on a property such that the ratio (G2/G1) of the gas decomposition rate (G2) when visible light having only a wavelength of not less than 380 nm and an illuminance of 2500 lx is irradiated with respect to the gas decomposition rate (G1) when visible light having only a wavelength of not less than 380 nm and an illuminance of 6000 lx is irradiated is 74% or more, it becomes possible that the visible light responsive photocatalyst powder of the second embodiment exhibits practical gas decomposition performance also under an indoor environment and the like in which an illuminance is low. For instance, good gas decomposition performance can be realized under an illuminance of about 200 lx such as an illuminance in a living room where people enjoy gathering, a wash room and the like in a home. Further, it is possible to obtain gas decomposition performance within a practical range also under a significantly low illuminance of around 50 lx such as an illuminance on a ceiling, a wall, a floor, and in a place where a furniture, a home electric appliance and the like are disposed in the indoor.

Photocatalysis is an action in which electrons and positive holes excited by light activate a hydroxyl group and oxygen on a surface through oxidation-reduction, and reactive oxygen species generated by the activation perform oxidative decomposition on organic gas and the like. Therefore, generally, when the amount of light (number of photons) is decreased, namely, an illuminance is lowered, an amount of gas decomposition realized by a photocatalyst is also decreased in accordance therewith.

Meanwhile, the visible light responsive photocatalyst powder of the second embodiment exhibits not only an excellent gas decomposition rate (G1) under a significantly high illuminance such as an illuminance of 6000 lx, but also a high gas decomposition rate (G2) under the irradiation of visible light with an illuminance of 2500 lx, which is apparent from the G2/G1 ratio being 74% or more. As above, the visible light responsive photocatalyst powder of the second embodiment exhibits performance different from that of a conventional visible light responsive photocatalyst powder, and it suppresses the decrease in the photocatalytic activity in accordance with the decrease in the illuminance, so that it is possible to obtain practical gas decomposition performance under an illuminance of about 200 lx and even under a low illuminance of about 50 lx. Therefore, it becomes possible to obtain gas decomposition performance under an indoor environment such as a living room where people enjoy gathering, a toilet, a wash room and the like in which an illuminance is low, and also under an environment in which an illuminance is significantly low such as a ceiling, a wall, a floor, and a place where a furniture, a home electric appliance and the like are disposed in the indoor.

As described above, in order to obtain practical gas decomposition performance under a low illuminance such as 200 lx or less or even 50 lx or less, the visible light responsive photocatalyst powder preferably has a ratio (G3/G1) of a gas decomposition rate (G3) when irradiated with visible light having an illuminance of 1000 lx with respect to the gas decomposition rate (G1) under an illuminance of 6000 lx, which is 50% or more, and a ratio (G4/G1) of a gas decomposition rate (G4) when irradiated with visible light having an illuminance of 600 lx with respect to G1, which is 37% or more. By realizing such ratios of gas decomposition rates, the decrease in the photocatalytic activity in accordance with the decrease in the illuminance is further suppressed, which enables to obtain gas decomposition performance under a low illuminance in a more reproducible manner. It is supposed that the gas decomposition rate (G3) under an illuminance of 1000 lx and the gas decomposition rate (G4) under an illuminance of 600 lx are respectively measured by using the same amount of sample as that used for measuring the gas decomposition rate (G1) under an illuminance of 6000 lx.

Further, to exhibit the G2/G1 ratio of 74% or more means to exhibit excellent gas decomposition performance not only under an environment of significantly high illuminance such as an illuminance of 6000 lx but also under an environment of somewhat high illuminance of about 2500 lx such as right below an illumination from a fluorescent lamp or the like. To exhibit the G3/G1 ratio of 50% or more and further, to exhibit the G4/G1 ratio of 37% or more means to be able to obtain good gas decomposition performance in an office and under an environment where a delicate work is performed in which an illuminance is about 1000 lx, and also under an environment when reading books in which an illuminance is about 600 lx and the like. According to the visible light responsive photocatalyst powder of this embodiment, gas decomposition performance can be exhibited under various illuminances.

A ratio of the gas decomposition rate (G2) when visible light with an illuminance of 2500 lx is irradiated to the visible light responsive photocatalyst powder with respect to the gas decomposition rate (G1) under an illuminance of 6000 lx is preferably 88% or more. It is more preferable that a ratio of the gas decomposition rate (G3) when visible light having an illuminance of 1000 lx is irradiated with respect to the gas decomposition rate (G1) under an illuminance of 6000 lx is 66% or more, and a ratio of the gas decomposition rate (G4) when visible light having an illuminance of 600 lx is irradiated with respect to G1 is 48% or more. With the use of a visible light responsive photocatalyst powder as described above, it is possible to realize excellent gas decomposition performance under an illuminance of about 200 lx, and further, it is possible to obtain good gas decomposition performance under a low illuminance of around 50 lx such as an illuminance on a wall, and in a place where a furniture, a home electric appliance and the like are disposed in the indoor. Further, the gas decomposition performance can be exhibited also under an environment of significantly low illuminance of about 10 lx.

The visible light responsive photocatalyst powder having the ratios of gas decomposition rates as described above can be obtained by controlling a particle size (specific surface area), a crystal structure, a crystallinity, a powder color and the like of a tungsten oxide powder or a tungsten oxide composite material powder (tungsten oxide type powder) that forms the visible light responsive photocatalyst powder. Here, the tungsten oxide composite material powder is formed by making tungsten oxide as a main component contain at least one metal element selected from Ti, Fe, Cu, Zr, Ag, Pt, Pd, Mn, Al and Ce in a range of 50 mass % or less, for instance. A concrete structure (a form of composition, an amount of composition, and so on), a composite method and the like of the tungsten oxide composite material powder are the same as those of the first embodiment.

The tungsten oxide type powder that forms the visible light responsive photocatalyst powder of the second embodiment preferably has a BET specific surface area in a range of 4.1 to 820 $m^2/g$. Further, the tungsten oxide type powder preferably has an average particle size in a range of 1 to 200 nm. Here, it is assumed that the average particle size is determined based on an average particle size of particles in number n=50 or more (D50) by image analysis of a photograph of SEM, TEM, or the like. The average particle size (D50) may be equal to the average particle size converted from the specific surface area.

The larger the specific surface area and the smaller the particle size, the higher the performance of the photocatalyst powder. Therefore, when the BET specific surface area of the tungsten oxide powder is less than 4.1 $m^2/g$ or when the average particle size is greater than 200 nm, sufficient photocatalytic performance cannot be obtained. Meanwhile, when the BET specific surface area of the tungsten oxide type powder is over 820 $m^2/g$ or when the average particle size is less than 1 nm, the particle becomes too small, and practicability is lowered because handlability as powder deteriorates. The BET specific surface area of the tungsten oxide type powder is preferably in a range of 8.2 to 410 $m^2/g$, and the average particle size is preferably in a range of 2 to 100 nm.

The BET specific surface area of the tungsten oxide type powder is preferably in a range of 11 to 300 $m^2/g$, and more preferably, in a range of 16 to 150 $m^2/g$. The average particle size is preferably in a range of 2.7 to 75 nm, and more preferably, in a range of 5.5 to 51 nm. When the tungsten oxide type powder is applied to a visible light responsive photocatalyst coating material or the like, too small a particle size results in poor dispersibility of particles and results in a difficulty in turning it into the coating material. To solve such problems, a tungsten oxide type powder whose average particle size is 5.5 nm or more is preferably used.

It is preferable that tungsten oxide that forms the tungsten oxide powder or the tungsten oxide composite material powder in the second embodiment has a crystal structure of at least one selected from a monoclinic crystal and a triclinic crystal of tungsten trioxide, or a crystal structure in which a rhombic crystal is mixed with at least one selected from the monoclinic crystal and the triclinic crystal. The tungsten oxide powder as described above can stably exhibit excellent photocatalytic performance. Though it is difficult to determine abundance ratios of the respective crystal phases of tungsten trioxide, it can be estimated that a powder has the above-described crystal structure when it satisfies the aforementioned conditions (1) to (4) when measured by X-ray diffractometry.

Further, the tungsten oxide type powder preferably has color whose $a^*$ is −5 or less, $b^*$ is 5 or more, and $L^*$ is 70 or more when the color of the powder is expressed by the $L^*a^*b^*$ color system (L-star/a-star/b-star color system). The tungsten oxide type powder preferably has color whose $a^*$ is −5 or less, $*b$ is 5 or more, and $L^*$ is 70 or more, and more preferably has color whose $a^*$ is in a range of −25 to −8, $b^*$ is in a range of 10 to 45, and $L^*$ is 85 or more. Such numerical values of the $L^*a^*b^*$ color system indicate that the tungsten oxide type powder has a hue from yellow to the vicinity of green and has high saturation and lightness.

When the tungsten oxide type powder has such an optical property, its photocatalytic performance by visible light excitation can be improved. The color tone of the tungsten oxide powder is thought to change based on composition fluctuation due to oxygen deficiency or the like, light irradiation, and so on, and when the powder has the above-described hue, saturation, and lightness, good photocatalytic performance can be obtained. When the powder has a hue close to blue, it is thought that there is a high degree of oxygen deficiency or the like, and with such a hue, the deterioration in the photocatalytic performance is observed.

By using the tungsten oxide type powder having the particle size (specific surface area), the crystal structure, the powder color and the like as described above and further having an improved crystallinity, it is possible to realize a visible light responsive photocatalyst powder, in a more reproducible manner, which exhibits the ratio of the gas decomposition rate (G2) when irradiated with visible light having an illuminance of 2500 lx with respect to the gas decomposition rate (G1) when irradiated with visible light having an illuminance of 6000 lx, which is 74% or more, and further, the ratio of the gas decomposition rate (G3) when irradiated with visible light having an illuminance of 1000 lx with respect to G1, which is 50% or more, and the ratio of the gas decomposition rate (G4) when irradiated with visible light having an illuminance of 600 lx with respect to G1, which is 37% or more. Here, the performance of the visible light responsive photocatalyst powder cannot be improved only by the specific surface area and the particle size.

As described above, when titanium oxide is employed, it is possible to improve a visible light responsiveness by increasing absorbing performance of visible light by doping nitrogen or sulfur in the titanium oxide. Further, by improving a crystallinity by controlling a heat treatment temperature or by making the titanium oxide support a metal, it becomes possible to increase the photocatalytic activity by preventing the re-combination of electrons and positive holes. However, although there currently exists titanium oxide that exhibits high performance under a significantly high illuminance, since the performance is deteriorated in accordance with the decrease in the illuminance, no practical gas decomposition performance is not obtained under a low illuminance of about 150 to 500 lx being a common level.

On the contrary, by applying the tungsten oxide type powder having absorbing performance of visible light to the visible light responsive photocatalyst powder in which the BET specific surface area and the average particle size (D50), the crystal structure, the powder color and the like of the tungsten oxide type powder are controlled as described above and besides, the crystallinity of the tungsten oxide type powder is improved, it becomes possible to realize a property such that the ratio of the gas decomposition rate under an illuminance of 6000 lx and the gas decomposition rate under an illuminance of 2500 lx (G2/G1 ratio) is 74% or more. This is because of combined effects such that a gas absorption amount is increased by enlarging the specific surface area of the photocatalyst powder, activated sites can be accordingly increased, and a probability of the occurrence of re-combination is decreased because of the improved crystallinity.

Tungsten oxide has a band gap of 2.5 to 2.8 eV, which is smaller than that of titanium oxide, and accordingly, it absorbs visible light. Therefore, it is possible to realize an excellent visible light responsiveness. Further, since a typical crystal structure of tungsten oxide is $ReO_3$ structure, a crystal plane having oxygen on an outermost layer of its surface and having a high reaction activity is likely to be exposed. For this reason, tungsten oxide exhibits a high hydrophilic property by absorbing water. Alternatively, an OH radical is generated by oxidizing the absorbed water, which enables to oxidize a molecule and a compound, so that it becomes possible that the photocatalytic performance which is better than that provided by an anatase or rutile crystal of titanium oxide is exhibited. Besides, the tungsten oxide powder of this embodiment is excellent in dispersibility since its zeta potential in an aqueous solution with pH 1 to 7 is minus, and thus can be applied thinly and evenly on a base material and the like.

Examples of the photocatalytic performance are performance of decomposing organic gas such as acetaldehyde and formaldehyde, a hydrophilic property, antibacterial performance, and disinfection performance. The visible light responsive photocatalyst powder of this embodiment has excellent photocatalytic performance when irradiated with 430 to 500 nm light. Examples of an excitation source emitting light with a 430 to 500 nm wavelength are sunlight, a fluorescent lamp, a blue-emitting diode, a blue laser, and the like. In particular, the blue-emitting diode and the blue laser are preferable since they can emit only light with a 430 to 500 nm wavelength.

The tungsten oxide type powder that forms the visible light responsive photocatalyst powder may contain a trace amount of metal element as impurities. The content of the metal element as the impurity element is preferably 2 mass % or less. Examples of the impurity metal element are an element normally contained in a tungsten mineral and a contaminant element which is mixed when a tungsten compound or the like used as a raw material is produced, and examples thereof are Fe, Mo, Mn, Cu, Ti, Al, Ca, Ni, Cr, Mg, and the like, for instance. It is not limited to the above examples when these elements are used as constituent elements of a composite material.

Next, a visible light responsive photocatalyst powder according to a third embodiment will be described. The visible light responsive photocatalyst powder according to the third embodiment includes a tungsten oxide powder or a tungsten oxide composite material powder. Such a visible light responsive photocatalyst powder exhibits a gas decomposition rate of 5% or more, in a gas decomposition test to be described hereinbelow, when visible light having only a wavelength of not less than 380 nm and an illuminance of 200 lx is irradiated. Further, it is preferable that the visible light responsive photocatalyst powder has a gas decomposition rate of 2% or more when visible light having only a wavelength of not less than 380 nm and an illuminance of 100 lx is irradiated, and a gas decomposition rate of 1% or more when visible light having only a wavelength of not less than 380 nm and an illuminance of 50 lx is irradiated.

The gas decomposition test for determining the aforementioned gas decomposition rates is conducted by using a flow-type apparatus as is used in the evaluation of nitrogen oxide removal performance (decomposition performance) of JIS-R-1701-1 (2004). The gas concentrations are measured by allowing an acetaldehyde gas having an initial concentration of 10 ppm to flow into the flow-type apparatus in which 0.2 g of a sample is placed.

In such gas concentrations, a gas concentration before light irradiation is set as A, and a gas concentration when not less than 15 minutes have elapsed from the light irradiation and, at the same time, the gas concentration is stable, is set as B. Subsequently, from the gas concentration A and the gas concentration B, a value calculated based on [formula: $(A-B)/A \times 100$] is set as the gas decomposition rate (%).

Generally, visible light corresponds to light whose wavelength is in a range of 380 to 830 nm. In order to evaluate further excellent performance under visible light similar to that under an actual usage environment, it is assumed that visible light having only a wavelength of not less than 380 nm is used in an evaluation of this embodiment. Concretely, it is preferable to perform the evaluation by irradiating visible light having only a wavelength of not less than 380 nm by using a white fluorescent lamp defined in JIS-Z-9112 as a light source and an ultraviolet cutoff filter cutting off light whose wavelength is less than 380 mm. As the white fluorescent lamp, for instance, FL20SS•W/18 manufactured by Toshiba Lighting & Technology Corporation or an equivalent thereof is used. As the ultraviolet cutoff filter, Clarex N-169 (product name) manufactured by Nitto Jushi Kogyo Co., Ltd., or an equivalent thereof is used.

In the indoor where the visible light responsive photocatalyst is mainly used, excitation light is light from illumination lamps and natural light from windows, but, excitation light in a place in a living space where an illuminance is low is often only light from illumination lamps. The most generally used illumination light source in the indoor is a white fluorescent lamp, so that the performance measurement of the visible light responsive photocatalyst powder of this embodiment is assumed to be performed by using the white fluorescent lamp. This enables to obtain a value closest to that of practical performance. Similar to the first embodiment, the visible light responsive photocatalyst powder of the third embodiment exhibits a similar gas decomposition rate also when visible light having only a wavelength of not less than 410 nm is irradiated using a white LED lamp.

As described above, since the visible light responsive photocatalyst powder of the third embodiment exhibits a good gas decomposition rate under the irradiation of visible light with an illuminance of 200 lx, and also under the irradiation of visible light with an illuminance of 100 lx and under the irradiation of visible light with an illuminance of 50 lx, it becomes possible to obtain photocatalytic performance in an indoor environment and the like in which an illuminance is low. Specifically, even under an illuminance of about 200 lx such as an illuminance in a living room where people enjoy gathering, a wash room and the like in a home, it is possible to obtain good photocatalytic performance based on the gas decomposition rate of 5% or more, and it becomes possible to provide a visible light responsive photocatalyst powder having a higher sensitivity than ever. Further, it is possible to obtain practical photocatalytic performance even under a significantly low illuminance of about 100 lx to 50 lx such as an illuminance on a ceiling, a wall, a floor, and in a place where a furniture, a home electric appliance and the like are disposed in the indoor, based on the gas decomposition rate of 2% or more (irradiation under 100 lx) or 1% or more (irradiation under 50 lx).

It goes without saying that the visible light responsive photocatalyst powder of the third embodiment exhibits high photocatalytic performance under a significantly high illuminance such as 6000 lx which is widely applied for the evaluation thereof. Further, the powder exhibits excellent photocatalytic performance under an environment having an illuminance of about 1000 lx such as an office and a place where a delicate work is performed and also under an indoor environment with a common brightness of about 600 lx such as when reading books. As above, with the use of the visible light responsive photocatalyst powder of the third embodiment, it becomes possible that the photocatalytic performance is exhibited under various illuminances.

A gas decomposition rate when visible light with an illuminance of 200 lx is irradiated to the visible light responsive photocatalyst powder is preferably 15% or more. Further, it is more preferable that a gas decomposition rate when visible light having an illuminance of 100 lx is irradiated is 10% or more, and a gas decomposition rate when visible light having an illuminance of 50 lx is irradiated is 5% or more. With the use of a visible light responsive photocatalyst powder satisfying such conditions, it is possible to obtain excellent photocatalytic performance under an indoor environment such as a living room where people enjoy gathering and a wash room in a home. Further, it is possible to obtain good photocatalytic performance also under a significantly low illuminance such as an illuminance on a ceiling, a wall, a floor, and in a place where a furniture, a home electric appliance and the like are disposed in the indoor. Further, in the third embodiment, the photocatalytic performance can be achieved even by little light with an illuminance of 10 lx or the like, and thus it becomes possible to provide a visible light responsive photocatalyst powder having a property that never existed before.

The visible light responsive photocatalyst powder having the gas decomposition rates as described above can be obtained by controlling a particle size (specific surface area), a crystal structure, a crystallinity, a powder color and the like of a tungsten oxide powder or a tungsten oxide composite material powder (tungsten oxide type powder) that forms the visible light responsive photocatalyst powder. Here, the tungsten oxide composite material powder is formed by making tungsten oxide as a main component contain at least one metal element selected from Ti, Fe, Cu, Zr, Ag, Pt, Pd, Mn, Al and Ce in a range of 50 mass % or less, for instance. A concrete structure (a form of composition, an amount of composition, and so on), a composite method and the like of the tungsten oxide composite material powder are the same as those of the first embodiment.

The tungsten oxide type powder that forms the visible light responsive photocatalyst powder of the third embodiment preferably has a BET specific surface area in a range of 4.1 to 820 $m^2/g$. Further, the tungsten oxide type powder preferably has an average particle size in a range of 1 to 200 nm. Here, it is assumed that the average particle size is determined based on an average particle size of particles in number n=50 or more (D50) by image analysis of a photograph of SEM, TEM, or the like. The average particle size (D50) may be equal to the average particle size converted from the specific surface area.

The larger the specific surface area and the smaller the particle size, the higher the performance of the photocatalyst powder. Therefore, when the BET specific surface area of the tungsten oxide type powder is less than 4.1 $m^2/g$ or when the average particle size is greater than 200 nm, sufficient photocatalytic performance cannot be obtained. Meanwhile, when the BET specific surface area of the tungsten oxide type powder is over 820 $m^2/g$ or when the average particle size is less than 1 nm, the particle becomes too small, and practicability is lowered because handlability as powder deteriorates. The BET specific surface area of the tungsten oxide type powder is preferably in a range of 8.2 to 420 $m^2/g$, and the average particle size is preferably in a range of 2 to 100 nm.

The BET specific surface area of the tungsten oxide type powder is preferably in a range of 11 to 300 $m^2/g$, and more preferably, in a range of 16 to 150 $m^2/g$. The average particle size is preferably in a range of 2.7 to 75 nm, and more preferably, in a range of 5.5 to 51 nm. When the tungsten oxide type powder is applied to a visible light responsive photocatalyst coating material or the like, too small a particle size results in poor dispersibility of particles and results in a difficulty in turning it into the coating material. To solve such problems, a tungsten oxide type powder whose average particle size is 5.5 nm or more is preferably used.

It is preferable that tungsten oxide that forms the tungsten oxide powder or the tungsten oxide composite material powder in the third embodiment has a crystal structure of at least one selected from a monoclinic crystal and a triclinic crystal of tungsten trioxide, or a crystal structure in which a rhombic crystal is mixed with at least one selected from the monoclinic crystal and the triclinic crystal. The tungsten oxide powder as described above can stably exhibit excellent photocatalytic performance. Though it is difficult to determine abundance ratios of the respective crystal phases of tungsten trioxide, it can be estimated that a powder has the above-described crystal structure when it satisfies the aforementioned conditions (1) to (4) when measured by X-ray diffractometry.

Further, the tungsten oxide type powder preferably has color whose a* is −5 or less, b* is 5 or more, and L* is 70 or more when the color of the powder is expressed by the L*a*b* color system (L-star/a-star/b-star color system). The tungsten oxide type powder preferably has color whose a* is −5 or less, *b is 5 or more, and L* is 70 or more, and more preferably has color whose a* is in a range of −25 to −8, b* is in a range of 10 to 45, and L* is 85 or more. Such numerical values of the L*a*b* color system indicate that the tungsten oxide powder has a hue from yellow to the vicinity of green and has high saturation and lightness.

When the tungsten oxide type powder has such an optical property, its photocatalytic performance by visible light excitation can be improved. The color tone of the tungsten oxide powder is thought to change based on composition fluctuation due to oxygen deficiency or the like, light irradiation, and so on, and when the powder has the above-described hue, saturation, and lightness, good photocatalytic performance can be obtained. When the powder has a hue close to blue, it is thought that there is a high degree of oxygen deficiency or the like, and with such a hue, the deterioration in the photocatalytic performance is observed.

By using the tungsten oxide type powder having the particle size (specific surface area), the crystal structure, the powder color and the like as described above and further having an improved crystallinity, it is possible to obtain a visible light responsive photocatalyst powder which exhibits the gas decomposition rate of 5% or more when irradiated with visible light having an illuminance of 200 lx, and further, the gas decomposition rate of 2% or more when irradiated with visible light having an illuminance of 100 lx, and the gas decomposition rate of 1% or more when irradiated with visible light having an illuminance of 50 lx. Here, the performance of the visible light responsive photocatalyst powder cannot be improved only by the specific surface area and the particle size.

As described above, when titanium oxide is employed, it is possible to improve a visible light responsiveness by increasing absorbing performance of visible light by doping nitrogen or sulfur in the titanium oxide. Further, by improving a crystallinity by controlling a heat treatment temperature or by making the titanium oxide support a metal, it becomes possible to increase the photocatalytic activity by preventing the re-combination of electrons and positive holes. However, although there currently exist titanium oxide that exhibits high performance under a significantly high illuminance, since the performance is deteriorated in accordance with the decrease in the illuminance, there is no titanium oxide that exhibits practical photocatalytic performance under a low illuminance of about 150 to 500 lx being a common level. Further, there is no titanium oxide that exhibits activity under little light with an illuminance of about 10 lx.

On the contrary, by applying the tungsten oxide type powder having absorbing performance of visible light to the visible light responsive photocatalyst powder in which the BET specific surface area and the average particle size (D50) and further, the crystal structure, the powder color and the like of the tungsten oxide type powder are controlled as described above and besides, the crystallinity of the tungsten oxide type powder is improved, it becomes possible to realize the gas decomposition rate of 5% or more under an illuminance of 200 lx. This is because of combined effects such that a gas absorption amount is increased by enlarging the specific surface area of the photocatalyst powder, activated sites can be accordingly increased, and a probability of the occurrence of re-combination is decreased because of the improved crystallinity.

Tungsten oxide has a band gap of 2.5 to 2.8 eV, which is smaller than that of titanium oxide, and accordingly, it absorbs visible light. Therefore, it is possible to realize an excellent visible light responsiveness. Further, since a typical crystal structure of tungsten oxide is $ReO_3$ structure, a crystal plane having oxygen on an outermost layer of its surface and having a high reaction activity is likely to be exposed. For this reason, tungsten oxide exhibits a high hydrophilic property by absorbing water. Alternatively, an OH radical is generated by oxidizing the absorbed water, which enables to oxidize a molecule and a compound, so that it becomes possible that the photocatalytic performance which is better than that provided by an anatase or rutile crystal of titanium oxide is exhibited. Besides, the tungsten oxide powder of this embodiment is excellent in dispersibility since its zeta potential in an aqueous solution with pH 1 to 7 is minus, and thus can be applied thinly and evenly on a base material and the like.

Examples of the photocatalytic performance are performance of decomposing organic gas such as acetaldehyde and formaldehyde, a hydrophilic property, antibacterial performance, and disinfection performance. The visible light responsive photocatalyst powder of this embodiment has excellent photocatalytic performance when irradiated with 430 to 500 nm light. Examples of an excitation source emitting light with a 430 to 500 nm wavelength are sunlight, a fluorescent lamp, a blue-emitting diode, a blue laser, and the like. In particular, the blue-emitting diode and the blue laser are preferable since they can emit only light with a 430 to 500 nm wavelength.

The tungsten oxide type powder that forms the visible light responsive photocatalyst powder may contain a trace amount of metal element as impurities. The content of the metal element as the impurity element is preferably 2 mass % or less. Examples of the impurity metal element are an element normally contained in a tungsten mineral and a contaminant element which is mixed when a tungsten compound or the like used as a raw material is produced, and examples thereof are Fe, Mo, Mn, Cu, Ti, Al, Ca, Ni, Cr, Mg, and the like, for instance. It is not limited to the above examples when these elements are used as constituent elements of a composite material.

The tungsten oxide powder that forms the visible light responsive photocatalyst powder according to the embodiment is manufactured as follows, for instance. The tungsten oxide powder is manufactured by the use of a sublimation process. Further, combining a heat treatment process with the sublimation process is also effective. According to the tungsten trioxide powder manufactured by the use of the sublimation process or the combination of the sublimation process and the heat treatment process, it is possible to stably realize the aforesaid crystal structure and BET specific surface area. Further, when the powder is evaluated by SEM or TEM, the average particle size of primary particles approximates a value converted from the BET specific surface area, and it is possible to stably provide a powder small in particle size variation.

First, the sublimation process will be described. The sublimation process is a process to obtain a tungsten trioxide powder by sublimating a metal tungsten powder, a tungsten compound powder, or a tungsten compound solution in an oxygen atmosphere. Sublimation is a phenomenon in which a state change from a solid phase to a vapor phase or from a vapor phase to a solid phase occurs not through a liquid phase. By oxidizing the metal tungsten powder, the tungsten compound powder, or the tungsten compound solution as a raw material while sublimating it, it is possible to obtain a tungsten oxide powder in a fine powder state.

As the raw material of the sublimation process (tungsten raw material), any of the metal tungsten powder, the tungsten compound powder, and the tungsten compound solution may be used. Examples of the tungsten compound used as the raw material are tungsten trioxide ($WO_3$), tungsten dioxide ($WO_2$), tungsten oxide such as low-grade oxide, tungsten carbide, ammonium tungstate, calcium tungstate, tungstic acid, and the like.

By the sublimation process of the above-described tungsten raw material in the oxygen atmosphere, the metal tungsten powder or the tungsten compound powder is instantaneously changed from a solid phase to a vapor phase, and oxidizing metal tungsten vapor changed to the vapor phase results in a tungsten oxide powder. When a solution is used, it also changes to a vapor phase through a tungsten oxide or compound. By thus using an oxidation reaction in the vapor phase, it is possible to obtain a tungsten oxide fine powder. Further, the crystal structure of the tungsten oxide fine powder can be controlled.

As the raw material of the sublimation process, it is preferable to use at least one selected from a metal tungsten powder, a tungsten oxide powder, a tungsten carbide powder, and an ammonium tungstate powder since the tungsten oxide powder obtained by the sublimation in the oxygen atmosphere is less likely to contain impurities. The metal tungsten powder and the tungsten oxide powder are especially preferable as the raw material of the sublimation process since they do not contain a toxic substance as a byproduct (substance other than tungsten oxide) produced in the sublimation process.

As the tungsten compound used as the raw material, a compound containing tungsten (W) and oxygen (O) as its constituent elements is preferable. The tungsten compound containing W and O as its constituent components is easily sublimated instantaneously when a later-described inductively-coupled plasma process or the like is applied in the sublimation process. Examples of such a tungsten compound are $WO_3$, $W_{20}O_{58}$, $W_{18}O_{49}$, $WO_2$, and the like. Further, solutions, salts, or the like of tungstic acid, ammonium paratungstate, ammonium metatungstate are also effective.

The metal tungsten powder or the tungsten compound powder as the tungsten raw material preferably has an average particle size in a range of 0.1 to 100 μm. The average particle size of the tungsten raw material more preferably falls within a range of 0.3 μm to 10 μm, still more preferably, within a range of 0.3 μm to 3 μm, and desirably within a range of 0.3 μm to 1.5 μm. When the metal tungsten powder or the tungsten compound powder having the average particle size in the above range is used, the sublimation easily occurs.

When the average particle size of the tungsten raw material is less than 0.1 μm, the raw material powder is too fine, and thus advance adjustment of the raw material powder is required and handlability is lowered, and in addition, high cost is required, which is not industrially preferable. When the average particle size of the tungsten raw material is over 100 μm, a uniform sublimation reaction is difficult to occur. Even if the average particle size is large, processing with a large energy amount can cause a uniform sublimation reaction, but this is not industrially preferable.

As a method of sublimating the tungsten raw material in the oxygen atmosphere in the sublimation process, at least one of process selected from an inductively-coupled plasma process, an arc discharge process, a laser process, an electron beam process, and a gas burner process is possible. Among them, in the laser process and the electron beam process, the sublimation process is performed by the irradiation of a laser or an electron beam. Since the laser and the electron beam have a small irradiation spot diameter, they need a long time to process a large amount of the raw material at a time, but have an advantage that there is no need to strictly control the particle size of the raw material powder and stability of its supply amount.

The inductively-coupled plasma process and the arc discharge process can cause an oxidation reaction of a large amount of the raw material powder at a time in an oxygen atmosphere though requiring the adjustment of a generation area of plasma or arc discharge. Moreover, an amount of the raw material processable at a time can be controlled. The gas burner process has a difficulty in processing a large amount of the raw material powder or the raw material solution though requiring a small motive power expense. Therefore, the gas burner process is inferior in productivity. Note that a gas burner may be any having an energy high enough to cause the sublimation, and is not particularly limited. A propane gas burner, an acetylene gas burner, or the like is used.

When the inductively-coupled plasma process is applied to the sublimation process, a generally used method is a method in which plasma is generated by using argon gas or oxygen gas and a metal tungsten powder or a tungsten compound powder is supplied to the plasma. A method of supplying the tungsten raw material into the plasma is, for example, a method of injecting a metal tungsten powder or a tungsten compound powder together with carrier gas, a method of injecting a dispersion liquid in which the metal tungsten powder or the tungsten compound powder is dispersed in a predetermined liquid dispersion medium, or the like.

The carrier gas used when the metal tungsten powder or the tungsten compound powder is injected into the plasma is, for example, air, oxygen, inert gas containing oxygen, or the like. Among them, air is preferably used because of its low cost. When a reaction field contains a sufficient amount of oxygen such as a case where reaction gas containing oxygen is injected besides the carrier gas or a case where the tungsten compound powder is tungsten trioxide, inert gas such as argon or helium may be used as the carrier gas. As the reaction gas, the use of oxygen or inert gas containing oxygen is preferable. When the inert gas containing oxygen is used, an oxygen amount is preferably set so that a sufficient amount of oxygen necessary for the oxidation reaction can be supplied.

Applying the method of injecting the metal tungsten powder or the tungsten compound powder with the carrier gas and adjusting a gas flow rate, the pressure in a reaction vessel and the like facilitate the control of the crystal structure of the tungsten trioxide powder. Concretely, it is easy to obtain the tungsten trioxide powder having a crystal structure of at least one selected from the monoclinic crystal and the triclinic crystal (the monoclinic crystal, the triclinic crystal, or the mixed crystal of the monoclinic crystal and the triclinic crystal) or a crystal structure in which the rhombic crystal is mixed with the selected crystal. The crystal structure of the tungsten trioxide powder is more preferably the mixed crystal of the monoclinic crystal and the triclinic crystal, or the mixed crystal of the monoclinic crystal, the triclinic crystal and the rhombic crystal.

The dispersion medium used in the preparation of the dispersion liquid of the metal tungsten powder or the tungsten compound powder is a liquid dispersion medium having oxygen atoms in its molecules, or the like. Using the dispersion liquid facilitates handling of the raw material powder. As the liquid dispersion medium having oxygen atoms in its molecules, that containing 20 vol. % or more of at least one selected from water and alcohol is used, for instance. As alcohol used as the liquid dispersion medium, at least one selected from methanol, ethanol, 1-propanol, and 2-propanol is preferable, for instance. Water and alcohol do not obstruct the sublimation reaction and the oxidation reaction of the raw material powder because of their easy volatility by heat of plasma, and easily promote the oxidation reaction because they contain oxygen in its molecules.

When the dispersion liquid is prepared by dispersing the metal tungsten powder or the tungsten compound powder in the dispersion medium, it is preferable that the dispersion liquid contains the metal tungsten powder or the tungsten compound powder whose content falls within a range of 10 to 95 mass %, and more preferably, within a range of 40 to 80 mass %. By setting the dispersion amount in the dispersion liquid to such a range, it is possible to uniformly disperse the metal tungsten powder or the tungsten compound powder in the dispersion liquid. The uniform dispersion facilitates the uniform occurrence of the sublimation reaction of the raw material powder. If the content in the dispersion liquid is less than 10 mass %, an amount of the raw material powder is too small and efficient manufacture is not possible. If the content is over 95 mass %, the raw material powder has an increased viscosity due to a small amount of the dispersion liquid and thus easily sticks to the vessel, which lowers handlability.

Applying the method of dispersing the metal tungsten powder or the tungsten compound powder in the dispersion liquid and injecting the dispersion liquid into the plasma facilitates controlling the crystal structure of the tungsten trioxide powder. Concretely, it is easy to obtain the tungsten trioxide powder having a crystal structure of at least one selected from the monoclinic crystal and the triclinic crystal, or a crystal structure in which the rhombic crystal is mixed with the selected crystal. Further, using the tungsten compound solution as the raw material also enables a uniform sublimation reaction and improves controllability of the crystal structure of the tungsten trioxide powder. The method of using the dispersion liquid as described above is also applicable to the arc discharge process.

When the sublimation process is performed by the irradiation of a laser or an electron beam, it is preferable to use the metal tungsten or the tungsten compound in a pellet form as the raw material. Since the laser and the electron beam have a small irradiation spot diameter, the use of the metal tungsten powder or the tungsten compound powder makes the supply difficult, but, using the metal tungsten or tungsten compound in a pellet form enables efficient sublimation. The laser may be any having an energy high enough to sublimate the metal tungsten or the tungsten compound and is not particularly limited, but, a $CO_2$ laser is preferable because of its high energy.

When the pellet is irradiated with the laser or the electron beam, moving at least one of an irradiation source of the laser beam or the electron beam and the pellet enables effective sublimation of the whole surface of the pellet having a certain degree of size. This makes it easy to obtain the tungsten trioxide powder having the crystal structure in which the rhombic crystal is mixed with at least one selected from the monoclinic crystal and the triclinic crystal. The pellet as described above is also applicable to the inductively-coupled plasma process and the arc discharge process.

The tungsten oxide powder that forms the visible light responsive photocatalyst powder of the embodiment can be obtained only by the sublimation process as described above, but, it is also effective to subject the tungsten oxide powder produced by the sublimation process to a heat treatment process. In the heat treatment process, the tungsten trioxide powder obtained by the sublimation process is heat-treated in an oxide atmosphere at a predetermined temperature and for a predetermined time. Even when a sufficient amount of the tungsten trioxide fine powder cannot be formed by controlling the conditions of the sublimation process and the like, performing the heat treatment makes it possible to make a ratio of the tungsten trioxide fine powder in the tungsten oxide powder 99% or more, or practically 100%. Further, the heat treatment process can adjust the crystal structure of the tungsten trioxide fine powder to a predetermined structure.

Examples of the oxide atmosphere used in the heat treatment process are air and oxygen-containing gas. The oxygen-containing gas means inert gas containing oxygen. The heat treatment temperature is preferably set in a range of 200 to 1000° C., and is more preferably from 400 to 700° C. The heat treatment time is preferably 10 minutes to 5 hours, and more preferably 30 minutes to 2 hours. Making the temperature and the time of the heat treatment process fall within the aforesaid ranges facilitates forming tungsten trioxide from tungsten oxide except tungsten trioxide. Further, in order to obtain a powder having a good crystallinity with little defect, it is preferable to gradually increase or decrease the temperature at the time of heat treatment. Rapid heating or cooling at the time of heat treatment causes a decrease in the crystallinity.

When the heat treatment temperature is lower than 200° C., there is a possibility that it is not possible to obtain a sufficient oxidation effect for turning the powder, which has not been turned into tungsten trioxide in the sublimation process, into tungsten trioxide. When the heat treatment temperature is higher than 1000° C., the tungsten oxide fine particles rapidly grow and accordingly the specific surface area of the resultant tungsten oxide fine powder is likely to decrease. Further, by performing the heat treatment process at the aforesaid temperature and for the aforesaid time, it becomes possible to adjust the crystal structure and the crystallinity of the tungsten trioxide fine powder.

In order to improve photocatalytic performance and a product property, for example, gas decomposition performance or antibacterial performance, the tungsten oxide powder may contain a transition metal element. The content of the transition metal element is preferably 50 mass % or less. When the content of the transition metal element is over 50 mass %, the property as the visible light responsive photocatalyst powder may possibly deteriorate. The content of the transition metal element is preferably 10 mass % or less, and more preferably 2 mass % or less. The transition metal element is any of elements whose atomic numbers are 21 to 29, 39 to 47, 57 to 79, and 89 to 109, and among them, the use of at least one selected from Ti, Fe, Cu, Zr, Ag, and Pt is preferable. Examples of a form of the contained transition metal element are a metal, an oxide, a composite oxide, a compound, and the like, and the transition metal element may be mixed with the tungsten oxide powder, or the transition metal element may support the tungsten oxide powder. Further, the transition metal element with tungsten may form a compound.

The visible light responsive photocatalyst powder according to the embodiment is usable as a visible light responsive photocatalyst as it is, or a powder (or substance in a form other than powder) obtained by mixing the visible light responsive photocatalyst powder with another material or by having the other material support it, or by impregnating the other material with it can be used as the visible light responsive photocatalyst. A visible light responsive photocatalyst material of this embodiment contains the visible light responsive photocatalyst powder whose content falls within a range of 1 to 100 mass %. The content of the visible light responsive photocatalyst powder is appropriately selected according to a desired property, but, if it is less than 1 mass %, sufficient photocatalytic performance cannot be obtained. The visible light responsive photocatalyst powder may be mixed with particles of $SiO_2$, $ZrO_2$, $Al_2O_3$, $TiO_2$, or the like, for instance, or may be supported by these particles. Further, zeolite or the like may be impregnated with tungsten oxide or the tungsten oxide composite material.

The visible light responsive photocatalyst powder according to the embodiment mixed with a solvent, an additive, or the like is used as a visible light responsive photocatalyst coating material. As a main component of the visible light responsive photocatalyst coating material, the above-described visible light responsive photocatalyst material may be used instead of the visible light responsive photocatalyst powder. The content of the photocatalyst powder or the photocatalyst material in the visible light responsive photocatalyst coating material is set so as to fall within a range of 0.1 to 90 mass %. When the content of the photocatalyst powder or the photocatalyst material is less than 0.1 mass %, sufficient photocatalytic performance cannot be obtained, and when it is over 90 mass %, the property as the coating material lowers.

The solvent or the additive blended in the visible light responsive photocatalyst coating material is water, alcohol, a dispersing agent, a binder, or the like. The binder may be any of an inorganic binder, an organic binder, and an organic-inorganic composite binder. The inorganic binder is, for example, colloidal silica, alumina sol, zirconia sol, or the like. The organic-inorganic composite binder means an organic matter containing a metal element such as Si as its constituent component. As an organic component of the organic binder or the organic-inorganic composite binder, silicone resin or the like is used.

A visible light responsive photocatalyst product according to an embodiment includes the visible light responsive photocatalyst powder or photocatalyst material described above. Alternatively, the photocatalyst product includes a coating layer of the photocatalyst coating material. The photocatalyst product is, for example, a product in which the photocatalyst powder or the photocatalyst material is made to adhere to a base material or the base material is impregnated therewith, a product in which the photocatalyst coating material is applied on the base material, or the like. The photocatalyst products include products containing zeolite, activated carbon, porous ceramics, or the like impregnated with the photocatalyst powder.

Concrete examples of the visible light responsive photocatalyst product include an air-conditioner, an air cleaner, an electric fan, a refrigerator, a microwave oven, a dish washer/drier, a rice cooker, a pot, an IH heater, a washing machine, a vacuum cleaner, a lighting fixture (lamp, fixture main body, shade, or the like) sanitary goods, a lavatory bowl, a wash basin, a mirror, a bathroom (wall, ceiling, floor, and so on), building materials (indoor wall, ceiling material, floor, exterior wall), interior goods (curtain, carpet, table, chair, sofa, shelf, bed, bedding, and the like), glass, metal sash window, handrail, door, knob, clothes, filter used in home electric appliances, and the like. Further, examples of the base material of the visible light responsive photocatalyst product are glass, plastic, resin such as acryl, paper, fiber, metal, and wood. In particular, when the photocatalyst coating material is applied on glass, highly transparent glass is obtained.

The visible light responsive photocatalyst product according to the embodiment can be used as parts used in living space and in indoor space of automobiles. Since a high-sensitive photocatalyst is employed, the photocatalytic performance can be exhibited also in a place in the indoor where light is difficult to be applied, or a place with a low luminance. Further, since automobiles use glass transmitting almost no ultraviolet, by using the visible light responsive photocatalyst product, it exhibits an effect for organic gas decomposition, hydrophilic property, stain-proofing, and so on in a space almost free from ultraviolet. The photocatalytic performance can be exhibited also in a case where a light source having a low illuminance such as a light-emitting diode and a midget lamp used as an interior in indoor space of automobiles is used. Therefore, the visible light responsive photocatalyst product can be used also in a place and as an application in which the use thereof has been concerned due to the problem of the light source and the like, and thus an applicable range thereof is broadened.

EXAMPLES

Next, concrete examples and the evaluation results thereof will be described. Note that although the inductively-coupled plasma process is applied to the sublimation process in the following examples.

Example 1

First, a tungsten trioxide powder whose average particle size was 0.5 μm was prepared as a raw material powder. This raw material powder was sprayed to RF plasma together with carrier gas (Ar), and as reaction gas, oxygen was supplied at a flow rate of 80 L/min. A tungsten oxide powder was produced through a sublimation process in which an oxidation reaction of the raw material powder was caused while the raw material powder was being sublimated. The production conditions of the tungsten oxide powder are shown in Table 1.

Regarding the obtained tungsten oxide powder, a BET specific surface area and an average particle size (by image analysis of a TEM photo) were measured. For measuring the BET specific surface area, a specific surface area measuring instrument Macsorb1201 manufactured by MOUNTECH Co., Ltd. was used. A pre-process was performed in nitrogen under the condition of 200° C.×20 minutes. For the TEM observation, H-7100FA manufactured by HITACHI was used, and an enlarged photo was subjected to image analysis and 50 particles or more were extracted, and D50 was calculated by finding a volume-based integrated diameter. The measurement results of the BET specific surface area and the average particle size are shown in Table 2.

Further, the tungsten oxide powder was subjected to X-ray diffraction. For the X-ray diffraction, an X-ray diffraction instrument RINT-2000 manufactured by Rigaku Corporation was used, and a Cu target, a Ni filter, and a graphite (002) monochromator were used. Measuring conditions were as follows: tube/bulb voltage: 40 kV, tube/bulb current: 40 mA, divergent slit: ½°, scattering slit: auto, light-receiving slit: 0.15 mm, 2θ range measured: 20 to 70°, scanning speed: 0.5°/min, and sampling width: 0.004°. In measuring the peak intensities, Kα1 was not removed, and only smoothing and background subtraction processes were performed. For the smoothing, Savizky-Golay (least-squares method) was used and a filter point 11 was set. In the background subtraction, a straight line was fit in the measurement range and a threshold a was set to 3.0. An identification result of a crystal structure of the tungsten oxide powder based on the result of the X-ray diffraction is shown in Table 2.

Further, color of the tungsten oxide powder was measured based on an L*a*b* color system. For the color measurement based on the L*a*b* color system, a spectrophotometric colorimeter CM-2500d manufactured by KONICA MINOLTA was used. The measurement result of the L*a*b* is shown in Table 2.

Next, as a property of the obtained tungsten oxide powder, acetaldehyde decomposition rate was measured. The acetaldehyde gas decomposition rate was evaluated by using a flow-type apparatus as is used in the evaluation of nitrogen oxide removal performance (decomposition performance) of JIS-R-1701-1 (2004), under the following conditions. The gas decomposition rates at the time of irradiating visible light having illuminances of 6000 lx, 2500 lx, 1000 lx, 600 lx are shown in Table 3 and FIG. 1. The tungsten oxide powder in an example 1 exhibited the gas decomposition rate of 86% under the illuminance of 2500 lx, the gas decomposition rate of 66% under 1000 lx, and the gas decomposition rate of 48% under 600 lx.

Further, in order to evaluate the gas decomposition performance under a low illuminance based on the aforementioned gas decomposition rates under the illuminances of 2500 lx, 1000 lx, 600 lx, gas decomposition rates at the time of irradiating visible light having illuminances of 200 lx, 50 lx, were measured. The measurement results are collectively shown in Table 3 and FIG. 1. The tungsten oxide powder of the example 1 exhibited the gas decomposition rate of 20% also under a low illuminance of 200 lx, and further, it exhibited the gas decomposition rate of 7% even under a condition of quite low illuminance of 50 lx. From these results, the tungsten oxide powder of the example 1 was confirmed to have the gas decomposition rate having a nonlinear relation to the illuminance in an illuminance range of 200 to 2500 lx, and to exhibit practical gas decomposition performance also under a low illuminance.

In the acetaldehyde gas decomposition test, an initial concentration of acetaldehyde was 10 ppm, a gas flow rate was 140 mL/min, and a sample amount was 0.2 g. For the adjustment of the sample, it was applied on a 5×10 cm glass plate and was dried. In a case of a powder sample, it was spread by water to be dried. In a pre-process, 12-hour irradiation of black light was performed. A sa light source, a white fluorescent lamp (FL20SS•W/18 manufactured by Toshiba Lighting & Technology Corporation) was used, and light having a wavelength of less than 380 nm was cut by using an ultraviolet cutoff filter (Clarex N-169, manufactured by Nitto Jushi Kogyo Co., Ltd.). Illuminances were respectively adjusted to predetermined values. First, a waiting time without any light irradiation was continued until there occurred no gas absorption and the condition was stabilized. After the stabilization, the light irradiation was started. Under such conditions, the light was emitted and the gas concentration was measured 15 minutes later for finding the gas decomposition rate. However, when the gas concentration was not stabilized even after 15 minutes passed, the light irradiation was continued until the stabilization, and the concentration was measured. As a gas analyzing apparatus, a multi-gas monitor 1412 manufactured by INOVA was used.

Example 2

A tungsten oxide powder was produced through the same sublimation process as that of the example 1 except in that, as reaction gas, argon was supplied at a flow rate of 80 L/min and oxygen was supplied at a flow rate of 5 L/min, and the pressure in a reaction vessel was adjusted to a pressure-reduced side of 35 kPa. Further, the tungsten oxide powder was subjected to heat treatment in the atmosphere under the condition of 400° C.×1.5 h. At this time, the temperature was raised to the heat treatment temperature in 0.5 h, and after the heat treatment, it was lowered to the room temperature in 2 h. The tungsten oxide powder thus obtained was subjected to the same measurement and evaluation as those of the example 1. The production conditions of the tungsten oxide powder are shown in Table 1, the measurement results of powder properties are shown in Table 2, and the measurement results of gas decomposition rate are shown in Table 3 and FIG. 1. The tungsten oxide powder according to an example 2 was confirmed to have the gas decomposition rate having a nonlinear relation to the illuminance in an illuminance range of 200 to 2500 lx, and to exhibit good gas decomposition performance also under a low illuminance.

Examples 3 to 5

In examples 3 to 5, the same sublimation process as that of the example was performed. In the example 3, as reaction gas, argon was supplied at a flow rate of 40 L/min and air was supplied at a flow rate of 40 L/min in the sublimation process, and a heat treatment process was performed under the condition of 500° C.×1 h after the sublimation process. At this time, the temperature was raised to the heat treatment temperature in 0.5 h, and after the heat treatment, it was lowered to the room temperature in 2 h. In the example 4, as reaction gas, argon was supplied at a flow rate of 40 L/min and oxygen was supplied at a flow rate of 100 L/min in the sublimation process, and a heat treatment process was performed under the condition of 650° C.×0.5 h after the sublimation process. At this time, the temperature was raised to the heat treatment temperature in 0.5 h, and after the heat treatment, it was lowered to the room temperature in 2 h. In the example 5, as reaction gas, argon was supplied at a flow rate of 40 L/min and oxygen was supplied at a flow rate of 40 L/min in the sublimation process, and a heat treatment process was performed under the condition of 850° C.×0.25 h after the sublimation process. At this time, the temperature was raised to the heat treatment temperature in 0.5 h, and after the heat treatment, it was lowered to the room temperature in 2 h.

The obtained tungsten oxide powders were subjected to the same measurement and evaluation as those of the example 1. The production conditions of the tungsten oxide powders are shown in Table 1, the measurement results of powder properties are shown in Table 2, and the measurement results of gas decomposition rates are shown in Table 3 and FIG. 1. Each of the tungsten oxide powders according to the examples 3 to 5 was confirmed to have the gas decomposition rate having a nonlinear relation to the illuminance in an illuminance range of 200 to 2500 lx, and to exhibit good gas decomposition performance also under a low illuminance.

Example 6

The sublimation process was performed in the same manner as that of the example 1 except in that argon was supplied at a flow rate of 40 L/min and oxygen was supplied at a flow rate of 40 L/min as reaction gas, and thereafter, a heat treatment process was performed in the atmosphere under the condition of 950° C.×1 h. The obtained tungsten oxide powder was subjected to the same measurement and evaluation as those of the example 1. The production conditions of the tungsten oxide powder are shown in Table 1, the measurement results of powder properties are shown in Table 2, and the measurement results of gas decomposition rate are shown in Table 3 and FIG. 1. The tungsten oxide powder according to an example 6 had the gas decomposition rate having a nonlinear relation to the illuminance in an illuminance range of 200 to 2500 lx, and exhibited the gas decomposition rate of 5% under an illuminance of 200 lx. Further, although the powder exhibited good gas decomposition performance under illuminances of 600 to 2500 lx, the performance was inferior to that of the examples 1 to 5, so that it was not possible to obtain the gas decomposition performance when the illuminance was lowered to 50 lx.

Comparative Example 1

A tungsten oxide powder produced through the same sublimation process as that of the example 5 was subjected to heat treatment in the atmosphere under the condition of 1050° C.×0.25 h. The obtained tungsten oxide powder was subjected to the same measurement and evaluation as those of the example 1. The production conditions of the tungsten oxide powder are shown in Table 1, the measurement results of powder properties are shown in Table 2, and the measurement results of gas decomposition rate are shown in Table 3 and FIG. 1. The tungsten oxide powder had a rather small BET specific surface area of 4 m$^2$/g and a rather large average particle size of 215 nm, so that the gas decomposition rates thereof under illuminances of 600 to 2500 lx were low. Further, since the gas decomposition rate had a linear relation to the illuminance in a range of 200 to 2500 lx, no gas decomposition performance was exhibited under 50 lx. It is thought that this is because particle growth occurred by the high-temperature heat treatment.

Comparative Example 2

The same measurement and evaluation as those of the example 1 were performed by using a tungsten oxide powder (manufactured by Rare Metallic Co., Ltd.) available on the market as a reagent. Powder properties are shown in Table 2, and the measurement results of gas decomposition rate are shown in Table 3 and FIG. 1. From a result of X-ray diffraction, a crystal system was estimated to be a mixed crystal of a monoclinic crystal and a triclinic crystal, a BET specific surface area was 0.7 m$^2$/g and an average particle size was 1210 nm. Since the tungsten oxide powder of the comparative example 2 had a small specific surface area and a significantly large particle size, although it was confirmed to have very little gas decomposition performance under 6000 lx, it exhibited almost no gas decomposition performance under any of 2500 lx, 1000 lx, 600 lx and 200 lx.

Comparative Example 3

In order to improve a visible light activity in titanium oxide, titanium oxide supporting Pt was produced, and was subjected to the same measurement and evaluation as those of the example 1. Powder properties other than a crystal system are shown in Table 2, and the measurement results of gas decomposition rate are shown in Table 3 and FIG. 1. A BET specific surface area was large to be 210 m$^2$/g, and an average particle size was small to be 7.2 nm. The gas decomposition rates under 6000 lx and 2500 lx were relatively high, but, only the gas decomposition rates of 29%, 18%, 5% under 1000 lx, 600 lx, 200 lx, respectively, were obtained, values of the rates being smaller than those of the examples. Since the powder had the gas decomposition rate having a linear relation to the illuminance in an illuminance range of 200 to 2500 lx, it was confirmed to exhibit almost no gas decomposition performance under 50 lx, and thus to exhibit a low activity under a low illuminance.

Comparative Example 4

In order to improve a visible light activity in titanium oxide, titanium oxide supporting Fe was produced, and was subjected to the same measurement and evaluation as those of the example 1. Powder properties other than a crystal system are shown in Table 2, and the measurement results of gas decomposition rate are shown in Table 3 and FIG. 1. A BET specific surface area was large to be 170 m$^2$/g, and an average particle size was small to be 8 nm. The gas decomposition rate under 6000 lx was very high and the gas decomposition rate under 2500 lx was also relatively high, but, only the gas decomposition rates of 26%, 16%, 4% under 1000 lx, 600 lx, 200 lx, respectively, were obtained, values of the rates being smaller than those of the examples. Since the powder had the gas decomposition rate having a linear relation to the illuminance in an illuminance range of 200 to 2500 lx, it was confirmed to exhibit almost no gas decomposition performance under 50 lx, and thus to exhibit a low activity under a low illuminance.

TABLE 1

| | PRODUCTION CONDITIONS | | | |
|---|---|---|---|---|
| | SUBLIMATION PROCESS | | HEAT TREATMENT PROCESS | |
| | RAW MATERIAL | GAS (FLOW RATE) METHOD [L/min] | TEMPERATURE [° C.] | TIME [h] |
| EXAMPLE 1 | WO$_3$ | PLASMA O(80) | — | — |
| EXAMPLE 2 | WO$_3$ | PLASMA Ar(80) + O(5) | 400 | 1.5 |
| EXAMPLE 3 | WO$_3$ | PLASMA Ar(40) + Air(40) | 500 | 1 |
| EXAMPLE 4 | WO$_3$ | PLASMA Ar(40) + O(100) | 650 | 0.5 |
| EXAMPLE 5 | WO$_3$ | PLASMA Ar(40) + O(40) | 850 | 0.25 |
| EXAMPLE 6 | WO$_3$ | PLASMA Ar(40) + O(40) | 950 | 1 |
| COMPARATIVE EXAMPLE 1 | WO$_3$ | PLASMA Ar(40) + O(40) | 1050 | 0.25 |
| COMPARATIVE EXAMPLE 2 | — | — — | — | — |
| COMPARATIVE EXAMPLE 3 | — | — — | — | — |
| COMPARATIVE EXAMPLE 4 | — | — — | — | — |

TABLE 2

| | POWDER PROPERTIES | | | L*a*b* COLOR SYSTEM | | |
|---|---|---|---|---|---|---|
| | BET SPECIFIC SURFACE AREA [m²/g] | AVERAGE PARTICLE SIZE [nm] | CRYSTAL STRUCTURE | a* | b* | L* |
| EXAMPLE 1 | 102 | 9.1 | MONOCLINIC CRYSTAL + TRICLINIC CRYSTAL + RHOMBIC CRYSTAL | −10.8 | 10.2 | 80.4 |
| EXAMPLE 2 | 45 | 20 | MONOCLINIC CRYSTAL + TRICLINIC CRYSTAL + RHOMBIC CRYSTAL | −9.5 | 15.4 | 84.5 |
| EXAMPLE 3 | 29 | 32 | MONOCLINIC CRYSTAL + TRICLINIC CRYSTAL + RHOMBIC CRYSTAL | −10.0 | 20.3 | 91.7 |
| EXAMPLE 4 | 17 | 51 | MONOCLINIC CRYSTAL + TRICLINIC CRYSTAL + RHOMBIC CRYSTAL | −11.5 | 24.2 | 92.3 |
| EXAMPLE 5 | 11 | 79 | MONOCLINIC CRYSTAL + TRICLINIC CRYSTAL | −11.0 | 10.0 | 75.5 |
| EXAMPLE 6 | 7 | 124 | MONOCLINIC CRYSTAL + TRICLINIC CRYSTAL | −13.7 | 31.0 | 83.0 |
| COMPARATIVE EXAMPLE 1 | 4 | 215 | MONOCLINIC CRYSTAL + TRICLINIC CRYSTAL | −15.4 | 42.6 | 85.0 |
| COMPARATIVE EXAMPLE 2 | 0.7 | 1210 | MONOCLINIC CRYSTAL + TRICLINIC CRYSTAL | −16.5 | 48.2 | 88.3 |
| COMPARATIVE EXAMPLE 3 | 210 | 7.2 | — | — | — | — |
| COMPARATIVE EXAMPLE 4 | 170 | 8.0 | — | — | — | — |

TABLE 3

| | GAS DECOMPOSITION RATE (%) | | | | | |
|---|---|---|---|---|---|---|
| | 6000 lx IRRADIATION | 2500 lx IRRADIATION | 1000 lx IRRADIATION | 600 lx IRRADIATION | 200 lx IRRADIATION | 50 lx IRRADIATION |
| EXAMPLE 1 | 95 | 86 | 66 | 48 | 20 | 7 |
| EXAMPLE 2 | 92 | 89 | 72 | 59 | 32 | 15 |
| EXAMPLE 3 | 90 | 87 | 70 | 55 | 30 | 11 |
| EXAMPLE 4 | 80 | 76 | 63 | 49 | 25 | 9 |
| EXAMPLE 5 | 50 | 46 | 36 | 26 | 11 | 3 |
| EXAMPLE 6 | 25 | 20 | 15 | 10 | 5 | 0 |
| COMPARATIVE EXAMPLE 1 | 20 | 15 | 8 | 5 | 2 | 0 |
| COMPARATIVE EXAMPLE 2 | 3 | 0 | 0 | 0 | 0 | 0 |
| COMPARATIVE EXAMPLE 3 | 73 | 65 | 29 | 18 | 5 | 0 |
| COMPARATIVE EXAMPLE 4 | 97 | 61 | 26 | 16 | 4 | 0 |

As above, it can be seen that the material having the gas decomposition rate which has a nonlinear relation to the illuminance in an illuminance range of 200 to 2500 lx and exhibiting a high gas decomposition rate under the irradiation of visible light having illuminances of 2500 lx, 1000 lx, 600 lx exhibits high photocatalytic performance also under a low illuminance of about 200 lx such as an illuminance in a living room where people enjoy gathering and a wash room. Further, it is possible to provide a high-sensitive visible light responsive photocatalyst powder which exhibits gas decomposition performance even under a significantly low illuminance of around 50 lx such as an illuminance on a wall, and in a place where a furniture and a home electric appliance are disposed in the indoor. It is of course that such a material exhibits excellent photocatalytic performance under a high illuminance of 6000 lx.

Example 7

A copper oxide (CuO) powder of 1 mass % was mixed in the tungsten oxide powder obtained in the example 3. Gas decomposition rates of thus obtained tungsten oxide powder were measured in the same manner as that of the example 1. The gas decomposition rates under the irradiation of visible light with illuminances of 6000 lx, 2500 lx, 1000 lx, 600 lx were high to be 96%, 90%, 75%, 61%, respectively, and as a result of this, the gas decomposition rates under the irradiation of visible light with illuminances of 200 lx, 50 lx also indicated favorable values of 36%, 16%, respectively. From the measurement results, it was confirmed that good gas decomposition performance was exhibited under a low illuminance.

Example 8

A water-type coating material was prepared by adding 5 mass % of the tungsten oxide powder produced in the example 3 and 0.05 mass % of colloidal silica. This was applied on glass to be dried, whereby glass having a photocatalytic coating layer was fabricated. Gas decomposition rates of such glass were measured in the same manner as that with respect to the powder. It was confirmed that the gas decomposition rate under the irradiation of visible light with an illuminance of 200 lx indicated a favorable value of 10%.

Further, when the aforesaid coating material was applied on glass in an indoor space of an automobile, smell of cigarette was reduced and the glass was not easily stained. Incidentally, when a hydrophilic property of the glass coated with the coating material was evaluated, a contact angle was 1° or less and an ultrahigh hydrophilic property was exhibited. Further, when antibacterial performance was evaluated by using *Staphylococcus aureus*, colon *bacillus*, and mold, it was confirmed that excellent antibacterial performance was exhibited against any of them. The visible light responsive photocatalyst powder of the example is excellent in decomposition performance of organic gas such as acetaldehyde, and further, the photocatalytic coating layer has high transmittance and is unlikely to have a visual problem such as uneven color. Therefore, they are suitably used for members used in an indoor space of an automobile, building materials used in factories, stores, public facilities, homes and the like, interior materials, home electric appliances, and so on.

Examples 9, 10

A Pd powder of 15 mass % was mixed in each of the tungsten oxide powders obtained in the example 3 and the example 5. Gas decomposition rates of thus obtained tungsten oxide composite material powders were measured in the same manner as that of the example 1. The gas decomposition rates under the irradiation of visible light with an illuminance of 200 lx indicated values of 40%, 17%, respectively, and indicated values higher than those of the tungsten oxide powders before mixing Pd therein, regardless of particle sizes. However, since the color of the powder is black, when a coating material was produced, transparency thereof was eliminated.

Example 11

The tungsten oxide powder obtained in the example 3 was dispersed in an aqueous iron chloride solution. The dispersion liquid was centrifuged, and removal of supernatant and washing by adding water were conducted two times. Thereafter, a powder obtained after removing the supernatant was dried at 110° C. for 12 hours, to thereby produce a tungsten oxide composite material powder containing 1 mass % of Fe. Gas decomposition rates of the tungsten oxide composite material powder were measured in the same manner as that of the example 1. In result, the gas decomposition rate indicated a high value of 35% under the irradiation of visible light with an illuminance of 200 lx.

Example 12

Through the same method as that of the example 11, a tungsten oxide composite material powder containing 0.3 mass % of Cu was produced using an aqueous copper chloride solution. Gas decomposition rates of the tungsten oxide composite material powder were measured in the same manner as that of the example 1. In result, the gas decomposition rate indicated a high value of 37% under the irradiation of visible light with an illuminance of 200 lx.

Example 13

Through the same method as that of the example 11, a tungsten oxide composite material powder containing 0.5 mass % of Ag was produced using an aqueous silver nitrate solution. Gas decomposition rates of the tungsten oxide composite material powder were measured in the same manner as that of the example 1. In result, the gas decomposition rate indicated a high value of 32% under the irradiation of visible light with an illuminance of 200 lx.

Examples 14 to 17

Through the same method as that of the example 11, tungsten oxide composite material powders containing 2 mass % of Pd and 0.5 mass % of Pd, respectively, were produced using an aqueous palladium chloride solution, thereby obtaining powders of an example 14 and an example 15. Further, tungsten oxide composite material powders were produced in the same manner as that of the example 15 except in that the tungsten oxide powders obtained in the example 1 and the example 5 were used, thereby obtaining powders of an example 16 and an example 17. Gas decomposition rates of these powders were measured in the same manner as that of the example 1. In result, the gas decomposition rates under the irradiation of visible light with an illuminance of 200 lx indicated values of 35%, 45%, 34%, 29%, respectively, and indicated values higher than those of the tungsten oxide powders before adding Pd thereto, regardless of particle sizes. However, the powder in which a content ratio of Pd was 2 mass % exhibited gas decomposition performance which was lower than that of the powder containing 0.5 mass % of Pd, maybe because an excess amount of Pd existed around tungsten oxide particles.

Example 18

The tungsten oxide powder obtained in the example 3 was dispersed in an aqueous chloroplatinic acid solution, and visible light was irradiated thereto and methanol was put therein, to thereby perform supporting through a photodeposition method. A centrifugation was performed, and after removal of supernatant and washing by adding water were conducted two times, a powder obtained after removing the supernatant was dried at 110° C. for 12 hours, to thereby produce a tungsten oxide composite material powder containing 0.1 mass % of Pt. Gas decomposition rates of the powder were measured in the same manner as that of the example 1. In result, the gas decomposition rate indicated a high value of 47% under the irradiation of visible light with an illuminance of 200 lx.

Examples 19 to 21

Tungsten oxide composite material powders of an example 19, an example 20 and an example 21 were produced by mixing titanium oxide powders ST-01 (product name, Ishihara Sangyo Kaisha, Ltd.) in the tungsten oxide powders obtained in the example 3 at ratios of 70 mass %, 40 mass %, 10 mass %, respectively. The mixing was conducted using a mortar. Gas decomposition rates of these powders were measured in the same manner as that of the example 1. In result, the gas decomposition rates under the irradiation of visible light with an illuminance of 200 lx indicated values of 18%, 34%, 37%, respectively. Although the performance of the tungsten oxide composite material powder of the example 19 was slightly deteriorated because an amount of tungsten oxide was too small, the gas decomposition rates of the other powders indicated values higher than those of the tungsten oxide powders before mixing.

Examples 22, 23

Powders of an example 22 and an example 23 were produced through the same method as that of the example 21 except in that the tungsten oxide powders obtained in the example 1 and the example 5 were used, in which a titanium oxide powder of 10 mass % was mixed in each of the tungsten oxide powders. Gas decomposition rates of these powders were measured in the same manner as that of the example 1. In result, the gas decomposition rates under the irradiation of visible light with an illuminance of 200 lx indicated values of 30%, 24%, respectively, and it was confirmed that the powders had the gas decomposition rates better than those of the tungsten oxide powders before the titanium oxide powders were mixed therein.

Example 24

The tungsten oxide powder obtained in the example 3 was dispersed in a titanium oxide sol STS-01 (product name, Ishihara Sangyo Kaisha, LTd.), and thereafter, the resultant was dried at 110° C. for 12 hours, thereby producing a tungsten oxide composite material powder containing 5 mass % of $TiO_2$. Gas decomposition rates of this powder were measured in the same manner as that of the example 1. In result, the gas decomposition rate under the irradiation of visible light with an illuminance of 200 lx indicated a high value of 390. It is thought that the high performance was obtained because $TiO_2$ was uniformly dispersed compared to a case where $TiO_2$ was mixed in a state of powder.

Example 25

Through the same method as that of the example 7, a powder in which 20 mass % of CuO powder was mixed in the tungsten oxide powder obtained in the example 3, was produced. Gas decomposition rates of this powder were measured in the same manner as that of the example 1. In result, the gas decomposition rate under the irradiation of visible light with an illuminance of 200 lx indicated 26%. However, the powder had a property inferior to that of the tungsten oxide powder in which the CuO powder was mixed at a ratio of 1 mass % maybe because the content of CuO was too large, and since the color of the powder is black, when a coating material was produced, transparency thereof was eliminated.

Example 26

A zirconium oxide ($ZrO_2$) powder of 0.5 mass % was mixed in the tungsten oxide powder obtained in the example 3. Gas decomposition rates of this powder were measured in the same manner as that of the example 1. In result, the gas decomposition rate under the irradiation of visible light with an illuminance of 200 lx indicated a high value of 32%.

Example 27

The tungsten oxide powder obtained in the example 3 was dispersed in an alumina sol, and the dispersion liquid was dried at 110° C. for 12 hours to produce a powder containing 2 mass % of $Al_2O_3$. Gas decomposition rates of this powder were measured in the same manner as that of the example 1. In result, the gas decomposition rate under the irradiation of visible light with an illuminance of 200 lx was 32%, and a property being the same or better than that of the tungsten oxide powder before mixing was exhibited.

Examples 28 to 30

Powders of an example 28, an example 29 and an example 30 were produced by mixing tungsten carbide (WC) powders in the tungsten oxide powders obtained in the example 3 at ratios of 10 mass %, 2 mass %, 0.5 mass %, respectively. Gas decomposition rates of these powders were measured in the same manner as that of the example 1. In result, the gas decomposition rates under the irradiation of visible light with an illuminance of 200 lx indicated values of 21%, 31%, 35%, respectively. Although the value in the example 28 was lower than that of the tungsten oxide powder before mixing maybe because an amount of WC was too large, the values in the example 29 and the example 30 were the same or higher than those of the tungsten oxide powders before mixing. However, since the color of the powder becomes more black as the content ratio of WC is higher, when a coating material was produced, transparency thereof was eliminated.

Example 31

A dispersion process in a beads mill was conducted using the tungsten oxide powder obtained in the example 3 and water, thereby producing a water-type dispersion liquid whose concentration was 10 mass %. An aqueous cerium chloride solution was mixed in the dispersion liquid to produce a solution in which a mass ratio between Ce and $WO_3$ was 1:999. The solution was applied on a glass plate and then dried at 110° C. for 0.5 hour, to thereby obtain a sample of an example 31. For comparison, the similar sample was produced using only the water dispersion liquid before cerium chloride was mixed therein. Gas decomposition rates of these samples were measured in the same manner as that of the example 1. In result, the gas decomposition rate under the irradiation of visible light with an illuminance of 200 lx indicated a value of 20%, the value being the same as that of the dispersion liquid before Ce was added thereto.

Example 32

The sample produced in the example 31 was further subjected to heat treatment in the atmosphere at 350° C. for 1 hour. Gas decomposition rates of the sample were measured in the same manner as that of the example 1. In result, the gas decomposition rate under the irradiation of visible light with an illuminance of 200 lx indicated a value of 28%, the value being higher than that of the sample (example 31) which was only dried at 110° C. It is thought that the property was improved because excess moisture, chloride and the like were reduced by setting a high heating temperature.

Example 33

A water-type dispersion liquid containing 10 mass % of tungsten oxide was produced by using the powder in the example 3 in the same manner as that of the example 31, and an aqueous nickel nitrate solution was mixed in the dispersion liquid to produce a solution in which a mass ratio between Ni and $WO_3$ was 1:999. The solution was applied on a glass plate and then dried at 110° C. for 0.5 hour, and further heated in the atmosphere at 350° C. for 1 hour, to thereby obtain a sample of an example 33. Gas decomposition rates of the sample were measured in the same manner as that of the example 1. In result, the gas decomposition rate under the irradiation of visible light with an illuminance of 200 lx indicated a value of 25%, the value being higher than that of the dispersion liquid before Ni was added thereto.

Example 34

A water-type dispersion liquid containing 10 mass % of tungsten oxide was produced by using the powder in the example 3 in the same manner as that of the example 33, and an aqueous manganese chloride solution was mixed in the dispersion liquid to produce a solution in which a mass ratio between Mn and $WO_3$ was 1:999. The solution was applied on a glass plate and then dried at 110° C. for 0.5 hour, and further heated in the atmosphere at 350° C. for 1 hour, to thereby obtain a sample of an example 34. Gas decomposition rates of the sample were measured in the same manner as that of the example 1. In result, the gas decomposition rate under the irradiation of visible light with an illuminance of 200 lx indicated a value of 27%, the value being higher than that of the dispersion liquid before Mn was added thereto. Each sample of the aforementioned respective examples was confirmed to have high hydrophilic property, antibacterial property and antifungal property.

Example 35

A tungsten trioxide powder whose average particle size was 0.5 μm was prepared as a raw material powder. This raw material powder was sprayed to RF plasma together with carrier gas (Ar), and as reaction gas, oxygen was supplied at a flow rate of 80 L/min. As above, a tungsten oxide powder was produced through a sublimation process in which an oxidation reaction of the raw material powder was caused while the raw material powder was being sublimated. The production conditions of the tungsten oxide powder are shown in Table 4.

Regarding the obtained tungsten oxide powder, a BET specific surface area and an average particle size (by image analysis of a TEM photo) were measured in the same manner as that of the example 1. The measurement results of the BET specific surface area and the average particle size are shown in Table 5. Further, X-ray diffraction was performed on the tungsten oxide powder in the same manner as that of the example 1. An identification result of a crystal structure of the tungsten oxide powder based on the result of the X-ray diffraction is shown in Table 5. Further, color of the tungsten oxide powder was measured based on an L*a*b* color system, similar to the example 1. The measurement result of the L*a*b* is shown in Table 5.

Next, as a property of the obtained tungsten oxide powder, acetaldehyde decomposition rate was measured. The acetaldehyde gas decomposition rate was evaluated by using a flow-type apparatus as is used in the evaluation of nitrogen oxide removal performance (decomposition performance) of JIS-R-1701-1 (2004), under the following conditions. The gas decomposition rates at the time of irradiating visible light having illuminances of 6000 lx, 2500 lx, 1000 lx, 600 lx are shown in Table 6. The tungsten oxide powder in an example 35 exhibited the gas decomposition rate of 86% under the illuminance of 2500 lx, the gas decomposition rate of 66% under 1000 lx, and the gas decomposition rate of 48% under 600 lx.

Further, in order to evaluate the gas decomposition performance under a low illuminance based on the aforementioned gas decomposition rates under the illuminances of 2500 lx, 1000 lx, 600 lx, gas decomposition rates at the time of irradiating visible light having illuminances of 200 lx, 50 lx, were measured. The measurement results are collectively shown in Table 6. The tungsten oxide powder of the example 35 exhibited the gas decomposition rate of 20% also under a low illuminance of 200 lx, and further, it exhibited the gas decomposition rate of 7% even under a condition of quite low illuminance of 50 lx. From these results, the tungsten oxide powder of the example 35 was confirmed to have the gas decomposition rate having a nonlinear relation to the illuminance in an illuminance range of 200 to 2500 lx, and to exhibit practical gas decomposition performance also under a low illuminance.

In the acetaldehyde gas decomposition test, an initial concentration of acetaldehyde was 10 ppm, a gas flow rate was 140 mL/min, and a sample amount was 0.2 g. For the adjustment of the sample, it was applied on a 5×10 cm glass plate and was dried. In a case of a powder sample, it was spread by water to be dried. In a pre-process, 12-hour irradiation of black light was performed. As a light source, NSPW-510CS manufactured by Nichia chemical Co., Ltd. was used as a white LED, and illuminances were respectively adjusted to predetermined values. First, a waiting time without any light irradiation was continued until there occurred no gas absorption and the condition was stabilized. After the stabilization, the light irradiation was started. Under such conditions, the light was emitted and the gas concentration was measured 15 minutes later for finding the gas decomposition rate. However, when the gas concentration was not stabilized even after 15 minutes passed, the light irradiation was continued until the stabilization, and the concentration was measured. As a gas analyzing apparatus, a multi-gas monitor 1412 manufactured by INOVA was used.

Example 36

A tungsten oxide powder was produced through the same sublimation process as that of the example 35 except in that, as reaction gas, argon was supplied at a flow rate of 80 L/min and oxygen was supplied at a flow rate of 5 L/min, and the pressure in a reaction vessel was adjusted to a pressure-reduced side of 35 kPa. Further, the tungsten oxide powder was subjected to heat treatment in the atmosphere under the condition of 400° C.×1.5 h. At this time, the temperature was raised to the heat treatment temperature in 0.5 hour, and after the heat treatment, it was lowered to the room temperature in 2 hours. The tungsten oxide powder thus obtained was subjected to the same measurement and evaluation as those of the example 35. The production conditions of the tungsten oxide powder are shown in Table 4, the measurement results of powder properties are shown in Table 5, and the measurement results of gas decomposition rate are shown in Table 6. The tungsten oxide powder according to an example 36 was confirmed to have the gas decomposition rate having a nonlinear relation to the illuminance in an illuminance range of 200 to 2500 lx, and to exhibit good gas decomposition performance also under a low illuminance.

Examples 37 to 39

In examples 37 to 39, the same sublimation process as that of the example 35 was performed. In the example 37, as reaction gas, argon was supplied at a flow rate of 40 L/min and air was supplied at a flow rate of 40 L/min in the sublimation process, and a heat treatment process was performed under the condition of 500° C.×1 h after the sublimation process. The temperature was raised to the heat treatment temperature in 0.5 hour, and after the heat treatment, it was lowered to the room temperature in 2 hours. In the example 38, as reaction gas, argon was supplied at a flow rate of 40 L/min and oxygen was supplied at a flow rate of 100 L/min in the sublimation process, and a heat treatment process was performed under the condition of 650° C.×0.5 h after the sublimation process. The temperature was raised to the heat treatment temperature in 0.5 hour, and after the heat treatment, it was lowered to the room temperature in 2 hours. In the example 39, as reaction gas, argon was supplied at a flow rate of 40 L/min and oxygen was supplied at a flow rate of 40 L/min in the sublimation process, and a heat treatment process was performed under the condition of 850° C.×0.25 h after the sublimation process. The temperature was raised to the heat treatment temperature in 0.5 hour, and after the heat treatment, it was lowered to the room temperature in 2 hours.

The obtained tungsten oxide powders were subjected to the same measurement and evaluation as those of the example 35. The production conditions of the tungsten oxide powders are shown in Table 4, the measurement results of powder properties are shown in Table 5, and the measurement results of gas decomposition rates are shown in Table 6. Each of the tungsten oxide powders according to the examples 37 to 39 was confirmed to have the gas decomposition rate having a nonlinear relation to the illuminance in an illuminance range of 200 to 2500 lx, and to exhibit good gas decomposition performance also under a low illuminance.

Example 40

The sublimation process was performed in the same manner as that of the example 35 except in that argon was supplied at a flow rate of 40 L/min and oxygen was supplied at a flow rate of 40 L/min as reaction gas, and thereafter, a heat treatment process was performed in the atmosphere under the condition of 950° C.×1 h. The obtained tungsten oxide powder was subjected to the same measurement and evaluation as those of the example 35. The production conditions of the tungsten oxide powder are shown in Table 4, the measurement results of powder properties are shown in Table 5, and the measurement results of gas decomposition rate are shown in Table 6. The tungsten oxide powder according to an example 40 had the gas decomposition rate having a nonlinear relation to the illuminance in an illuminance range of 200 to 2500 lx, and exhibited the gas decomposition rate of 5% under an illuminance of 200 lx. Further, although the powder exhibited good gas decomposition performance under illuminances of 600 to 2500 lx, the performance was inferior to that of the examples 35 to 39, so that it was not possible to obtain the gas decomposition performance when the illuminance was lowered to 50 lx.

Comparative Example 5

A tungsten oxide powder produced through the same sublimation process as that of the example 39 was subjected to heat treatment in the atmosphere under the condition of 1050° C.×0.25 h. The obtained tungsten oxide powder was subjected to the same measurement and evaluation as those of the example 35. The production conditions of the tungsten oxide powder are shown in Table 4, the measurement results of powder properties are shown in Table 5, and the measurement results of gas decomposition rate are shown in Table 6. The tungsten oxide powder had a rather small BET specific surface area of 4 m²/g and a rather large average particle size of 215 nm, so that the gas decomposition rates thereof under illuminances of 600 to 2500 lx were low. Further, since the gas decomposition rate had a linear relation to the illuminance in a range of 200 to 2500 lx, no gas decomposition performance was exhibited under 50 lx. It is thought that this is because particle growth occurred by the high-temperature heat treatment.

Comparative Example 6

The same measurement and evaluation as those of the example 35 were performed by using a tungsten oxide powder (manufactured by Rare Metallic Co., Ltd.) available on the market as a reagent. Powder properties are shown in Table 5, and the measurement results of gas decomposition rate are shown in Table 6. From a result of X-ray diffraction, a crystal system was estimated to be a mixed crystal of a monoclinic crystal and a triclinic crystal, a BET specific surface area was 0.7 m²/g and an average particle size was 1210 nm. Since the tungsten oxide powder of the comparative example 6 had a small specific surface area and a significantly large particle size, although it was confirmed to have very little gas decomposition performance under 6000 lx, it exhibited almost no gas decomposition performance under any of 2500 lx, 1000 lx, 600 lx and 200 lx.

Comparative Example 7

In order to improve a visible light activity in titanium oxide, titanium oxide supporting Pt was produced, and was subjected to the same measurement and evaluation as those of the example 35. Powder properties other than a crystal system are shown in Table 5, and the measurement results of gas decomposition rate are shown in Table 6. A BET specific surface area was large to be 210 m²/g, and an average particle size was small to be 7.2 nm. The gas decomposition rates under 6000 lx and 2500 lx were relatively high, but, only the gas decomposition rates of 20%, 13%, 3% under 1000 lx, 600 lx, 200 lx, respectively, were obtained, values of the rates being smaller than those of the examples. Since the powder had the gas decomposition rate having a linear relation to the illuminance in an illuminance range of 200 to 2500 lx, it was confirmed to exhibit almost no gas decomposition performance under 50 lx, and thus to exhibit a low activity under a low illuminance.

Comparative Example 8

In order to improve a visible light activity in titanium oxide, titanium oxide supporting Fe was produced, and was subjected to the same measurement and evaluation as those of the example 35. Powder properties other than a crystal system are shown in Table 5, and the measurement results of gas decomposition rate are shown in Table 6. A BET specific surface area was large to be 170 m²/g, and an average particle size was small to be 8 nm. The gas decomposition rate under 6000 lx was very high and the gas decomposition rate under 2500 lx was also relatively high, but, only the gas decomposition rates of 20%, 11%, 3% under 1000 lx, 600 lx, 200 lx, respectively, were obtained, values of the rates being smaller than those of the examples. Since the powder had the gas decomposition rate having a linear relation to the illuminance in an illuminance range of 200 to 2500 lx, it was confirmed to exhibit almost no gas decomposition performance under 50 lx, and thus to exhibit a low activity under a low illuminance.

TABLE 4

| | PRODUCTION CONDITIONS | | | | |
|---|---|---|---|---|---|
| | SUBLIMATION PROCESS | | | HEAT TREATMENT PROCESS | |
| | RAW MATERIAL | METHOD | GAS (FLOW RATE) [L/min] | TEMPERATURE [° C.] | TIME [h] |
| EXAMPLE 35 | $WO_3$ | PLASMA | O(80) | — | — |
| EXAMPLE 36 | $WO_3$ | PLASMA | Ar(80) + O(5) | 400 | 1.5 |
| EXAMPLE 37 | $WO_3$ | PLASMA | Ar(40) + Air(40) | 500 | 1 |
| EXAMPLE 38 | $WO_3$ | PLASMA | Ar(40) + O(100) | 650 | 0.5 |
| EXAMPLE 39 | $WO_3$ | PLASMA | Ar(40) + O(40) | 850 | 0.25 |
| EXAMPLE 40 | $WO_3$ | PLASMA | Ar(40) + O(40) | 950 | 1 |
| COMPARATIVE EXAMPLE 5 | $WO_3$ | PLASMA | Ar(40) + O(40) | 1050 | 0.25 |
| COMPARATIVE EXAMPLE 6 | — | — | — | — | — |
| COMPARATIVE EXAMPLE 7 | — | — | — | — | — |
| COMPARATIVE EXAMPLE 8 | — | — | — | — | — |

TABLE 5

| | POWDER PROPERTIES | | | | | |
|---|---|---|---|---|---|---|
| | BET SPECIFIC SURFACE AREA [$m^2/g$] | AVERAGE PARTICLE SIZE [nm] | CRYSTAL STRUCTURE | L*a*b* COLOR SYSTEM | | |
| | | | | a* | b* | L* |
| EXAMPLE 35 | 102 | 9.1 | MONOCLINIC CRYSTAL + TRICLINIC CRYSTAL + RHOMBIC CRYSTAL | −10.8 | 10.2 | 80.4 |
| EXAMPLE 36 | 45 | 20 | MONOCLINIC CRYSTAL + TRICLINIC CRYSTAL + RHOMBIC CRYSTAL | −9.5 | 15.4 | 84.5 |
| EXAMPLE 37 | 29 | 32 | MONOCLINIC CRYSTAL + TRICLINIC CRYSTAL + RHOMBIC CRYSTAL | −10.0 | 20.3 | 91.7 |
| EXAMPLE 38 | 17 | 51 | MONOCLINIC CRYSTAL + TRICLINIC CRYSTAL + RHOMBIC CRYSTAL | −11.5 | 24.2 | 92.3 |
| EXAMPLE 39 | 11 | 79 | MONOCLINIC CRYSTAL + TRICLINIC CRYSTAL | −11.0 | 10.0 | 75.5 |
| EXAMPLE 40 | 7 | 124 | MONOCLINIC CRYSTAL + TRICLINIC CRYSTAL | −13.7 | 31.0 | 83.0 |
| COMPARATIVE EXAMPLE 5 | 4 | 215 | MONOCLINIC CRYSTAL + TRICLINIC CRYSTAL | −15.4 | 42.6 | 85.0 |
| COMPARATIVE EXAMPLE 6 | 0.7 | 1210 | MONOCLINIC CRYSTAL + TRICLINIC CRYSTAL | −16.5 | 48.2 | 88.3 |
| COMPARATIVE EXAMPLE 7 | 210 | 7.2 | — | — | — | — |
| COMPARATIVE EXAMPLE 8 | 170 | 8.0 | — | — | — | — |

TABLE 6

| | GAS DECOMPOSITION RATE (%) | | | | | |
|---|---|---|---|---|---|---|
| | 6000 lx IRRADIATION | 2500 lx IRRADIATION | 1000 lx IRRADIATION | 600 lx IRRADIATION | 200 lx IRRADIATION | 50 lx IRRADIATION |
| EXAMPLE 35 | 95 | 86 | 66 | 48 | 20 | 7 |
| EXAMPLE 36 | 92 | 89 | 72 | 59 | 32 | 15 |
| EXAMPLE 37 | 90 | 87 | 70 | 55 | 30 | 11 |
| EXAMPLE 38 | 80 | 76 | 63 | 49 | 25 | 9 |
| EXAMPLE 39 | 50 | 46 | 36 | 26 | 11 | 3 |
| EXAMPLE 40 | 25 | 20 | 15 | 10 | 5 | 0 |
| COMPARATIVE EXAMPLE 5 | 20 | 15 | 8 | 5 | 2 | 0 |
| COMPARATIVE EXAMPLE 6 | 3 | 0 | 0 | 0 | 0 | 0 |
| COMPARATIVE EXAMPLE 7 | 73 | 52 | 20 | 13 | 3 | 0 |
| COMPARATIVE EXAMPLE 8 | 92 | 49 | 20 | 11 | 3 | 0 |

As above, it can be seen that the material having the gas decomposition rate which has a nonlinear relation to the illuminance in an illuminance range of 200 to 2500 lx and exhibiting a high gas decomposition rate under the irradiation of visible light having illuminances of 2500 lx, 1000 lx, 600 lx exhibits high photocatalytic performance also under a low illuminance of about 200 lx such as an illuminance in a living room where people enjoy gathering and a wash room. Further, it is possible to provide a high-sensitive visible light responsive photocatalyst powder which exhibits gas decomposition performance even under a significantly low illuminance of around 50 lx such as an illuminance on a wall, and in a place where a furniture and a home electric appliance are disposed in the indoor. It is of course that such a material exhibits excellent photocatalytic performance under a high illuminance of 6000 lx.

Example 41

A copper oxide (CuO) powder of 1 mass % was mixed in the tungsten oxide powder obtained in the example 37. Gas decomposition rates of thus obtained tungsten oxide powder were measured in the same manner as that of the example 1. The gas decomposition rates under the irradiation of visible light with illuminances of 6000 lx, 2500 lx, 1000 lx, 600 lx were high to be 96%, 90%, 75%, 61%, respectively, and as a result of this, the gas decomposition rates under the irradiation of visible light with illuminances of 200 lx, 50 lx also indicated favorable values of 36%, 16%, respectively. From the measurement results, it was confirmed that good gas decomposition performance was exhibited under a low illuminance.

Example 42

A water-type coating material was prepared by adding 5 mass % of the tungsten oxide powder produced in the example 37 and 0.05 mass % of colloidal silica. This was applied on glass to be dried, whereby glass having a photocatalytic coating layer was fabricated. Gas decomposition rates of such glass were measured in the same manner as that with respect to the powder. It was confirmed that the gas decomposition rate under the irradiation of visible light with an illuminance of 200 lx indicated a favorable value of 10%.

Further, when the aforesaid coating material was applied on glass in an indoor space of an automobile, smell of cigarette was reduced and the glass was not easily stained. Incidentally, when a hydrophilic property of the glass coated with the coating material was evaluated, a contact angle was 1° or less and an ultrahigh hydrophilic property was exhibited. Further, when antibacterial performance was evaluated by using *Staphylococcus aureus*, colon *bacillus*, and mold, it was confirmed that excellent antibacterial performance was exhibited against any of them. The visible light responsive photocatalyst powder of the example is excellent in decomposition performance of organic gas such as acetaldehyde, and further, the photocatalytic coating layer has high transmittance and is unlikely to have a visual problem such as uneven color. Therefore, they are suitably used for members used in an indoor space of an automobile, building materials used in factories, stores, schools, public facilities, hospitals, welfare facilities, accommodation facilities, homes and the like, interior materials, home electric appliances, and so on. An air cleaner including the visible light responsive photocatalyst material of the example and a white LED was manufactured, and a deodorization effect was obtained. Further, when the air cleaner was structured such that a case thereof was formed by using a translucent resin and light of the white LED was irradiated appropriately to the outside, an operating state of the air cleaner could be confirmed, and besides, decorativeness was improved.

Example 43

Tungsten oxide composite material powders were produced in the same manner as that of the examples 9 to 34, by using the tungsten oxide powders in the examples 37, 39. When properties of these powders were evaluated in the same manner as that of the example 35, the improvement of properties was confirmed, similar to the examples 9 to 34.

Example 44

A tungsten trioxide powder whose average particle size was 0.5 μm was prepared as a raw material powder. This raw material powder was sprayed to RF plasma together with carrier gas (Ar), and as reaction gas, oxygen was supplied at a flow rate of 75 L/min. As above, a tungsten oxide powder was produced through a sublimation process in which an oxidation reaction of the raw material powder was caused while the raw material powder was being sublimated. The production conditions of the tungsten oxide powder are shown in Table 7.

Regarding the obtained tungsten oxide powder, a BET specific surface area and an average particle size (by image analysis of a TEM photo) were measured in the same manner as that of the example 1. Further, X-ray diffraction was performed on the tungsten oxide powder in the same manner as that of the example 1. An identification result of a crystal structure of the tungsten oxide powder based on the result of the X-ray diffraction is shown in Table 8. Further, color of the tungsten oxide powder was measured based on an L*a*b* color system, similar to the example 1. The measurement result of the L*a*b* is shown in Table 8.

Next, as a property of the obtained tungsten oxide powder, acetaldehyde decomposition rate was measured. The acetaldehyde gas decomposition rate was evaluated by using a flow-type apparatus as is used in the evaluation of nitrogen oxide removal performance (decomposition performance) of JIS-R-1701-1 (2004), under the following conditions. The gas decomposition rates at the time of irradiating visible light having illuminances of 6000 lx, 2500 lx, 1000 lx, 600 lx were respectively measured. Ratios of the gas decomposition rates under 2500 lx, 1000 lx, 600 lx with respect to the gas decomposition rate under an illuminance of 6000 lx are shown in Table 9. Further, the minimum illuminance at which the tungsten oxide powder exhibited the gas decomposition performance was measured. The measurement results are collectively shown in Table 9.

In the tungsten oxide powder of an example 44, the ratio (G2/G1) of the gas decomposition rate (G2) under 2500 lx with respect to the gas decomposition rate (G1) under an illuminance of 6000 lx was 88%. Further, the ratio (G3/G1) of the gas decomposition rate (G3) under 1000 lx with respect to the gas decomposition rate (G1) under the illuminance of 6000 lx was 66%, and the ratio (G4/G1) of the gas decomposition rate (G4) under 600 lx with respect to G1 was 48%. As above, it was confirmed that the tungsten oxide powder of the example 44 suppressed the decrease in the gas decomposition rate in accordance with the decrease in the illuminance, and as a result of this, the powder exhibited a gas decomposition rate of 2% even under a condition of quite low illuminance of 10 lx, and thus it could obtain good gas decomposition performance also under a low illuminance.

In the acetaldehyde gas decomposition test, an initial concentration of acetaldehyde was 10 ppm, a gas flow rate was 140 mL/min, and a sample amount was 0.2 g. Although it is preferable that the sample amount is set to 0.2 g, if it is not possible, the measurement can be made using the same sample amount under the respective illuminances. For the adjustment of the sample, it was applied on a 5×10 cm glass plate and was dried. In a case of a powder sample, it was spread by water to be dried. In a pre-process, 12-hour irradiation of black light was performed. As a light source, a white fluorescent lamp (FL20SS•W/18 manufactured by Toshiba Lighting & Technology Corporation) was used, and a wavelength of less than 380 nm was cut by using an ultraviolet cutoff filter (Clarex N-169, manufactured by Nitto Jushi Kogyo Co., Ltd.). Illuminances were respectively adjusted to predetermined values. First, a waiting time without any light irradiation was continued until there occurred no gas absorption and the condition was stabilized. After the stabilization, the light irradiation was started. Under such conditions, the light was emitted and the gas concentration was measured 15 minutes later for finding the gas decomposition rate. However, when the gas concentration was not stabilized even after 15 minutes passed, the light irradiation was continued until the stabilization, and the concentration was measured. As a gas analyzing apparatus, a multi-gas monitor 1412 manufactured by INOVA was used.

Example 95

A tungsten oxide powder was produced through the same sublimation process as that of the example 49 except in that, as reaction gas, argon was supplied at a flow rate of 80 L/min and oxygen was supplied at a flow rate of 5 L/min, and the pressure in a reaction vessel was adjusted to a pressure-reduced side of 35 kPa. Further, the tungsten oxide powder was subjected to heat treatment in the atmosphere under the condition of 400° C.×1 h. At this time, the temperature was raised to the heat treatment temperature in 0.5 hour, and after the heat treatment, it was lowered to the room temperature in 2 hours. The tungsten oxide powder thus obtained was subjected to the same measurement and evaluation as those of the example 49. The production conditions of the tungsten oxide powder are shown in Table 7, the measurement results of powder properties are shown in Table 8, and the measurement results of gas decomposition performance are shown in Table 9. It was confirmed that the tungsten oxide powder of an example 45 exhibited a gas decomposition rate of 9% even under a condition of quite low illuminance of 10 lx, and thus it could obtain good gas decomposition performance also under a low illuminance.

Examples 46 to 48

In examples 46 to 48, the same sublimation process as that of the example 44 was performed. In the example 46, as reaction gas, argon was supplied at a flow rate of 40 L/min and air was supplied at a flow rate of 40 L/min in the sublimation process, and a heat treatment process was performed under the condition of 500° C.×0.75 h after the sublimation process. The temperature was raised to the heat treatment temperature in 0.5 hour, and after the heat treatment, it was lowered to the room temperature in 2 hours. In the example 47, as reaction gas, argon was supplied at a flow rate of 40 L/min and oxygen was supplied at a flow rate of 100 L/min in the sublimation process, and a heat treatment process was performed under the condition of 600° C.×1 h after the sublimation process. The temperature was raised to the heat treatment temperature in 0.5 hour, and after the heat treatment, it was lowered to the room temperature in 2 hours. In the example 48, as reaction gas, argon was supplied at a flow rate of 40 L/min and oxygen was supplied at a flow rate of 40 L/min in the sublimation process, and a heat treatment process was performed under the condition of 800° C.×0.5 h after the sublimation process. The temperature was raised to the heat treatment temperature in 0.5 hour, and after the heat treatment, it was lowered to the room temperature in 2 hours.

The obtained tungsten oxide powders were subjected to the same measurement and evaluation as those of the example 44. The production conditions of the tungsten oxide powders are shown in Table 7, the measurement results of powder properties are shown in Table 8, and the measurement results of gas decomposition performance are shown in Table 9. The tungsten oxide powder of the example 46 exhibited the gas decomposition rate of 7% under an illuminance of 10 lx, and the tungsten oxide powders of the example 47 and the example 48 exhibited the gas decomposition rates of 4%, 1%, respectively, under the same illuminance. From these results, it was confirmed that each of the examples 46 to 48 exhibited good gas decomposition performance also under a low illuminance.

Example 49

The sublimation process was performed in the same manner as that of the example 44 except in that argon was supplied at a flow rate of 40 L/min and oxygen was supplied at a flow rate of 40 L/min as reaction gas, and thereafter, a heat treatment process was performed in the atmosphere under the condition of 950° C.×0.75 h. The obtained tungsten oxide powder was subjected to the same measurement and evaluation as those of the example 44. The production conditions of the tungsten oxide powder are shown in Table 7, the measurement results of powder properties are shown in Table 8, and the measurement results of gas decomposition performance are shown in Table 9. The tungsten oxide powder according to an example 49 exhibited good gas decomposition performance under illuminances of 2500 to 600 lx, but, the performance was inferior to that of the examples 44 to 48. Accordingly, although it was not possible to obtain the gas decomposition performance when the illuminance was lowered to 10 lx, a gas decomposition rate of 1% was exhibited under an illuminance of 50 lx.

Comparative Example 9

A tungsten oxide powder produced through the same sublimation process as that of the example 46 was subjected to heat treatment in the atmosphere under the condition of 1050° C.×0.25 h. The obtained tungsten oxide powder was subjected to the same measurement and evaluation as those of the example 44. The production conditions of the tungsten oxide powder are shown in Table 7, the measurement results of powder properties are shown in Table 8, and the measurement results of gas decomposition performance are shown in Table 9. The tungsten oxide powder had a rather small BET specific surface area of 4 $m^2/g$ and a rather large average particle size of 215 nm, so that a ratio of the gas decomposition rate under 2500 lx with respect to the gas decomposition rate under 6000 lx was low, and ratios of the gas decomposition rates under 1000 lx and 600 lx with respect to the gas decomposition rate under 6000 lx were also low. As a result of this, although a very small gas decomposition rate was exhibited under 200 lx, no gas decomposition performance was exhibited under 100 lx. It is thought that this is because particle growth occurred by the high-temperature heat treatment.

Comparative Example 10

The same measurement and evaluation as those of the example 44 were performed by using a tungsten oxide powder (manufactured by Rare Metallic Co., Ltd.) available on the market as a reagent. Powder properties are shown in Table 8, and the measurement results of gas decomposition performance are shown in Table 9. From a result of X-ray diffraction, a crystal system was estimated to be a mixed crystal of a monoclinic crystal and a triclinic crystal, a BET specific surface area was 0.7 m$^2$/g and an average particle size was 1210 nm. Since the tungsten oxide powder of a comparative example 10 had a small specific surface area and a significantly large particle size, although it exhibited a very small gas decomposition rate under 6000 lx, no gas decomposition rate was exhibited under 2500 lx or lower.

Comparative Example 11

In order to improve a visible light activity, titanium oxide supporting Pt was produced, and was subjected to the same measurement and evaluation as those of the example 44. Powder properties other than a crystal system are shown in Table 8, and the measurement results of gas decomposition performance are shown in Table 9. ABET specific surface area was large to be 210 m$^2$/g, and an average particle size was small to be 7.2 nm. Although a ratio of the gas decomposition rate under 2500 lx with respect to the gas decomposition rate under 6000 lx was relatively high to be 89%, ratios of the gas decomposition rates under 1000 lx and 600 lx with respect to the gas decomposition rate under 6000 lx were low to be 40%, 25%, respectively. As a result of this, it was confirmed that only the low gas decomposition rate of to was obtained under 100 lx, no gas decomposition performance was exhibited under 50 lx, and thus the activity was low under a low illuminance.

Comparative Example 12

In order to improve a visible light activity, titanium oxide supporting Fe was produced, and was subjected to the same measurement and evaluation as those of the example 44. Powder properties other than a crystal system are shown in Table 8, and the measurement results of gas decomposition performance are shown in Table 9. ABET specific surface area was large to be 170 m$^2$/g, and an average particle size was small to be 8 nm. A ratio of the gas decomposition rate under 2500 lx with respect to the gas decomposition rate under 6000 lx was low to be 63%, and ratios of the gas decomposition rates under 1000 lx and 600 lx with respect to the gas decomposition rate under 6000 lx were also low to be 27%, 16%, respectively. As a result of this, it was confirmed that only the low gas decomposition rate of 4% was obtained under 200 lx, no gas decomposition performance was exhibited under 100 lx, and thus the activity was low under a low illuminance.

TABLE 7

| | PRODUCTION CONDITIONS | | | |
| --- | --- | --- | --- | --- |
| | SUBLIMATION PROCESS | | HEAT TREATMENT PROCESS | |
| | RAW MATERIAL | METHOD | GAS (FLOW RATE) [L/min] | TEMPERATURE [° C.] | TIME [h] |
| EXAMPLE 44 | WO$_3$ | PLASMA | O(75) | — | — |
| EXAMPLE 45 | WO$_3$ | PLASMA | Ar(80) + O(5) | 400 | 1 |
| EXAMPLE 46 | WO$_3$ | PLASMA | Ar(40) + Air(40) | 500 | 0.75 |
| EXAMPLE 47 | WO$_3$ | PLASMA | Ar(40) + O(100) | 600 | 1 |
| EXAMPLE 48 | WO$_3$ | PLASMA | Ar(40) + O(40) | 800 | 0.5 |
| EXAMPLE 49 | WO$_3$ | PLASMA | Ar(40) + O(40) | 950 | 0.75 |
| COMPARATIVE EXAMPLE 9 | WO$_3$ | PLASMA | Ar(40) + O(40) | 1050 | 0.25 |
| COMPARATIVE EXAMPLE 10 | — | — | — | — | — |
| COMPARATIVE EXAMPLE 11 | — | — | — | — | — |
| COMPARATIVE EXAMPLE 12 | — | — | — | — | — |

TABLE 8

| | POWDER PROPERTIES | | | | | |
| --- | --- | --- | --- | --- | --- | --- |
| | BET SPECIFIC SURFACE AREA [m$^2$/g] | AVERAGE PARTICLE SIZE [nm] | CRYSTAL STRUCTURE | L*a*b* COLOR SYSTEM | | |
| | | | | a* | b* | L* |
| EXAMPLE 44 | 110 | 8 | MONOCLINIC CRYSTAL + TRICLINIC CRYSTAL + RHOMBIC CRYSTAL | −8.1 | 9.5 | 81.2 |
| EXAMPLE 45 | 46 | 20 | MONOCLINIC CRYSTAL + TRICLINIC CRYSTAL + RHOMBIC CRYSTAL | −9.3 | 14.9 | 85.5 |
| EXAMPLE 46 | 34 | 28 | MONOCLINIC CRYSTAL + TRICLINIC CRYSTAL + RHOMBIC CRYSTAL | −11.3 | 19.8 | 90.6 |
| EXAMPLE 47 | 19 | 46 | MONOCLINIC CRYSTAL + TRICLINIC CRYSTAL + RHOMBIC CRYSTAL | −11.8 | 23.6 | 93.1 |
| EXAMPLE 48 | 11 | 80 | MONOCLINIC CRYSTAL + TRICLINIC CRYSTAL | −10.3 | 10.1 | 76.7 |
| EXAMPLE 49 | 6.8 | 130 | MONOCLINIC CRYSTAL + TRICLINIC CRYSTAL | −13.0 | 29.8 | 80.8 |

TABLE 8-continued

| | POWDER PROPERTIES | | | L*a*b* COLOR SYSTEM | | |
|---|---|---|---|---|---|---|
| | BET SPECIFIC SURFACE AREA [m²/g] | AVERAGE PARTICLE SIZE [nm] | CRYSTAL STRUCTURE | a* | b* | L* |
| COMPARATIVE EXAMPLE 9 | 4 | 215 | MONOCLINIC CRYSTAL + TRICLINIC CRYSTAL | −15.4 | 42.6 | 85.0 |
| COMPARATIVE EXAMPLE 10 | 0.7 | 1210 | MONOCLINIC CRYSTAL + TRICLINIC CRYSTAL | −16.5 | 48.2 | 88.3 |
| COMPARATIVE EXAMPLE 11 | 210 | 7.2 | — | — | — | — |
| COMPARATIVE EXAMPLE 12 | 170 | 8.0 | — | — | — | — |

TABLE 9

| | RATIO OF GAS DECOMPOSITION RATE WITH RESPECT TO GAS DECOMPOSITION RATE UNDER 6000 lx (%) | | | ILLUMINANCE AT WHICH GAS DECOMPOSITION PERFORMANCE IS EXHIBITED (lx) |
|---|---|---|---|---|
| | 2500 lx IRRADIATION | 1000 lx IRRADIATION | 600 lx IRRADIATION | |
| EXAMPLE 44 | 88 | 66 | 48 | 10 |
| EXAMPLE 45 | 99 | 82 | 66 | 10 |
| EXAMPLE 46 | 98 | 81 | 63 | 10 |
| EXAMPLE 47 | 95 | 78 | 63 | 10 |
| EXAMPLE 48 | 94 | 74 | 60 | 10 |
| EXAMPLE 49 | 74 | 52 | 37 | 50 |
| COMPARATIVE EXAMPLE 9 | 71 | 38 | 24 | 200 |
| COMPARATIVE EXAMPLE 10 | 0 | 0 | 0 | 6000 |
| COMPARATIVE EXAMPLE 11 | 89 | 40 | 25 | 100 |
| COMPARATIVE EXAMPLE 12 | 63 | 27 | 16 | 200 |

As above, it can be seen that the material that maintains high gas decomposition performance under the irradiation of visible light having illuminances of 2500 lx, 1000 lx, 600 lx exhibits high photocatalytic performance also under a low illuminance of about 200 lx such as an illuminance in a living room where people enjoy gathering and a wash room. Further, it is possible to provide a high-sensitive visible light responsive photocatalyst powder which exhibits gas decomposition performance also under a significantly low illuminance of around 50 lx such as an illuminance on a ceiling, a wall, a floor, and in a place where a furniture, a home electric appliance and the like are disposed in the indoor. It is of course that such a material exhibits excellent photocatalytic performance also under a high illuminance such as 6000 lx.

Example 50

A copper oxide (CuO) powder of 1 mass % was mixed in the tungsten oxide powder obtained in the example 46. Gas decomposition rates of thus obtained tungsten oxide powder were measured in the same manner as that of the example 44. Ratios of the gas decomposition rates under 2500 lx, 1000 lx, 600 lx with respect to the gas decomposition rate under 6000 lx were high to be 94%, 78%, 64%, respectively. As a result of this, it was confirmed that the gas decomposition rate of 8% was exhibited also under an illuminance of 10 lx, and thus good gas decomposition performance could be obtained also under a low illuminance.

Example 51

A water-type coating material was prepared by adding 5 mass % of the tungsten oxide powder produced in the example 46 and 0.05 mass % of colloidal silica. This was applied on glass to be dried, whereby glass having a photocatalytic coating layer was fabricated. Gas decomposition rates of such glass were measured in the same manner as that with respect to the powder. In result, it was confirmed that the gas decomposition rate of 3% was exhibited under an illuminance of 50 lx, and thus good gas decomposition performance could be obtained also under a low illuminance.

Further, when the aforesaid coating material was applied on glass in an indoor space of an automobile, smell of cigarette was reduced and the glass was not easily stained. Incidentally, when a hydrophilic property of the glass coated with the coating material was evaluated, a contact angle was 1° or less and an ultrahigh hydrophilic property was exhibited. Further, when antibacterial performance was evaluated by using *Staphylococcus aureus*, colon *bacillus*, and mold, it was confirmed that excellent antibacterial performance was exhibited against any of them. The visible light responsive photocatalyst powder of the example is excellent in decomposition performance of organic gas such as acetaldehyde, and further, the photocatalytic coating layer has high transmittance and is unlikely to have a visual problem such as uneven color. Therefore, they are suitably used for members used in an indoor space of an automobile, building materials used in factories, stores, public facilities, homes and the like, interior materials, home electric appliances, and so on.

Examples 52, 53

A Pd powder of 15 mass % was mixed in each of the tungsten oxide powders obtained in the example 46 and the example 48. Gas decomposition rates of thus obtained tungsten oxide composite material powders were measured in the same manner as that of the example 44. Ratios of the gas decomposition rates under the irradiation of visible light with an illuminance of 600 lx with respect to the gas decomposition rates under the irradiation of visible light with an illuminance of 6000 lx were 79%, 40%, respectively, and high gas decomposition performance was exhibited also under a lower illuminance, regardless of particle sizes of the tungsten oxide powders. However, since the color of the powder is black, when a coating material was produced, transparency thereof was eliminated.

Example 54

The tungsten oxide powder obtained in the example 46 was dispersed in an aqueous iron chloride solution. The dispersion liquid was centrifuged, and removal of supernatant and washing by adding water were conducted two times. Thereafter, a powder obtained after removing the supernatant was dried at 110° C. for 12 hours, to thereby produce a tungsten oxide composite material powder containing 1 mass % of Fe. Gas decomposition rates of the powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 63%, and high gas decomposition performance was exhibited also under a lower illuminance.

Example 55

Through the same method as that of the example 54, a tungsten oxide composite material powder containing 0.3 mass % of Cu was produced using an aqueous copper chloride solution. Gas decomposition rates of the powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 65%, and high gas decomposition performance was exhibited also under a lower illuminance.

Example 56

Through the same method as that of the example 54, a tungsten oxide composite material powder containing 0.5 mass % of Ag was produced using an aqueous silver nitrate solution. Gas decomposition rates of the powder were measured in the same manner as that of the example 1. A ratio of the gas decomposition rate under the irradiation of visible light with an illuminance of 600 lx with respect to the gas decomposition rate under the irradiation of visible light with an illuminance of 6000 lx was 63%, and high gas decomposition performance was exhibited also under a lower illuminance.

Examples 57 to 60

Through the same method as that of the example 54, tungsten oxide composite material powders containing 2 mass % of Pd and 0.5 mass % of Pd, respectively, were produced using an aqueous palladium chloride solution, thereby obtaining powders of an example 57 and an example 58. Further, tungsten oxide composite material powders were produced in the same manner as that of the example 58 except in that the tungsten oxide powders obtained in the example 44 and the example 47 were used, thereby obtaining powders of an example 59 and an example 60. Gas decomposition rates of these powders were measured in the same manner as that of the example 44. Ratios of the gas decomposition rates under the irradiation of visible light with an illuminance of 600 lx with respect to the gas decomposition rates under the irradiation of visible light with an illuminance of 6000 lx indicated values of 79%, 81%, 62%, 52%, respectively. High gas decomposition performance was exhibited also under a lower illuminance, regardless of particle sizes of the tungsten oxide powders. However, the powder containing 2 mass % of Pd exhibited gas decomposition performance which was lower than that of the powder containing 0.5 mass % of Pd, maybe because an excess amount of Pd existed around tungsten oxide particles.

Example 61

The tungsten oxide powder obtained in the example 46 was dispersed in an aqueous chloroplatinic acid solution, and visible light was irradiated thereto and methanol was put therein, to thereby perform supporting through a photodeposition method. A centrifugation was performed, and after removal of supernatant and washing by adding water were conducted two times, a powder obtained after removing the supernatant was dried at 110° C. for 12 hours, to thereby produce a tungsten oxide composite material powder containing 0.1 mass % of Pt. Gas decomposition rates of the powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx indicated a high value of 84%, and high gas decomposition performance was exhibited also under a lower illuminance.

Examples 62 to 64

Tungsten oxide composite material powders of an example 62, an example 63 and an example 64 were produced by mixing titanium oxide powders ST-01 (product name, Ishihara Sangyo Kaisha, Ltd.) in the tungsten oxide powders obtained in the example 46 at ratios of 70 mass %, 40 mass %, 10 mass %, respectively. The mixing was conducted using a mortar. Gas decomposition rates of these powders were measured in the same manner as that of the example 44. Ratios of the gas decomposition rates under the irradiation of visible light with an illuminance of 600 lx with respect to the gas decomposition rates under the irradiation of visible light with an illuminance of 6000 lx indicated values of 41%, 63%, 65%, respectively. Although the performance of the powder of the example 62 was slightly deteriorated because an amount of tungsten oxide was too small, each of the powders exhibited high decomposition performance also under a lower illuminance.

Examples 65, 66

Powders of an example 65 and an example 66 were produced through the same method as that of the example 63 except in that the tungsten oxide powders obtained in the example 44 and the example 48 were used, in which a titanium oxide powder of 10 mass % was mixed in each of the tungsten oxide powders. Gas decomposition rates of these powders were measured in the same manner as that of the example 44. Ratios of the gas decomposition rates under the irradiation of visible light with an illuminance of 600 lx with respect to the gas decomposition rates under the irradiation of visible light with an illuminance of 6000 lx were 63%, 49%, respectively, and high gas decomposition performance was exhibited also under a lower illuminance.

Example 67

The tungsten oxide powder obtained in the example 46 was dispersed in a titanium oxide sol STS-01 (product name, Ishihara Sangyo Kaisha, LTd.), and thereafter, the resultant was dried at 110° C. for 12 hours, thereby producing a tungsten oxide composite material powder containing 5 mass % of $TiO_2$. Gas decomposition rates of this powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx indicated a value of 66%. It is thought that the high performance was obtained because $TiO_2$ was uniformly dispersed compared to a case where $TiO_2$ was mixed in a state of powder.

Example 68

Through the same method as that of the example 50, a powder in which 20 mass % of CuO powder was mixed in the tungsten oxide powder obtained in the example 46, was produced. Gas decomposition rates of this powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx indicated a value of 61%. However, the powder had gas decomposition performance, under a low illuminance, which was lower than that of the powder in which 1 mass % of CuO powder was mixed maybe because the content of CuO was too large, and since the color of the powder is black, when a coating material was produced, transparency thereof was eliminated.

Example 69

A zirconium oxide ($ZrO_2$) powder of 0.5 mass % was mixed in the tungsten oxide powder obtained in the example 46. Gas decomposition rates of this powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 65%, and high gas decomposition performance was exhibited also under a lower illuminance.

Example 70

The tungsten oxide powder obtained in the example 46 was dispersed in an alumina sol, and the dispersion liquid was dried at 110° C. for 12 hours to produce a powder containing 2 mass % of $Al_2O_3$. Gas decomposition rates of this powder were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 63%, and high gas decomposition performance was exhibited also under a lower illuminance.

Examples 71 to 73

Powders of an example 71, an example 72 and an example 73 were produced by mixing tungsten carbide (WC) powders in the tungsten oxide powders obtained in the example 46 at ratios of 10 mass %, 2 mass %, 0.5 mass %, respectively. Gas decomposition rates of these powders were measured in the same manner as that of the example 44. Ratios of the gas decomposition rates under the irradiation of visible light with an illuminance of 600 lx with respect to the gas decomposition rates under the irradiation of visible light with an illuminance of 6000 lx indicated values of 46%, 62%, 65%, respectively. Although the performance of the composite material powder of the example 71 was slightly deteriorated maybe because the content of WC was too large, each of the powders exhibited high gas decomposition performance also under a lower illuminance. However, since the color of the powder becomes more black as the content ratio of WC is higher, when a coating material was produced, transparency thereof was eliminated.

Example 74

A dispersion process in a beads mill was conducted using the tungsten oxide powder obtained in the example 46 and water, thereby producing a water-type dispersion liquid whose concentration was 10 mass %. An aqueous cerium chloride solution was mixed in the dispersion liquid to produce a solution in which a mass ratio between Ce and $WO_3$ was 1:999. The solution was applied on a glass plate and then dried at 110° C. for 0.5 hour, to thereby produce a sample. For comparison, the similar sample was produced using only the water dispersion liquid before cerium chloride was mixed therein. Gas decomposition rates of these samples were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 47%, a value of the rate being the same as that of the dispersion liquid before Ce was added thereto.

Example 75

The sample produced in the example 74 was further subjected to heat treatment in the atmosphere at 350° C. for 1 hour. Gas decomposition rates of the sample were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 57%, a value of the rate being higher than that of the sample (example 74) which was only dried at 110° C. It is thought that the property was improved because excess moisture, chloride and the like were reduced by setting a high heating temperature.

Example 76

A water-type dispersion liquid containing 10 mass % of tungsten oxide was produced by using the powder in the example 46 in the same manner as that of the example 74, and an aqueous nickel nitrate solution was mixed in the dispersion liquid to produce a solution in which a mass ratio between Ni and $WO_3$ was 1:999. The solution was applied on a glass plate and then dried at 110° C. for 0.5 hour, and further heated in the atmosphere at 350° C. for 1 hour, to thereby produce a sample. Gas decomposition rates of the sample were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 54%, and high gas decomposition performance was exhibited also under a lower illuminance.

Example 77

A water-type dispersion liquid containing 10 mass % of tungsten oxide was produced by using the powder in the example 46 in the same manner as that of the example 76, and an aqueous manganese chloride solution was mixed in the dispersion liquid to produce a solution in which amass ratio between Mn and $WO_3$ was 1:999. The solution was applied on a glass plate and then dried at 110° C. for 0.5 hour, and further heated in the atmosphere at 350° C. for 1 hour, to thereby produce a sample. Gas decomposition rates of the sample were measured in the same manner as that of the example 44. A ratio of the gas decomposition rate under the irradiation of visible light with an illuminance of 600 lx with respect to the gas decomposition rate under the irradiation of visible light with an illuminance of 6000 lx was 54%, and high gas decomposition performance was exhibited also under a lower illuminance. Each sample of the aforementioned respective examples was confirmed to have high hydrophilic property, antibacterial property and antifungal property.

Example 78

A tungsten trioxide powder whose average particle size was 0.5 was prepared as a raw material powder. This raw material powder was sprayed to RF plasma together with carrier gas (Ar), and as reaction gas, oxygen was supplied at a flow rate of 80 L/min. As above, a tungsten oxide powder was produced through a sublimation process in which an oxidation reaction of the raw material powder was caused while the raw material powder was being sublimated. The production conditions of the tungsten oxide powder are shown in Table 10.

Regarding the obtained tungsten oxide powder, a BET specific surface area and an average particle size (by image analysis of a TEM photo) were measured in the same manner as that of the example 1. The measurement results of the BET specific surface area and the average particle size are shown in Table 11. Further, X-ray diffraction was performed on the tungsten oxide powder in the same manner as that of the example 1. An identification result of a crystal structure of the tungsten oxide powder based on the result of the X-ray diffraction is shown in Table 11. Further, color of the tungsten oxide powder was measured based on an L*a*b* color system, similar to the example 1. The measurement result of the L*a*b* is shown in Table 11.

Next, as a property of the obtained tungsten oxide powder, acetaldehyde decomposition rate was measured. The acetaldehyde gas decomposition rate was evaluated by using a flow-type apparatus as is used in the evaluation of nitrogen oxide removal performance (decomposition performance) of JIS-R-1701-1 (2004), under the following conditions. The gas decomposition rates at the time of irradiating visible light having illuminances of 6000 lx, 2500 lx, 1000 lx, 600 lx, 200 lx, 100 lx, 50 lx, 10 lx are shown in Table 12. The tungsten oxide powder in the example 78 exhibited the gas decomposition rate of 21% under the illuminance of 200 lx. Further, the powder exhibited the gas decomposition rate of 11% under the illuminance of 100 lx, and the gas decomposition rate of 7% under the illuminance of 50 lx. It was confirmed that the tungsten oxide powder in the example 53 exhibited a good gas decomposition rate under an illuminance up to 50 lx, and exhibited gas decomposition performance even under a quite low illuminance of 10 lx.

In the acetaldehyde gas decomposition test, an initial concentration of acetaldehyde was 10 ppm, a gas flow rate was 140 mL/min, and a sample amount was 0.2 g. For the adjustment of the sample, it was applied on a 5×10 cm glass plate and was dried. In a case of a powder sample, it was spread by water to be dried. In a pre-process, 12-hour irradiation of black light was performed. As a light source, a white fluorescent lamp (FL20SS•W/18 manufactured by Toshiba Lighting & Technology Corporation) was used, and light having a wavelength of less than 380 nm was cut by using an ultraviolet cutoff filter (Clarex N-169, manufactured by Nitto Jushi Kogyo Co., Ltd.). Illuminances were respectively adjusted to predetermined values. First, a waiting time without any light irradiation was continued until there occurred no gas absorption and the condition was stabilized. After the stabilization, the light irradiation was started. Under such conditions, the light was emitted and the gas concentration was measured 15 minutes later for finding the gas decomposition rate. However, when the gas concentration was not stabilized even after 15 minutes passed, the light irradiation was continued until the stabilization, and the concentration was measured. As a gas analyzing apparatus, a multi-gas monitor 1412 manufactured by INOVA was used.

Example 79

A tungsten oxide powder was produced through the same sublimation process as that of the example 53 except in that, as reaction gas, argon was supplied at a flow rate of 80 L/min and oxygen was supplied at a flow rate of 5 L/min, and the pressure in a reaction vessel was adjusted to a pressure-reduced side of 35 kPa. Further, the tungsten oxide powder was subjected to heat treatment in the atmosphere under the condition of 450° C.×0.5 h. At this time, the temperature was raised to the heat treatment temperature in 0.5 hour, and after the heat treatment, it was lowered to the room temperature in 2 hours. The tungsten oxide powder thus obtained was subjected to the same measurement and evaluation as those of the example 78. The production conditions of the tungsten oxide powder are shown in Table 10, the measurement results of powder properties are shown in Table 11, and the measurement results of gas decomposition rate are shown in Table 12. The tungsten oxide powder according to an example 79 was confirmed to exhibit good gas decomposition performance also under a low illuminance. Further, the powder was confirmed to exhibit an activity even under an illuminance of 10 lx.

Examples 80 to 82

In examples 80 to 82, the same sublimation process as that of the example 78 was performed. In the example 80, as reaction gas, argon was supplied at a flow rate of 40 L/min and air was supplied at a flow rate of 40 L/min in the sublimation process, and a heat treatment process was performed under the condition of 500° C.×1 h after the sublimation process.

The temperature was raised to the heat treatment temperature in 0.5 hour, and after the heat treatment, it was lowered to the room temperature in 2 hours. In the example 81, as reaction gas, argon was supplied at a flow rate of 40 L/min and oxygen was supplied at a flow rate of 100 L/min in the sublimation process, and a heat treatment process was performed under the condition of 600° C.×0.5 h after the sublimation process. The temperature was raised to the heat treatment temperature in 0.5 hour, and after the heat treatment, it was lowered to the room temperature in 2 hours. In the example 82, as reaction gas, argon was supplied at a flow rate of 40 L/min and oxygen was supplied at a flow rate of 40 L/min in the sublimation process, and a heat treatment process was performed under the condition of 800° C.×0.5 h after the sublimation process. The temperature was raised to the heat treatment temperature in 0.5 hour, and after the heat treatment, it was lowered to the room temperature in 2 hours.

The obtained tungsten oxide powders were subjected to the same measurement and evaluation as those of the example 78. The production conditions of the tungsten oxide powders are shown in Table 10, the measurement results of powder properties are shown in Table 11, and the measurement results of gas decomposition rates are shown in Table 12. Each of the tungsten oxide powders according to the examples 80 to 82 was confirmed to exhibit good gas decomposition performance also under a low illuminance. Further, in each of the examples 80 to 82, it was confirmed that the activity was exhibited even under an illuminance of 10 lx.

Example 83

The sublimation process was performed in the same manner as that of the example 78 except in that argon was supplied at a flow rate of 40 L/min and oxygen was supplied at a flow rate of 40 L/min as reaction gas, and thereafter, a heat treatment process was performed in the atmosphere under the condition of 950° C.×0.75 h. The obtained tungsten oxide powder was subjected to the same measurement and evaluation as those of the example 78. The production conditions of the tungsten oxide powder are shown in Table 10, the measurement results of powder properties are shown in Table 11, and the measurement results of gas decomposition rate are shown in Table 12. Although the tungsten oxide powder according to an example 83 exhibited good gas decomposition performance under illuminances of 200 to 50 lx, the performance was inferior to that of the examples 78 to 82. Accordingly, although it was not possible to obtain the gas decomposition performance when the illuminance was lowered to 10 lx, the gas decomposition rate of 5% was exhibited under an illuminance of 200 lx.

Comparative Example 13

A tungsten oxide powder produced through the same sublimation process as that of the example 80 was subjected to heat treatment in the atmosphere under the condition of 1050° C.×0.25 h. The obtained tungsten oxide powder was subjected to the same measurement and evaluation as those of the example 78. The production conditions of the tungsten oxide powder are shown in Table 10, the measurement results of powder properties are shown in Table 11, and the measurement results of gas decomposition rate are shown in Table 12. The tungsten oxide powder had a rather small BET specific surface area of 4 $m^2/g$ and a rather large average particle size of 215 nm, so that the gas decomposition rate thereof under 200 lx was low, and no gas decomposition performance was exhibited under 100 lx and 50 lx. It is thought that this is because particle growth occurred by the high-temperature heat treatment.

Comparative Example 14

The same measurement and evaluation as those of the example 78 were performed by using a tungsten oxide powder (manufactured by Rare Metallic Co., Ltd.) available on the market as a reagent. Powder properties are shown in Table 11, and the measurement results of gas decomposition rate are shown in Table 12. From a result of X-ray diffraction, a crystal system was estimated to be a mixed crystal of a monoclinic crystal and a triclinic crystal, a BET specific surface area was 0.7 $m^2/g$ and an average particle size was 1210 nm. Since the tungsten oxide powder of a comparative example 14 had a small specific surface area and a significantly large particle size, although it was confirmed to have very little gas decomposition performance under 6000 lx, it exhibited no gas decomposition performance under 2500 lx or lower.

Comparative Example 15

In order to improve a visible light activity, titanium oxide supporting Pt was produced, and was subjected to the same measurement and evaluation as those of the example 78. Powder properties other than a crystal system are shown in Table 11, and the measurement results of gas decomposition rate are shown in Table 12. A BET specific surface area was large to be 210 $m^2/g$, and an average particle size was small to be 7.2 nm. The gas decomposition rates under 6000 lx and 2500 lx were relatively high, but, only the gas decomposition rates of 29%, 18%, 5% under 1000 lx, 600 lx, 200 lx, respectively, were obtained, values of the rates being smaller than those of the examples. Accordingly, it was confirmed that the gas decomposition performance under 100 lx was very little, no gas decomposition performance was exhibited under 50 lx or lower, and thus the activity was low under a low illuminance.

Comparative Example 16

In order to improve a visible light activity, titanium oxide supporting Fe was produced, and was subjected to the same measurement and evaluation as those of the example 78. Powder properties other than a crystal system are shown in Table 11, and the measurement results of gas decomposition rate are shown in Table 12. A BET specific surface area was large to be 170 $m^2/g$, and an average particle size was small to be 8 nm. The gas decomposition rates under 6000 lx and 2500 lx were relatively high, but, only the gas decomposition rates of 26%, 16% under 1000 lx and 600 lx, respectively, were obtained, values of the rates being smaller than those of the examples. Accordingly, it was confirmed that the gas decomposition performance under 200 lx was very little, no gas decomposition performance was exhibited under 100 lx or lower, and thus the activity was low under a low illuminance.

TABLE 10

| | PRODUCTION CONDITIONS | | | | |
|---|---|---|---|---|---|
| | SUBLIMATION PROCESS | | | HEAT TREATMENT PROCESS | |
| | RAW MATERIAL | METHOD | GAS (FLOW RATE) [L/min] | TEMPERATURE [° C.] | TIME [h] |
| EXAMPLE 78 | $WO_3$ | PLASMA | O(80) | — | — |
| EXAMPLE 79 | $WO_3$ | PLASMA | Ar(80) + O(5) | 450 | 0.5 |
| EXAMPLE 80 | $WO_3$ | PLASMA | Ar(40) + Air(40) | 500 | 1 |
| EXAMPLE 81 | $WO_3$ | PLASMA | Ar(40) + O(100) | 600 | 0.5 |
| EXAMPLE 82 | $WO_3$ | PLASMA | Ar(40) + O(40) | 800 | 0.5 |
| EXAMPLE 83 | $WO_3$ | PLASMA | Ar(40) + O(40) | 950 | 0.75 |
| COMPARATIVE EXAMPLE 13 | $WO_3$ | PLASMA | Ar(40) + O(40) | 1050 | 0.25 |
| COMPARATIVE EXAMPLE 14 | — | — | — | — | — |
| COMPARATIVE EXAMPLE 15 | — | — | — | — | — |
| COMPARATIVE EXAMPLE 16 | — | — | — | — | — |

TABLE 11

| | POWDER PROPERTIES | | | | | |
|---|---|---|---|---|---|---|
| | BET SPECIFIC SURFACE AREA [$m^2/g$] | AVERAGE PARTICLE SIZE [nm] | CRYSTAL STRUCTURE | L*a*b* COLOR SYSTEM | | |
| | | | | a* | b* | L* |
| EXAMPLE 78 | 105 | 8.5 | MONOCLINIC CRYSTAL + TRICLINIC CRYSTAL + RHOMBIC CRYSTAL | −10.7 | 10.0 | 80.7 |
| EXAMPLE 79 | 50 | 18 | MONOCLINIC CRYSTAL + TRICLINIC CRYSTAL + RHOMBIC CRYSTAL | −9.3 | 14.0 | 86.0 |
| EXAMPLE 80 | 33 | 29 | MONOCLINIC CRYSTAL + TRICLINIC CRYSTAL + RHOMBIC CRYSTAL | −10.1 | 19.5 | 93.3 |
| EXAMPLE 81 | 25 | 35 | MONOCLINIC CRYSTAL + TRICLINIC CRYSTAL + RHOMBIC CRYSTAL | −11.3 | 23.5 | 91.1 |
| EXAMPLE 82 | 12 | 71 | MONOCLINIC CRYSTAL + TRICLINIC CRYSTAL | −10.2 | 10.3 | 76.2 |
| EXAMPLE 83 | 6.5 | 135 | MONOCLINIC CRYSTAL + TRICLINIC CRYSTAL | −12.9 | 30.3 | 81.9 |
| COMPARATIVE EXAMPLE 13 | 4 | 215 | MONOCLINIC CRYSTAL + TRICLINIC CRYSTAL | −15.4 | 42.6 | 85.0 |
| COMPARATIVE EXAMPLE 14 | 0.7 | 1210 | MONOCLINIC CRYSTAL + TRICLINIC CRYSTAL | −16.5 | 48.2 | 88.3 |
| COMPARATIVE EXAMPLE 15 | 210 | 7.2 | — | — | — | — |
| COMPARATIVE EXAMPLE 16 | 170 | 8.0 | — | — | — | — |

TABLE 12

| | GAS DECOMPOSITION RATE (%) | | | | | | | |
|---|---|---|---|---|---|---|---|---|
| | 6000 lx IRRADIATION | 2500 lx IRRADIATION | 1000 lx IRRADIATION | 600 lx IRRADIATION | 200 lx IRRADIATION | 100 lx IRRADIATION | 50 lx IRRADIATION | 10 lx IRRADIATION |
| EXAMPLE 78 | 95 | 86 | 67 | 49 | 21 | 11 | 7 | 2 |
| EXAMPLE 79 | 92 | 91 | 75 | 61 | 34 | 20 | 15 | 9 |
| EXAMPLE 80 | 89 | 87 | 72 | 56 | 31 | 17 | 12 | 7 |
| EXAMPLE 81 | 79 | 75 | 64 | 50 | 25 | 13 | 9 | 4 |
| EXAMPLE 82 | 50 | 47 | 37 | 30 | 15 | 10 | 5 | 1 |
| EXAMPLE 83 | 25 | 20 | 15 | 10 | 5 | 2 | 1 | 0 |
| COMPARATIVE EXAMPLE 13 | 20 | 15 | 8 | 5 | 2 | 0 | 0 | 0 |
| COMPARATIVE EXAMPLE 14 | 3 | 0 | 0 | 0 | 0 | 0 | 0 | 0 |
| COMPARATIVE EXAMPLE 15 | 73 | 65 | 29 | 18 | 5 | 1 | 0 | 0 |
| COMPARATIVE EXAMPLE 16 | 97 | 61 | 26 | 16 | 4 | 0 | 0 | 0 |

As above, it can be seen that the visible light responsive photocatalyst powder including the tungsten oxide powder according to the respective examples exhibits high photocatalytic performance also under a low illuminance of about 200 lx such as an illuminance in a living room where people enjoy gathering and a wash room, and also exhibits photocatalytic performance even under a significantly low illuminance of about 50 lx such as an illuminance on a wall and in a place where a furniture, a home electric appliance and the like are disposed in the indoor. Further, a material that exhibits relatively high photocatalytic performance under 200 to 50 lx exhibits activity also under little light such as light with an illuminance of 10 lx, and has a property that never existed before. It is of course that such a material exhibits excellent photocatalytic performance not only under a significantly high illuminance of 6000 lx, but also under illuminances of 2500 lx, 1000 lx, 600 lx. From the above, it is possible to provide a visible light responsive photocatalyst powder which can be used in any place as long as it has an environment where light exists.

Example 84

A copper oxide (CuO) powder of 1 mass % was mixed in the tungsten oxide powder obtained in the example 80. Gas decomposition rates of thus obtained tungsten oxide powder were measured in the same manner as that of the example 78. The gas decomposition rates under the irradiation of visible light with illuminances of 6000 lx, 2500 lx, 1000 lx, 600 lx, 200 lx, 100 lx, 50 lx indicated excellent values of 96%, 90%, 74%, 60%, 35%, 18%, 13%, respectively. Further, the gas decomposition rate of 3% was exhibited also under a low illuminance of 10 lx, in which photocatalytic performance was confirmed to be exhibited.

Example 85

A water-type coating material was prepared by adding 5 mass % of the tungsten oxide powder produced in the example 80 and 0.05 mass % of colloidal silica. This was applied on glass to be dried, whereby glass having a photocatalytic coating layer was fabricated. Gas decomposition rates of such glass were measured in the same manner as that with respect to the powder. It was confirmed that the gas decomposition rate under the irradiation of visible light with an illuminance of 200 lx indicated a favorable value of 11%.

Further, when the aforesaid coating material was applied on glass in an indoor space of an automobile, smell of cigarette was reduced and the glass was not easily stained. Incidentally, when a hydrophilic property of the glass coated with the coating material was evaluated, a contact angle was 1° or less and an ultrahigh hydrophilic property was exhibited. Further, when antibacterial performance was evaluated by using *Staphylococcus aureus*, colon *bacillus*, and mold, it was confirmed that excellent antibacterial performance was exhibited against any of them. Further, when the aforesaid coating material was applied on a wash room and in the vicinity thereof in a general home where mold had been conventionally likely to grow, it was confirmed that it became difficult for the mold to grow even in a place to which the illumination was difficult to be applied.

Examples 86, 87

A Pd powder of 15 mass % was mixed in each of the tungsten oxide powders obtained in the example 80 and the example 82. Gas decomposition rates of thus obtained tungsten oxide composite material powders were measured in the same manner as that of the example 78. The gas decomposition rates under the irradiation of visible light with an illuminance of 50 lx indicated values of 23%, 6%, respectively, and indicated values higher than those of the tungsten oxide powders before mixing Pd therein, regardless of particle sizes. However, since the color of the powder is black, when a coating material was produced, transparency thereof was eliminated.

Example 88

The tungsten oxide powder obtained in the example 80 was dispersed in an aqueous iron chloride solution. The dispersion liquid was centrifuged, and removal of supernatant and washing by adding water were conducted two times. Thereafter, a powder obtained after removing the supernatant was dried at 110° C. for 12 hours, to thereby produce a tungsten oxide composite material powder containing 1 mass % of Fe. Gas decomposition rates of the tungsten oxide composite material powder were measured in the same manner as that of the example 78. In result, the gas decomposition rate indicated a high value of 18% under the irradiation of visible light with an illuminance of 50 lx.

Example 89

Through the same method as that of the example 88, a tungsten oxide composite material powder containing 0.3 mass % of Cu was produced using an aqueous copper chloride solution. Gas decomposition rates of the tungsten oxide composite material powder were measured in the same manner as that of the example 78. In result, the gas decomposition rate indicated a high value of 17% under the irradiation of visible light with an illuminance of 50 lx.

Example 90

Through the same method as that of the example 88, a tungsten oxide composite material powder containing 0.5 mass % of Ag was produced using an aqueous silver nitrate solution. Gas decomposition rates of the tungsten oxide composite material powder were measured in the same manner as that of the example 78. In result, the gas decomposition rate indicated a high value of 15% under the irradiation of visible light with an illuminance of 50 lx.

Examples 91 to 94

Through the same method as that of the example 88, tungsten oxide composite material powders containing 2 mass % of Pd and 0.5 mass % of Pd, respectively, were produced using an aqueous palladium chloride solution, thereby obtaining powders of an example 91 and an example 92. Further, tungsten oxide composite material powders were produced in the same manner as that of the example 92 except in that the tungsten oxide powders obtained in the example 78 and the example 82 were used, thereby obtaining powders of an example 93 and an example 94. Gas decomposition rates of these powders were measured in the same manner as that of the example 78. In result, the gas decomposition rates under the irradiation of visible light with an illuminance of 50 lx indicated values of 17%, 22%, 20%, 10%, respectively, and indicated values higher than those of the tungsten oxide powders before adding Pd thereto, regardless of particle sizes. However, the powder in which a content ratio of Pd was 2 mass % exhibited gas decomposition performance which was lower than that of the powder containing 0.5 mass % of Pd, maybe because an excess amount of Pd existed around tungsten oxide particles.

Example 95

The tungsten oxide powder obtained in the example 80 was dispersed in an aqueous chloroplatinic acid solution, and visible light was irradiated thereto and methanol was put therein, to thereby perform supporting through a photodeposition method. A centrifugation was performed, and after removal of supernatant and washing by adding water were conducted two times, a powder obtained after removing the supernatant was dried at 110° C. for 12 hours, to thereby produce a tungsten oxide composite material powder containing 0.1 mass % of Pt. Gas decomposition rates of the powder were measured in the same manner as that of the example 78. In result, the gas decomposition rate indicated a high value of 25% under the irradiation of visible light with an illuminance of 50 lx.

Examples 96 to 98

Tungsten oxide composite material powders of an example 96, an example 97 and an example 98 were produced by mixing titanium oxide powders ST-01 (product name, Ishihara Sangyo Kaisha, Ltd.) in the tungsten oxide powders obtained in the example 80 at ratios of 70 mass %, 40 mass %, 10 mass %, respectively. The mixing was conducted using a mortar. Gas decomposition rates of these powders were measured in the same manner as that of the example 78. In result, the gas decomposition rates under the irradiation of visible light with an illuminance of 50 lx indicated values of 6%, 15%, 18%, respectively. Although the performance of the tungsten oxide composite material powder of the example 96 was slightly deteriorated because an amount of tungsten oxide was too small, the gas decomposition rates of the other powders indicated values higher than those of the tungsten oxide powders before mixing.

Examples 99, 100

Powders of an example 99 and an example 100 were produced through the same method as that of the example 97 except in that the tungsten oxide powders obtained in the example 78 and the example 82 were used, in which a titanium oxide powder of 10 mass % was mixed in each of the tungsten oxide powders. Gas decomposition rates of these powders were measured in the same manner as that of the example 78. In result, the gas decomposition rates under the irradiation of visible light with an illuminance of 50 lx indicated values of 12%, 9%, respectively, and it was confirmed that the powders had the gas decomposition rates better than those of the tungsten oxide powders before the titanium oxide powders were mixed therein.

Example 101

The tungsten oxide powder obtained in the example 80 was dispersed in a titanium oxide sol STS-01 (product name, Ishihara Sangyo Kaisha, LTd.), and thereafter, the resultant was dried at 110° C. for 12 hours, thereby producing a tungsten oxide composite material powder containing 5 mass % of $TiO_2$. Gas decomposition rates of this powder were measured in the same manner as that of the example 78. In result, the gas decomposition rate under the irradiation of visible light with an illuminance of 50 lx indicated a high value of 19%. It is thought that the high performance was obtained because $TiO_2$ was uniformly dispersed compared to a case where $TiO_2$ was mixed in a state of powder.

Example 102

Through the same method as that of the example 84, a powder in which 20 mass % of CuO powder was mixed in the tungsten oxide powder obtained in the example 80, was produced. Gas decomposition rates of this powder were measured in the same manner as that of the example 78. In result, the gas decomposition rate under the irradiation of visible light with an illuminance of 50 lx indicated 8%. However, the powder had a property inferior to that of the tungsten oxide powder in which the CuO powder was mixed at a ratio of 1 mass % maybe because the content of CuO was too large, and since the color of the powder is black, when a coating material was produced, transparency thereof was eliminated.

Example 103

A zirconium oxide ($ZrO_2$) powder of 0.5 mass % was mixed in the tungsten oxide powder obtained in the example 80. Gas decomposition rates of this powder were measured in the same manner as that of the example 78. In result, the gas decomposition rate under the irradiation of visible light with an illuminance of 50 lx indicated a high value of 14%.

Example 104

The tungsten oxide powder obtained in the example 80 was dispersed in an alumina sol, and the dispersion liquid was dried at 110° C. for 12 hours to produce a powder containing 2 mass % of $Al_2O_3$. Gas decomposition rates of this powder were measured in the same manner as that of the example 78. In result, the gas decomposition rate under the irradiation of visible light with an illuminance of 50 lx was 12%, and a property being the same or better than that of the tungsten oxide powder before mixing was exhibited.

Examples 105 to 107

Powders of an example 105, an example 106 and an example 107 were produced by mixing tungsten carbide (WC) powders in the tungsten oxide powders obtained in the example 80 at ratios of 10 mass %, 2 mass %, 0.5 mass %, respectively. Gas decomposition rates of these powders were measured in the same manner as that of the example 78. The gas decomposition rates under the irradiation of visible light with an illuminance of 50 lx indicated values of 7%, 13%, 15%, respectively. Although the value in the example 105 was lower than that of the tungsten oxide powder before mixing maybe because an amount of WC was too large, the values in the example 106 and the example 107 were the same or higher than those of the tungsten oxide powders before mixing. However, since the color of the powder becomes more black as the content ratio of WC is higher, when a coating material was produced, transparency thereof was eliminated.

Example 108

A dispersion process in a beads mill was conducted using the tungsten oxide powder obtained in the example 80 and water, thereby producing a water-type dispersion liquid whose concentration was 10 mass %. An aqueous cerium chloride solution was mixed in the dispersion liquid to produce a solution in which a mass ratio between Ce and $WO_3$ was 1:999. The solution was applied on a glass plate and then dried at 110° C. for 0.5 hour, to thereby obtain a sample of an example 108. For comparison, the similar sample was produced using only the water dispersion liquid before cerium chloride was mixed therein. Gas decomposition rates of these samples were measured in the same manner as that of the example 1. In result, the gas decomposition rate under the irradiation of visible light with an illuminance of 50 lx indicated a value of 4%, the value being the same as that of the dispersion liquid before Ce was added thereto.

Example 109

The sample produced in the example 108 was further subjected to heat treatment in the atmosphere at 350° C. for 1 hour. Gas decomposition rates of the sample were measured in the same manner as that of the example 78. In result, the gas decomposition rate under the irradiation of visible light with an illuminance of 50 lx was 7%, a value of the rate being higher than that of the sample (example 108) which was only dried at 110° C. It is thought that the property was improved because excess moisture, chloride and the like were reduced by setting a high heating temperature.

Example 110

A water-type dispersion liquid containing 10 mass % of tungsten oxide was produced by using the powder in the example 80 in the same manner as that of the example 108, and an aqueous nickel nitrate solution was mixed in the dispersion liquid to produce a solution in which a mass ratio between Ni and $WO_3$ was 1:999. The solution was applied on a glass plate and then dried at 110° C. for 0.5 hour, and further heated in the atmosphere at 350° C. for 1 hour, to thereby obtain a sample of an example 110. Gas decomposition rates of the sample were measured in the same manner as that of the example 78. In result, the gas decomposition rate under the irradiation of visible light with an illuminance of 50 lx indicated a value of 8%, the value being higher than that of the dispersion liquid before Ni was added thereto.

Example 111

A water-type dispersion liquid containing 10 mass % of tungsten oxide was produced by using the powder in the example 80 in the same manner as that of the example 110, and an aqueous manganese chloride solution was mixed in the dispersion liquid to produce a solution in which a mass ratio between Mn and $WO_3$ was 1:999. The solution was applied on a glass plate and then dried at 110° C. for 0.5 hour, and further heated in the atmosphere at 350° C. for 1 hour, to thereby produce a sample. Gas decomposition rates of the sample were measured in the same manner as that of the example 78. In result, the gas decomposition rate under the irradiation of visible light with an illuminance of 50 lx was 7%, a value of the rate being higher than that of the dispersion liquid before Mn was added thereto. Each sample of the aforementioned respective examples was confirmed to have high hydrophilic property, antibacterial property and antifungal property.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A visible light responsive photocatalyst powder comprising a tungsten oxide powder or a tungsten oxide composite material powder having a BET specific surface area in a range of not less than 6.5 $m^2/g$ nor more than 820 $m^2/g$,
    wherein organic gas decomposition performance of the visible light responsive photocatalyst powder responds nonlinearly to an amount of irradiated light under visible light in an illuminance range of not less than 200 lx nor more than 2500 lx.

2. The visible light responsive photocatalyst powder according to claim 1,
    wherein a gas decomposition rate when visible light having only a wavelength of not less than 380 nm and an illuminance of 2500 lx is irradiated by using a white fluorescent lamp and an ultraviolet cutoff filter is 20% or more, the gas decomposition rate (%) being set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

3. The visible light responsive photocatalyst powder according to claim 2,
    wherein the gas decomposition rate when visible light having only a wavelength of not less than 380 nm and an illuminance of 1000 lx is irradiated is 15% or more.

4. The visible light responsive photocatalyst powder according to claim 2,
    wherein the gas decomposition rate when visible light having only a wavelength of not less than 380 nm and an illuminance of 600 lx is irradiated is 10% or more.

5. The visible light responsive photocatalyst powder according to claim 1,
    wherein a gas decomposition rate when visible light having only a wavelength of not less than 410 nm and an illuminance of 2500 lx is irradiated by using a white LED lamp is 20% or more, the gas decomposition rate (%) being set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

6. The visible light responsive photocatalyst powder according to claim 5, wherein the gas decomposition rate when visible light having only a wavelength of not less than 410 nm and an illuminance of 1000 lx is irradiated is 15% or more.

7. The visible light responsive photocatalyst powder according to claim 5, wherein the gas decomposition rate when visible light having only a wavelength of not less than 410 nm and an illuminance of 600 lx is irradiated is 10% or more.

8. The visible light responsive photocatalyst powder according to claim 1,
wherein the tungsten oxide powder or the tungsten oxide composite material powder has a BET specific surface area in a range of not less than 8.2 $m^2/g$ nor more than 410 $m^2/g$.

9. The visible light responsive photocatalyst powder according to claim 1,
wherein the tungsten oxide powder or the tungsten oxide composite material powder has an average particle size (D50) in a range of not less than 1 nm nor more than 200 nm.

10. The visible light responsive photocatalyst powder according to claim 1,
wherein the tungsten oxide powder or the tungsten oxide composite material powder has an average particle size (D50) in a range of not less than 2 nm nor more than 100 nm.

11. The visible light responsive photocatalyst powder according to claim 1,
wherein tungsten oxide that forms the tungsten oxide powder or the tungsten oxide composite material powder has a crystal structure of at least one selected from a monoclinic crystal and a triclinic crystal of tungsten trioxide, or a crystal structure in which a rhombic crystal is mixed with at least one selected from the monoclinic crystal and the triclinic crystal.

12. The visible light responsive photocatalyst powder according to claim 1,
wherein the tungsten oxide powder or the tungsten oxide composite material powder has color whose a* is −5 or less, b* is 5 or more, and L* is 70 or more when the color of the powder is expressed by an L*a*b* color system.

13. The visible light responsive photocatalyst powder according to claim 1,
wherein the tungsten oxide composite material powder contains at least one metal element selected from Ti, Fe, Cu, Zr, Ag, Pt, Pd, Mn, Al and Ce in a range of 50 mass % or less.

14. The visible light responsive photocatalyst powder according to claim 13, wherein the tungsten oxide composite material powder contains the metal element in a range of 10 mass % or less.

15. The visible light responsive photocatalyst powder according to claim 13,
wherein the metal element is contained in the tungsten oxide composite material powder in a form of at least one selected from an elemental substance, a compound, and a composite compound with tungsten oxide.

16. The visible light responsive photocatalyst powder according to claim 15, wherein the metal element is mixed with or supported by tungsten oxide in the selected form.

17. The visible light responsive photocatalyst powder according to claim 13,
wherein the metal element is contained in the tungsten oxide composite material powder as an oxide.

18. The visible light responsive photocatalyst powder according to claim 1,
wherein the tungsten oxide composite material powder contains a copper oxide powder in a range of not less than 1 mass % nor more than 5 mass %.

19. The visible light responsive photocatalyst powder according to claim 1,
wherein the tungsten oxide composite material powder contains a tungsten carbide powder in a range of not less than 1 mass % nor more than 5 mass %.

20. A visible light responsive photocatalyst powder comprising a tungsten oxide powder or a tungsten oxide composite material powder having a BET specific surface area in a range of not less than 6.5 $m^2/g$ nor more than 820 $m^2/g$,
wherein a ratio (G2/G1) of a gas decomposition rate (G2) when visible light having only a wavelength of not less than 380 nm and an illuminance of 2500 lx is irradiated to the visible light responsive photocatalyst powder with any sample amount with respect to a gas decomposition rate (G1) when visible light having only a wavelength of not less than 380 nm and an illuminance of 6000 lx is irradiated to the visible light responsive photocatalyst powder with the same sample amount at the time of irradiating the visible light having the illuminance of 2500 lx by using a white fluorescent lamp and an ultraviolet cutoff filter is 74% or more, the gas decomposition rate (%) being set as a value calculated based on [formula: (A −B)/A×100], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which a sample is placed.

21. The visible light responsive photocatalyst powder according to claim 20,
wherein a ratio (G3/G1) of the gas decomposition rate (G3) when visible light having only a wavelength of not less than 380 nm and an illuminance of 1000 lx is irradiated to the visible light responsive photocatalyst powder with the any sample amount with respect to the gas decomposition rate (G1) when visible light having only a wavelength of not less than 380 nm and an illuminance of 6000 lx is irradiated to the visible light responsive photocatalyst powder with the same sample amount at the time of irradiating the visible light having the illuminance of 1000 lx is 50% or more.

22. The visible light responsive photocatalyst powder according to claim 20,
wherein a ratio (G4/G1) of the gas decomposition rate (G4) when visible light having only a wavelength of not less than 380 nm and an illuminance of 600 lx is irradiated to the visible light responsive photocatalyst powder with the any sample amount with respect to the gas decomposition rate (G1) when visible light having only a wavelength of not less than 380 nm and an illuminance of 6000 lx is irradiated to the visible light responsive photocatalyst powder with the same sample amount at the time of irradiating the visible light having the illuminance of 600 lx is 37% or more.

23. The visible light responsive photocatalyst powder according to claim 20,
wherein the tungsten oxide powder or the tungsten oxide composite material powder has a BET specific surface area in a range of not less than 8.2 $m^2/g$ nor more than 410 $m^2/g$.

24. The visible light responsive photocatalyst powder according to claim 20, wherein the tungsten oxide powder or the tungsten oxide composite material powder has an average particle size (D50) in a range of not less than 1 nm nor more than 200 nm.

25. The visible light responsive photocatalyst powder according to claim 20,
wherein the tungsten oxide powder or the tungsten oxide composite material powder has an average particle size (D50) in a range of not less than 2 nm nor more than 100 nm.

26. The visible light responsive photocatalyst powder according to claim 20,
wherein tungsten oxide that forms the tungsten oxide powder or the tungsten oxide composite material powder has a crystal structure of at least one selected from a monoclinic crystal and a triclinic crystal of tungsten trioxide, or a crystal structure in which a rhombic crystal is mixed with at least one selected from the monoclinic crystal and the triclinic crystal.

27. The visible light responsive photocatalyst powder according to claim 20,
wherein the tungsten oxide powder or the tungsten oxide composite material powder has color whose a* is −5 or less, b* is 5 or more, and L* is 70 or more when the color of the powder is expressed by an L*a*b* color system.

28. The visible light responsive photocatalyst powder according to claim 20, wherein the tungsten oxide composite material powder contains at least one metal element selected from Ti, Fe, Cu, Zr, Ag, Pt, Pd, Mn, Al and Ce in a range of 50 mass % or less.

29. The visible light responsive photocatalyst powder according to claim 28, wherein the tungsten oxide composite material powder contains the metal element in a range of 10 mass % or less.

30. The visible light responsive photocatalyst powder according to claim 28,
wherein the metal element is contained in the tungsten oxide composite material powder in a form of at least one selected from an elemental substance, a compound, and a composite compound with tungsten oxide.

31. The visible light responsive photocatalyst powder according to claim 30,
wherein the metal element is mixed with or supported by tungsten oxide in the selected form.

32. The visible light responsive photocatalyst powder according to claim 28, wherein the metal element is contained in the tungsten oxide composite material powder as an oxide.

33. The visible light responsive photocatalyst powder according to claim 20,
wherein the tungsten oxide composite material powder contains a copper oxide powder in a range of not less than 1 mass % nor more than 5 mass %.

34. The visible light responsive photocatalyst powder according to claim 20,
wherein the tungsten oxide composite material powder contains a tungsten carbide powder in a range of not less than 1 mass % nor more than 5 mass %.

35. A visible light responsive photocatalyst material containing the visible light responsive photocatalyst powder according to claim 20 in a range of not less than 1 mass % nor more than 100 mass %.

36. A visible light responsive photocatalyst coating material containing the visible light responsive photocatalyst material according to claim 35 in a range of not less than 0.1 mass % nor more than 90 mass %.

37. A visible light responsive photocatalyst product, comprising the visible light responsive photocatalyst material according to claim 35.

38. A visible light responsive photocatalyst product, comprising a coating layer of the visible light responsive photocatalyst coating material according to claim 36.

39. A visible light responsive photocatalyst powder comprising a tungsten oxide powder or a tungsten oxide composite material powder having a BET specific surface area in a range of not less than 6.5 m$^2$/g nor more than 820 m$^2$/g,
wherein a gas decomposition rate when visible light having only a wavelength of not less than 380 nm and an illuminance of 200 lx is irradiated by using a white fluorescent lamp and an ultraviolet cutoff filter is 5% or more, the gas decomposition rate (%) being set as a value calculated based on [formula: $(A-B)/A \times 100$], where A represents a gas concentration before light irradiation and B represents a gas concentration when not less than 15 minutes have elapsed from the light irradiation and, at the same time, the gas concentration is stable, the gas concentrations being measured while allowing an acetaldehyde gas having an initial concentration of 10 ppm to flow, at 140 mL/min, into a flow-type apparatus as is used in the evaluation of nitrogen oxide removal performance (decomposition performance) of JIS-R-1701-1 (2004) in which 0.2 g of a sample is placed.

40. The visible light responsive photocatalyst powder according to claim 39,
wherein the gas decomposition rate when visible light having only a wavelength of not less than 380 nm and an illuminance of 100 lx is irradiated is 2% or more.

41. The visible light responsive photocatalyst powder according to claim 39,
wherein the gas decomposition rate when visible light having only a wavelength of not less than 380 nm and an illuminance of 50 lx is irradiated is 1% or more.

42. The visible light responsive photocatalyst powder according to claim 39,
wherein the tungsten oxide powder or the tungsten oxide composite material powder has a BET specific surface area in a range of not less than 8.2 m$^2$/g nor more than 410 m$^2$/g.

43. The visible light responsive photocatalyst powder according to claim 39,
wherein the tungsten oxide powder or the tungsten oxide composite material powder has an average particle size (D50) in a range of not less than 1 nm nor more than 200 nm.

44. The visible light responsive photocatalyst powder according to claim 39,
wherein the tungsten oxide powder or the tungsten oxide composite material powder has an average particle size (D50) in a range of not less than 2 nm nor more than 100 nm.

45. The visible light responsive photocatalyst powder according to claim 39,
wherein tungsten oxide that forms the tungsten oxide powder or the tungsten oxide composite material powder has a crystal structure of at least one selected from a monoclinic crystal and a triclinic crystal of tungsten trioxide, or a crystal structure in which a rhombic crystal is mixed with at least one selected from the monoclinic crystal and the triclinic crystal.

46. The visible light responsive photocatalyst powder according to claim 39,
wherein the tungsten oxide powder or the tungsten oxide composite material powder has color whose a* is −5 or less, b* is 5 or more, and L* is 70 or more when the color of the powder is expressed by an L*a*b* color system.

47. The visible light responsive photocatalyst powder according to claim 39,
wherein the tungsten oxide composite material powder contains at least one metal element selected from Ti, Fe, Cu, Zr, Ag, Pt, Pd, Mn, Al and Ce in a range of 50 mass % or less.

48. The visible light responsive photocatalyst powder according to claim 47,
wherein the tungsten oxide composite material powder contains the metal element in a range of 10 mass % or less.

49. The visible light responsive photocatalyst powder according to claim 47,
wherein the metal element is contained in the tungsten oxide composite material powder in a form of at least one selected from an elemental substance, a compound, and a composite compound with tungsten oxide.

50. The visible light responsive photocatalyst powder according to claim 49,
wherein the metal element is mixed with or supported by tungsten oxide in the selected form.

51. The visible light responsive photocatalyst powder according to claim 47,
wherein the metal element is contained in the tungsten oxide composite material powder as an oxide.

52. The visible light responsive photocatalyst powder according to claim 39, wherein the tungsten oxide composite material powder contains a copper oxide powder in a range of not less than 1 mass % nor more than 5 mass %.

53. The visible light responsive photocatalyst powder according to claim 39,
wherein the tungsten oxide composite material powder contains a tungsten carbide powder in a range of not less than 1 mass % nor more than 5 mass %.

54. A visible light responsive photocatalyst material containing the visible light responsive photocatalyst powder according to claim 39 in a range of not less than 1 mass % nor more than 100 mass %.

55. A visible light responsive photocatalyst coating material containing the visible light responsive photocatalyst material according to claim 54 in a range of not less than 0.1 mass % nor more than 90 mass %.

56. A visible light responsive photocatalyst product, comprising a coating layer of the visible light responsive photocatalyst coating material according to claim 55.

57. A visible light responsive photocatalyst product, comprising the visible light responsive photocatalyst material according to claim 54.

58. A visible light responsive photocatalyst material containing the visible light responsive photocatalyst powder according to claim 1 in a range of not less than 1 mass % nor more than 100 mass %.

59. A visible light responsive photocatalyst coating material containing the visible light responsive photocatalyst material according to claim 58 in a range of not less than 0.1 mass % nor more than 90 mass %.

60. A visible light responsive photocatalyst product, comprising a coating layer of the visible light responsive photocatalyst coating material according to claim 59.

61. A visible light responsive photocatalyst product, comprising the visible light responsive photocatalyst material according to claim 58.

* * * * *